United States Patent
Sharma et al.

(10) Patent No.: US 7,049,398 B1
(45) Date of Patent: *May 23, 2006

(54) MELANOCORTIN METALLOPEPTIDE CONSTRUCTS, COMBINATORIAL LIBRARIES AND APPLICATIONS

(75) Inventors: Shubh D. Sharma, Cranbury, NJ (US); Yiqun Shi, East Brunswick, NJ (US); Wei Yang, Edison, NJ (US); Hui-Zhi Cai, Edison, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 206 days.

This patent is subject to a terminal disclaimer.

(21) Appl. No.: 10/049,718

(22) PCT Filed: Jun. 15, 2000

(86) PCT No.: PCT/US00/16396

§ 371 (c)(1),
(2), (4) Date: Feb. 13, 2002

(87) PCT Pub. No.: WO01/13112

PCT Pub. Date: Feb. 20, 2001

Related U.S. Application Data

(60) Provisional application No. 60/148,994, filed on Aug. 13, 1999.

(51) Int. Cl.
  *A61K 38/04* (2006.01)
  *A61K 51/08* (2006.01)
  *C07K 7/00* (2006.01)

(52) U.S. Cl. .......................... 530/328; 424/1.41; 514/6; 514/16; 514/17; 514/18; 530/312; 530/329; 530/330; 530/331; 530/345

(58) Field of Classification Search ................. 514/6, 514/16, 17, 18; 530/312, 328, 329, 330, 530/331, 345

See application file for complete search history.

(56) References Cited

U.S. PATENT DOCUMENTS

| | | | |
|---|---|---|---|
| 5,200,504 A | 4/1993 | Ghadiri | 530/304 |
| 5,277,893 A | 1/1994 | Rhodes | 424/1.49 |
| 5,395,609 A * | 3/1995 | Stuttle | 424/1.69 |
| 5,668,254 A * | 9/1997 | Deghenghi | 530/328 |
| 5,690,905 A | 11/1997 | Zamora et al. | 424/1.69 |
| 5,770,178 A * | 6/1998 | Itaya et al. | 424/1.69 |
| 5,891,418 A | 4/1999 | Sharma | 424/1.69 |
| 6,027,711 A | 2/2000 | Sharma | 424/1.69 |
| 6,048,527 A * | 4/2000 | Granoff et al. | 424/150.1 |
| 2001/0009899 A1* | 7/2001 | Keri et al. | 514/9 |
| 2002/0012948 A1* | 1/2002 | Sharma et al. | 435/7.1 |

OTHER PUBLICATIONS

Fabris et al. Investigation of Zinc Chelation . . . Inorganic Chemistry. 1999, vol. 38, pp. 1322-1325.*

(Continued)

*Primary Examiner*—Jeffrey Edwin Russel
(74) *Attorney, Agent, or Firm*—Stephen A. Slusher

(57) ABSTRACT

Metallopeptides and metallopeptide combinatorial libraries specific for melanocortin receptors are provided, for use in biological, pharmaceutical and related applications. The metallopeptides and combinatorial libraries are made of peptides, peptidomimetics and peptide-like constructs, in which the peptide, peptidomimetic or construct is conformationally fixed on complexation of a metal ion-binding portion thereof with a metal ion.

54 Claims, 8 Drawing Sheets

OTHER PUBLICATIONS

Giblin et al. Design and characterization of alpha-melanotropin peptide analogs . . . Proc. Natl. Acad. Sci. USA. Oct. 1998, vol. 95, pp. 12814-12818.*

Shi et al. Conformationally Constrained Metallopeptide Template For Melanocortin-1 Receptor. American Chemical Society, 218th ACS National Meeting, Abstracts Of Papers, Part 1, abstract MEDI 257.*

Royo, Miriam, et al., "S-Phenylacetamidomethyl (Phacm): an orthogonal cysteine protecting group for Boc and Fmoc solid-phase peptide synthesis strategies," J. Chem. Soc., ed: May 7, 1995; pp. 1095-1102.

Gallop, Mark A., et al., "Journal of Medicinal Chemistry," vol. 37, No. 9; Applications of Combinatorial Technologies to Drug Discovery; Apr. 29, 1994; pp. 1233-1251.

Gordon et al. Journal of Medicinal Chemistry. vol. 37, No. 10, pp. 1385-1401 (May 13, 1994).

* cited by examiner

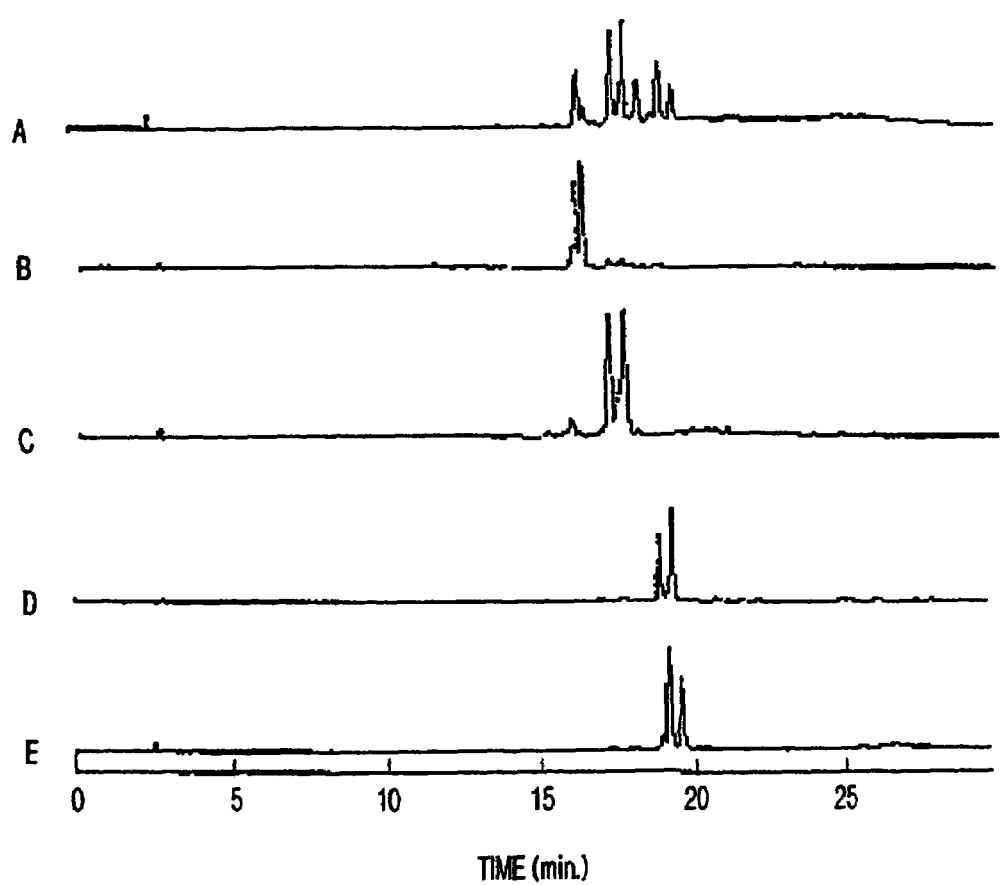
FIGURE 11 A-E

SEQUENCE LISTING

<160> NUMBER OF SEQ ID NOS: 69

<210> SEQ ID NO 1
<211> LENGTH: 4
<212> TYPE: PRT
<213> ORGANISM: Artificial
<220> FEATURE:
<223> OTHER INFORMATION: 6-9 sequence of alpha-melanocyte stimulating
      hormone

<400> SEQUENCE: 1

His Phe Arg Trp
1

<210> SEQ ID NO 2
<211> LENGTH: 4
<212> TYPE: PRT
<213> ORGANISM: Artificial
<220> FEATURE:
<223> OTHER INFORMATION: Synthesized metal-binding sequence, not species
      derived

<400> SEQUENCE: 2

```
Gly Gly Gly Gly
1

<210> SEQ ID NO 3
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 3

His Trp Cys Trp
1

<210> SEQ ID NO 4
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (2)..(2)
<223> OTHER INFORMATION: Hphe

<400> SEQUENCE: 4

His Xaa Cys Trp
1

<210> SEQ ID NO 5
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (2)..(2)
<223> OTHER INFORMATION: 2Nal
<220> FEATURE:
<221> NAME/KEY: MISC_FEATURE
<222> LOCATION: (2)..(2)
<223> OTHER INFORMATION: Nal 2

<400> SEQUENCE: 5

His Xaa Cys Trp
1

<210> SEQ ID NO 6
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (2)..(2)
<223> OTHER INFORMATION: Phg

<400> SEQUENCE: 6

His Xaa Cys Trp
1

<210> SEQ ID NO 7
<211> LENGTH: 4
<212> TYPE: PRT
```

```
<213> ORGANISM: Artificial
<220> FEATURE:
<223> OTHER INFORMATION: Synthetic metal-binding melanocortin-receptor
      specific sequence

<400> SEQUENCE: 7

His Phe Cys Trp
1

<210> SEQ ID NO 8
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 8

His Phe Arg Cys Trp
1               5

<210> SEQ ID NO 9
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 9

His Phe Trp Cys
1

<210> SEQ ID NO 10
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 10

Phe Gly Cys Trp
1

<210> SEQ ID NO 11
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 11

Phe His Gly Cys Trp
1               5

<210> SEQ ID NO 12
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (2)..(2)
<223> OTHER INFORMATION: Tle
```

```
<400> SEQUENCE: 12

Ala Xaa Cys Trp
1

<210> SEQ ID NO 13
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (2)..(2)
<223> OTHER INFORMATION: pF-Phe

<400> SEQUENCE: 13

Ala Xaa Cys Trp
1

<210> SEQ ID NO 14
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (2)..(2)
<223> OTHER INFORMATION: Tyr(3',5' di-I, 4'Ac)

<400> SEQUENCE: 14

Ala Xaa Cys Trp
1

<210> SEQ ID NO 15
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: BAla
<220> FEATURE:
<221> NAME/KEY: MISC_FEATURE
<222> LOCATION: (3)..(3)
<223> OTHER INFORMATION: Cys(Bzl)

<400> SEQUENCE: 15

Xaa Gly Xaa Cys Trp
1               5

<210> SEQ ID NO 16
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: BAla
<220> FEATURE:
<221> NAME/KEY: MISC_FEATURE
<222> LOCATION: (3)..(3)
<223> OTHER INFORMATION: Lys(TFA)
```

```
<400> SEQUENCE: 16

Xaa Gly Xaa Cys Trp
1               5

<210> SEQ ID NO 17
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: BAla
<220> FEATURE:
<221> NAME/KEY: MISC_FEATURE
<222> LOCATION: (3)..(3)
<223> OTHER INFORMATION: Phe(2,4-diCl)

<400> SEQUENCE: 17

Xaa Gly Xaa Cys Trp
1               5

<210> SEQ ID NO 18
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: BAla
<220> FEATURE:
<221> NAME/KEY: MISC_FEATURE
<222> LOCATION: (3)..(3)
<223> OTHER INFORMATION: Phe(2-Cl)

<400> SEQUENCE: 18

Xaa Gly Xaa Cys Trp
1               5

<210> SEQ ID NO 19
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: BAla
<220> FEATURE:
<221> NAME/KEY: MISC_FEATURE
<222> LOCATION: (3)..(3)
<223> OTHER INFORMATION: Lys(Z)

<400> SEQUENCE: 19

Xaa Gly Xaa Cys Trp
1               5

<210> SEQ ID NO 20
<211> LENGTH: 5
<212> TYPE: PRT
<213> ORGANISM: Artificial
<220> FEATURE:
<223> OTHER INFORMATION: Synthetic metal-binding melanocortin-receptor
```

```
                               specific sequence
<220> FEATURE:
<221> NAME/KEY: MISC_FEATURE
<222> LOCATION: (1)..(1)
<223> OTHER INFORMATION: BAla

<400> SEQUENCE: 20

Xaa Gly Leu Cys Trp
1               5

<210> SEQ ID NO 21
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 21

Lys His Phe Cys Trp
1               5

<210> SEQ ID NO 22
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: BAla

<400> SEQUENCE: 22

Xaa His Phe Cys Trp
1               5

<210> SEQ ID NO 23
<211> LENGTH: 6
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 23

Glu His Gly Arg Trp Cys
1               5

<210> SEQ ID NO 24
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Heptanoyl
<220> FEATURE:
<221> NAME/KEY: MISC_FEATURE
<222> LOCATION: (2)..(2)
<223> OTHER INFORMATION: BAla

<400> SEQUENCE: 24

Xaa Xaa Arg Cys Trp
1               5
```

```
<210> SEQ ID NO 25
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Heptanoyl

<400> SEQUENCE: 25

Xaa Ala Arg Cys Trp
1               5

<210> SEQ ID NO 26
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Heptanoyl

<400> SEQUENCE: 26

Xaa Cys Arg Cys Trp
1               5

<210> SEQ ID NO 27
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nle

<400> SEQUENCE: 27

Arg Trp Xaa Cys Phe
1               5

<210> SEQ ID NO 28
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: C6H5-(CH2)2-CO
<220> FEATURE:
<221> NAME/KEY: MISC_FEATURE
<222> LOCATION: (5)..(5)
<223> OTHER INFORMATION: Nle

<400> SEQUENCE: 28

Xaa Arg Trp Cys Xaa
1               5

<210> SEQ ID NO 29
<211> LENGTH: 5
```

```
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: C6H5-(CH2)2-CO
<220> FEATURE:
<221> NAME/KEY: MISC_FEATURE
<222> LOCATION: (2)..(2)
<223> OTHER INFORMATION: Nle

<400> SEQUENCE: 29

Xaa Xaa Trp Cys Arg
1               5

<210> SEQ ID NO 30
<211> LENGTH: 6
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Heptanoyl

<400> SEQUENCE: 30

Xaa Arg Phe His Cys Trp
1               5

<210> SEQ ID NO 31
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Ph(CH2)2-CO

<400> SEQUENCE: 31

Xaa His Arg Cys Trp
1               5

<210> SEQ ID NO 32
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 32

Arg His Phe Cys Trp
1               5

<210> SEQ ID NO 33
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 33
```

```
Arg Trp Phe Cys His
1               5

<210> SEQ ID NO 34
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 34

Trp Phe His Cys Arg
1               5

<210> SEQ ID NO 35
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 35

His Phe Trp Cys Arg
1               5

<210> SEQ ID NO 36
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 36

His Arg Trp Cys Phe
1               5

<210> SEQ ID NO 37
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Heptanoyl

<400> SEQUENCE: 37

Xaa Phe His Cys Trp
1               5

<210> SEQ ID NO 38
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 38

Phe His Cys Trp
1
```

```
<210> SEQ ID NO 39
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle

<400> SEQUENCE: 39

Xaa Ala His Phe Arg Cys Trp
1               5

<210> SEQ ID NO 40
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle

<400> SEQUENCE: 40

Xaa Ala His Phe Arg Cys Trp
1               5

<210> SEQ ID NO 41
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 41

Arg Phe Phe Cys Ser
1               5

<210> SEQ ID NO 42
<211> LENGTH: 6
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nal 2'
<220> FEATURE:
<221> NAME/KEY: MISC_FEATURE
<222> LOCATION: (3)..(3)
<223> OTHER INFORMATION: Nal 2

<400> SEQUENCE: 42

Arg Phe Xaa Asn Cys Phe
1               5

<210> SEQ ID NO 43
<211> LENGTH: 6
<212> TYPE: PRT
<213> ORGANISM: Artificial
<220> FEATURE:
<223> OTHER INFORMATION: Synthetic metal-binding melanocortin-receptor
      specific sequence
```

```
<400> SEQUENCE: 43

Arg Phe Asn Cys Phe
1               5

<210> SEQ ID NO 44
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 44

Arg Phe Cys Phe Asn Ala Phe
1               5

<210> SEQ ID NO 45
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 45

Arg Phe Phe Cys Asn Ala Phe
1               5

<210> SEQ ID NO 46
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 46

Arg Phe Phe Asn Cys Ala Phe
1               5

<210> SEQ ID NO 47
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 47

Arg Phe Phe Asn Ala Cys Phe
1               5

<210> SEQ ID NO 48
<211> LENGTH: 6
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 48

Arg Phe Phe Asn Phe Cys
1               5

<210> SEQ ID NO 49
<211> LENGTH: 7
```

```
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: Aic

<400> SEQUENCE: 49

Xaa Ala His Xaa Arg Cys Trp
1               5

<210> SEQ ID NO 50
<211> LENGTH: 6
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: Aic

<400> SEQUENCE: 50

Xaa Arg Ala Xaa Cys Trp
1               5

<210> SEQ ID NO 51
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: Achc

<400> SEQUENCE: 51

Xaa Ala His Xaa Arg Cys Trp
1               5

<210> SEQ ID NO 52
<211> LENGTH: 6
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: Acpc
```

```
<400> SEQUENCE: 52

Xaa Arg Ala Xaa Cys Trp
1               5

<210> SEQ ID NO 53
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: Acpc

<400> SEQUENCE: 53

Xaa Ala His Xaa Arg Cys Trp
1               5

<210> SEQ ID NO 54
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence

<400> SEQUENCE: 54

His Gly Gly Cys Trp
1               5

<210> SEQ ID NO 55
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (2)..(2)
<223> OTHER INFORMATION: (N-2' naphalene)Phe

<400> SEQUENCE: 55

His Xaa Arg Trp Cys
1               5

<210> SEQ ID NO 56
<211> LENGTH: 12
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nle

<400> SEQUENCE: 56

Tyr Val Xaa Gly His Phe Arg Trp Asp Arg Cys Phe
1               5                   10
```

<210> SEQ ID NO 57
<211> LENGTH: 12
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nle

<400> SEQUENCE: 57

Tyr Val Xaa Gly His Phe Arg Trp Asp Cys Arg Phe
1               5                   10

<210> SEQ ID NO 58
<211> LENGTH: 12
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nle

<400> SEQUENCE: 58

Tyr Val Xaa Gly His Phe Arg Trp Cys Asp Arg Phe
1               5                   10

<210> SEQ ID NO 59
<211> LENGTH: 12
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nle

<400> SEQUENCE: 59

Tyr Val Xaa Gly His Phe Arg Cys Trp Asp Arg Phe
1               5                   10

<210> SEQ ID NO 60
<211> LENGTH: 12
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nle

<400> SEQUENCE: 60

Tyr Val Xaa Gly His Phe Cys Arg Trp Asp Arg Phe
1               5                   10

<210> SEQ ID NO 61
<211> LENGTH: 12
<212> TYPE: PRT
<213> ORGANISM: Artificial
<220> FEATURE:
<223> OTHER INFORMATION: Synthetic metal-binding melanocortin-receptor
      specific sequence

```
<220> FEATURE:
<221> NAME/KEY: MISC_FEATURE
<222> LOCATION: (3)..(3)
<223> OTHER INFORMATION: Nle

<400> SEQUENCE: 61

Tyr Val Xaa Gly His Cys Phe Arg Trp Asp Arg Phe
1               5                   10

<210> SEQ ID NO 62
<211> LENGTH: 12
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (3)..(3)
<223> OTHER INFORMATION: Nle

<400> SEQUENCE: 62

Tyr Val Xaa Gly Cys His Phe Arg Trp Asp Arg Phe
1               5                   10

<210> SEQ ID NO 63
<211> LENGTH: 7
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Nle

<400> SEQUENCE: 63

Xaa Ala His Arg Phe Trp Cys
1               5

<210> SEQ ID NO 64
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (4)..(4)
<223> OTHER INFORMATION: Tic

<400> SEQUENCE: 64

Phe Phe Cys Xaa Lys
1               5

<210> SEQ ID NO 65
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (4)..(4)
<223> OTHER INFORMATION: Inp

<400> SEQUENCE: 65
```

```
Phe Phe Cys Xaa Lys
1               5

<210> SEQ ID NO 66
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (4)..(4)
<223> OTHER INFORMATION: 4-Abz

<400> SEQUENCE: 66

Phe Phe Cys Xaa Lys
1               5

<210> SEQ ID NO 67
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (4)..(4)
<223> OTHER INFORMATION: 3-Abz

<400> SEQUENCE: 67

Phe Phe Cys Xaa Lys
1               5

<210> SEQ ID NO 68
<211> LENGTH: 5
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (4)..(4)
<223> OTHER INFORMATION: 2-Abz

<400> SEQUENCE: 68

Phe Phe Cys Xaa Lys
1               5

<210> SEQ ID NO 69
<211> LENGTH: 4
<212> TYPE: PRT
<213> ORGANISM: Artificial
<220> FEATURE:
<223> OTHER INFORMATION: Synthetic metal-binding melanocortin-receptor
      specific sequence
<220> FEATURE:
<221> NAME/KEY: MISC_FEATURE
<222> LOCATION: (1)..(1)
<223> OTHER INFORMATION: Bz

<400> SEQUENCE: 69

Xaa Arg Trp Cys
1
```

MELANOCORTIN METALLOPEPTIDE CONSTRUCTS, COMBINATORIAL LIBRARIES AND APPLICATIONS

CROSS-REFERENCE TO RELATED APPLICATIONS

This application claims the benefit of the filing of U.S. Provisional Patent Application Ser. No. 60/148,994, entitled Melanocortin Receptor-Specific Metallopeptide Constructs, Combinatorial Libraries and Applications, filed on Aug. 13, 1999, and the specifications thereof is incorporated herein by reference.

GOVERNMENT RIGHTS

The U.S. Government has a paid-up license in this invention and the right in limited circumstances to require the patent owner to license others on reasonable terms as provided for by the terms of Grant No. R43 CA83417 awarded by the National Cancer Institute of the National Institutes of Health of the Department of Health and Human Services and Grant No. R43 DK55470 awarded by the National Institute of Diabetes and Digestive and Kidney Diseases of the National Institutes of Health of the Department of Health and Human Services.

This application is related to International Patent Application Serial No. PCT/US99/29743, entitled Metallopeptide Combinatorial Libraries and Applications, filed Dec. 14, 1999, U.S. Pat. No. 6,027,711, entitled Structurally Determined Metallo-Constructs and Applications, issued Feb. 22, 2000, and U.S. Pat. No. 5,891,418, entitled Peptide—Metal Ion Pharmaceutical Constructs and Applications, issued Apr. 6, 1999, the teachings of all of which are incorporated herein by reference as if set forth in full.

BACKGROUND OF THE INVENTION

1. Field of the Invention (Technical Field):

The present invention relates to metallopeptides, metal ion-complexed peptidomimetics, and metallo-constructs, including metallopeptide combinatorial libraries, metal ion-complexed peptidomimetic and peptide-like combinatorial libraries and metallo-construct combinatorial libraries, specific for melanocortin receptors, including methods for the use and making of the same. The invention also relates to methods for synthesizing and assembling such libraries, and methods for identification and characterization of library constituents which are capable of binding a melanocortin receptor of interest, or mediating a melanocortin receptor-related biological activity of interest.

2. Background Art

Not that the following discussion refers to a number of publications by author(s) and year of publication, and that due to recent publication dates certain publications ar not to be considered as prior art vis-a-vis the present invention. Discussion of such publications herein is given for more complete background and is not to be construed as an admission that such publications are prior art for patentability determination purposes.

Melanocortin Receptors. A family of melanocortin receptor types and subtypes has been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of peripheral tissues.

Peptides specific for melanocortin receptors have been reported to have a wide variety of biological activities, including effects upon pigmentation and steroidogenesis, known to be mediated by MSH (melanocyte stimulating hormone) and ACTH receptors. Several studies have documented the presence of melanotropin receptors on primary human melanoma cells (Tatro J B, Atkins M, Mier J W, et al. Melanotropin receptors demonstrated in situ in human melanoma. *J Clin Invest,* 85:1825–1832, 1990). Melanotropin receptors have been reported as markers for melanotic and amelanotic human melanoma tumors (Sharma S D, Granberry M E, Jiang J, et al. Multivalent melanotropic peptide and fluorescent macromolecular conjugates: new reagents for characterization of melanotropin receptors. *J Clin Invest,* 85:1825–1832, 1990). Melanotropin receptors have been reported as markers for melanotic and amelanotic human Sharma S D, Jiang J, Hadley M E, et al. Melanotropic peptide-conjugated beads for microscopic visualization and characterization of melanoma melanotropin receptors. *Proc Natl Acad Sci USA* 93(24):13715–13720, 1996). In particular, the presence of MC1-R has been demonstrated in human melanoma cells by an antibody to MC1-R (Xia Y, Skoog V, Muceniece R, et al. Polyclonal antibodies against human melanocortin MC-1 receptor: Preliminary immunohistochemical localization of melanocortin MC1 receptor to malignant melanoma cells. *European J Pharmacol* 288: 277–283, 1995). MC1-R is a G protein-coupled, 7-transmembrane receptor expressed in skin-cell melanocytes and shares some degree of homology with related receptors MC2-R, MC3-R, MC4-R and MC5-R. Each of these receptors can bind various peptide analogs that contain a common melanotropic pharmacophore, His-Phe-Arg-Trp (SEQ ID NO:1), which describes the 6–9 sequence of the alpha-melanocyte stimulating hormone (α-MSH).

Prior to molecular characterization of the MC receptors, α-MSH analogs were labeled with the radioisotope Indium-111 and used in melanoma imaging studies (Wraight E P, Bard D R, Maughan T S, et al. The use of a chelating derivative of alpha melanocyte stimulating hormone for the clinical imaging of malignant melanoma. *Brit J Radiology* 65: 112–118, 1992; Bard D R, Knight C G and Page-Thomas D P. A chelating derivative of alpha-melanocyte stimulating hormone as a potential imaging agent for malignant melanoma. *Brit J Cancer* 62:919–922, 1990; Bard D R, Knight C G, Page-Thomas D P. Targeting of a chelating derivative of a short chain analogue of alpha-melanocyte stimulating hormone to Cloudman S91 melanomas. *Biochem Soc Trans* 18:882–883, 1990). Linear and cyclic disulfide-containing peptides have been identified and used for melanoma imaging and appear to be non-selective among MC receptors (Chen J and Quinn T P. Alpha melanocyte stimulating hormone analogues Tc-99 m/Re-188 labeling and their pharmacokinetics in malignant melanoma bearing mice. *J Nucl Med* 39: 222p, 1998; Giblin M F, Wang N, Hoffman T J, et al. Design and characterization of alpha-melanotropin peptide analogs cyclized through rhenium and technetium metal coordination. *Proc Natl Acad Sci USA* 95(22):12814–12818, 1998). In later studies, the cyclic peptide reported by Giblin and coworkers was also found to localize in the brain (Wang N N, Giblin M F, Hoffman T J, et al. In vivo characterization of Tc-99m and Re-188 labeled cyclic melanotropin peptide analogues in a murine melanoma model. *J Nucl Med* 39: 77p, 1998 and corresponding poster presentation at the 45th Society of Nuclear Medicine Meeting, Toronto, June 1998).

It has been recently reported that the response of human melanocytes to UV radiation is mediated by α-MSH induced activation of the cAMP pathway through the MC1-R (Im S, Moro O, Peng F, et al. Activation of the cyclic AMP pathway by alpha-melanotropin mediates the response of human melanocytes to ultraviolet B radiation. *Cancer Res* 58: 47–54, 1998).

MC4-R is also a G protein-coupled, 7-transmembrane receptor, but is believed to be expressed primarily in the brain. Inactivation of this receptor by gene targeting has been reported to result in mice with the maturity-onset obesity syndrome that is associated with hyperphagia, hyperinsulinemia, and hyperglycemia (Huszar D, Lynch C A, Fairchild-Huntress V, et al. Targeted disruption of the melanocortin-4 receptor results in obesity in mice. *Cell* 88:131–141, 1997). MC4-R is a molecular target for therapeutic intervention in energy homeostasis.

Alpha-MSH has been described as a potent anti-inflammatory agent in all major forms of inflammation (Star R A, Rajora N, Huang J, Stock R C, Catania A, and Lipton J M: Evidence of autocrine modulation of macrophage nitric oxide synthase by alpha-melanocyte stimulating hormone. *Proc Natl Acad Sci USA* 92:8016–8020, 1995; Getting S J, and Perretti M: MC3-R as a novel target for antiinflammatory therapy. *Drug News and Perspectives* 13:19–27, 2000). Implication of both MC1-R and MC3-R receptors in anti-inflammatory processes has been stressed. In particular, the activation of these MC receptors by melanocortin receptor agonists has been reported to inhibit the expression of nitric oxide synthase and subsequent nitric oxide production.

Significant work has been done in determining the structure of melanocortin receptors, including both the nucleic acid sequences encoding for the receptors and the amino acid sequences constituting the receptors. See, for example, International Patent Applications No. PCT/US98/12098 and PCT/US99/16862 and U.S. Pat. No. 5,994,087. A large number of ligands specific for melanocortin receptors, both agonists and antagonists, have also been developed. See, for example, International Patent Applications No. PCT/US98/03298 (iodo group-containing melanocortin receptor-specific linear peptide), PCT/GB99/01388 (MC1-R specific linear peptides), PCT/GB99101195 (MC3-R, MC4-R and MC5-R specific cyclic peptides), PCT/US99/04111 (MC1-R specific peptide antagonists for melanoma therapy), PCT/US99/09216 (isoquinoline compounds as melanocortin receptor ligands), PCT/US99/13252 (spiropiperdine derivatives as melanocortin receptor agonists), and U.S. Pat. No. 6,054,556 (cyclic lactam peptides as MC1-R, MC3-R, MC4-R and MC5-R antagonists). In addition, a large number of patents teach various methods of screening and determining melanocortin receptor-specific compounds, as for example International Patent Applications No. PCT/US97115565, PCT/US98112098 and PCT/US99/16862 and U.S. Pat. Nos. 5,932,779 and 5,994,087.

In general, compounds specific for MC1-R ar believed to be useful for treatment of melanoma, including use as radiotherapeutic or drug delivery agent, and as diagnostic imaging agents, particularly when labeled with a diagnostic radionuclide. Compounds specific for MC3-R, MC4-R or MC5-R are believed to be useful in regulation of energy homeostasis, including use as agents for attenuating food intake and body weight gain, for use in treatment of anorexia, as a weight gain aid, for treatment of obesity, and other treatment of other food intake and metabolism-related purposes. Compounds specific for MC3-R and MC4-R, among other melanocortin receptors, can be used as agents for treatment of sexual dysfunction, including male erectile dysfunction. Compounds specific for MC3-R and MC4-R, among other melanocortin receptors, can be used to regulate blood pressure, heart rate and other neurophysiologic parameters. Other melanocortin receptor peptides can be used as tanning agents, to increase melanin production, such as peptides that are MCR-1 agonists. Compounds specific for MCR-1 and MCR-3 may be useful in regulation of inflammatory processes.

There remains a significant need for ligands with high specificity for discrete melanocortin receptors, as well as ligands or compounds that are either agonists or antagonists of specific melanocortin receptors. High affinity peptide ligands of melanocortin receptors can be used to exploit varied physiological responses associated with the melanocortin receptors, either as agonists or antagonists. In addition, melanocortin receptors have an effect on the activity of various cytokines, and high affinity peptide ligands of melanocortin receptors can be used to regulate cytokine activity.

Peptide Libraries and Combinatorial Chemistry. Libraries of peptides and other small molecules, with enormous pools of structurally diverse molecules, are well suited for pharmaceutical lead generation and lead optimization. Libraries of a variety of molecular species have been described in literature and screened for drug discovery, including peptides, peptoids, peptidomimetics, oligonucleotides, benzodiazepines, and other libraries of small organic molecules. Various approaches have been used to construct libraries of structurally diverse chemical compounds, include including chemical synthesis and genetic engineering methods. Chemically synthesized libraries have been synthesized by general solution chemical means and by solid-phase methods. The prior art on designing, synthesizing, screening, and evaluation of peptide-based libraries has been reviewed in numerous articles.

Spatially Addressable Parallel Synthesis of Solid Phase Bound Libraries. Various strategies for chemical construction of a library of peptides or other small molecules are well established. One strategy involves spatially separate synthesis of compounds in parallel on solid phase or on a solid surface in a predetermined fashion so that the location of one compound or a subset of compounds on the solid surface is known. Other methods, such as light-directed spatially addressable parallel chemical synthesis techniques, based upon use of photolithographic techniques in peptide synthesis on a solid surface, such as a borosilicate glass microscope slide, provide libraries containing more than 100,000 spatially separated compounds. How ver, synthesis of libraries that are structurally more diverse than simple peptides requires the development of orthogonal photolabile protecting groups that can be cleaved at different wavelengths of light. In addition, the solid surface bearing these libraries also has been reported to cause a pronounced effect on binding affinities in library screening assays.

Pooling and Split Synthesis Strategies. Large libraries of compounds can be assembled by a pooling strategy that employs equimolar mixtures of reactants in each synthetic step or by adjusting the relative concentration of various reactants in the mixture according to their reactivities in each of the coupling reactions. In one approach equimolar mixtures of compounds are obtained by splitting the resin in equal portions, each of which is separately reacted with each of the various monomeric reagents. The resin is mixed, processed for the next coupling, and again split into equal portions for separate reaction with individual reagents. The process is repeated as required to obtain a library of desired oligomeric length and size. This approach is the basis of the "one-bead one-peptide" strategy which employs amino acid sequencing to ascertain the primary structure of the peptide on a hit bead in a bioassay. Automated systems have been developed for carrying out split synthesis of these libraries with rather more efficiency. A common artifact occasionally seen with all these resin bound libraries is altered target-specific affinity by some solid phase bound compounds in bioassays, which can result in totally misleading results.

Another strategy involves construction of soluble libraries. This strategy involves a deconvolution process of iterative re-synthesis and bioassaying until all the initially randomized amino acid positions are defined. Several modifications to this strategy have been developed, including co-synthesis of two libraries containing orthogonal pools, which eliminates the need of iterative re-synthesis and evaluation. A major limitation of the soluble library approach is its applicability to high affinity systems. The abundance of each compound in solution can be influenced by the total number of compounds in a library that can affect the biological activity. For this reason, a highly active compound in any pool may not in fact be the most potent molecule. Lack of reasonable solubilities of certain members in a library may further influence this phenomenon.

Among the various classes of libraries of small molecules, peptide libraries remain the most versatile because of the structural diversity offered by the use of naturally occurring amino acids, incorporation of a variety of "designer" amino acids, and the high efficiency and ease with which peptide synthesis can be accomplished. In addition, another level of structural diversity in peptide-based libraries has been added by post-synthesis modification of the libraries. These modifications include permethylation, acylation, functionalization of the side chain functionality, and reductive amination of the N-terminus.

SUMMARY OF THE INVENTION
(DISCLOSURE OF THE INVENTION)

In one preferred embodiment, the invention provides a construct comprising a metal ion-binding domain comprising two or more linked residues forming an $N_3S_1$ ligand available for complexing with a metal ion, wherein the construct is conformationally constrained in a structure specific for one or more melanocortin receptors upon complexing the metal ion-binding domain with a metal ion.

In another preferred embodiment, the invention provides a manufactured peptide and pharmaceutically acceptable salts thereof comprising a metal ion-binding domain comprising two or more contiguous amino acids and a determined biological-function domain specific for one or more melanocortin receptors, where in at least a portion of said biological-function domain is co-extensive with at least a portion of the metal ion-binding domain, and wherein said biological-function domain is conformationally constrained upon complexing the metal ion-binding domain with a metal ion.

In another preferred embodiment, the invention provides a combinatorial library targeted to melanocortin receptors of different sequence peptide members synthesized on solid phase, where each constituent library member comprises:
(a) a peptide sequence of three or more amino acid residues bound to solid phase characterized by (i) a sequence of two or more amino acid residues forming a metal ion-binding domain and including at least one amino acid residue containing at least one S wherein the said S is protected by an orthogonal S-protecting group, (ii) a sequence of one or more amino acid residues at the N- or C-terminus of the metal ion-binding domain, or at both the N- and C-terminus of the metal ion-binding domain, and (iii) a cleavable bond attaching the peptide sequence to solid phase; and
(b) a unique selection or sequence of amino acid residues in the peptide sequence of at least one of the constituent members of the library;
wherein the orthogonal S-protecting group may be removed without cleaving the peptide sequence from the solid phase.

In another preferred embodiment, the invention provides a combinatorial library targeted to melanocortin receptors of different sequence peptidomimetic members synthesized on solid phase, where each constituent library member comprises:
(a) a peptidomimetic sequence of a combination of three or more amino acid residues and mimics of amino acid residues bound to solid phase characterized by (i) a sequence of two or more amino acid residues, mimics of amino acid residues or combinations thereof forming a metal ion-binding domain and including at least one amino acid residue or mimic of an amino acid residue containing at least one S wherein the said S is protected by an orthogonal S-protecting group, (ii) a sequence of one or more amino acid residues, mimics of amino acid residues or combinations thereof at the N- or C-terminus of the metal ion-binding domain, or at both the N- and C-terminus of the metal ion-binding domain, and (iii) a cleavable bond attaching the peptidomimetic sequence to solid phase; and
(b) a unique selection or sequence of amino acid residues, mimics of amino acid residues or combinations thereof in the peptidomimetic sequence of at least one of the constituent members of the library;
wherein the orthogonal S-protecting group may be removed without cleaving the peptidomimetic sequence from the solid phase.

In another preferred embodiment, the invention provides a combinatorial library targeted to melanocortin receptors of different sequence peptide or peptidomimetic members synthesized in solution, where each constituent library member comprises:
(a) a peptidomimetic sequence of a combination of three or more amino acid residues and mimics of amino acid residues bound to solid phase characterized by (i) a sequence of two or more amino acid residues, mimics of amino acid residues or combinations thereof forming a metal ion-binding domain and including at least one amino acid residue or mimic of an amino acid residue containing at least one S wherein the said S is protected by an orthogonal S-protecting group, (ii) a sequence of one or more amino acid residues, mimics of amino acid residues or combinations thereof at the N- or C-terminus of the metal ion-binding domain, or at both the N- and C-terminus of the metal ion-binding domain; and
(b) a unique selection or sequence of amino acid residues, mimics of amino acid residues or combinations thereof in the peptidomimetic sequence of at least one of the constituent members of the library.

The compositions of this invention include compositions of the formulas:

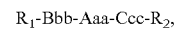

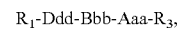

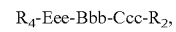

$R_1$-Fff-Aaa-Ggg-Ccc-$R_5$, $R_1$-Hhh-Aaa-Bbb-Ccc-$R_5$, and $R_1$-Iii-Iii-Ccc-Jjj-Kkk-$R_2$, wherein $R_1$ is any functionality that potentiates the intrinsic activity of the remainder of the molecule, including but not limited to providing an auxiliary or secondary receptor contact. Any of a variety of amino acids and non-peptide groups may be employed, including an amino acid chain from one to about four neutral or charged L- or D-configuration amino acid residues. If $R_1$ is a non-peptide group, it may be a linear or branched alkyl, aryl, alkene, alkenyl or aralkyl chain;

Aaa is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Aaa provides an N (nitrogen atom) for metal ion complexation;

Bbb is an L- or D-configuration amino acid with an aromatic side chain. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), or Tyr(BzlCl$_2$), and derivatives, analogs or homologs thereof. The aromatic ring in Bbb may be functionalized with halogen, alkyl or aryl groups. Bbb provides an N for metal ion complexation;

Ccc is an amino acid that provides both an N, from the alpha amino group, and an S (sulfur atom), from a side chain group, for metal ion complexation. Preferred amino acids include L- or D-configuration Cys, Pen and Hcys;

Lll is a D-configuration amino acid with an aromatic side chain. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), or Tyr(BzlCl$_2$), and derivatives, analogs or homologs thereof. The aromatic ring in Lll may be functionalized with halogen, alkyl or aryl groups. Lll does not provide an N for metal ion complexation;

$R_2$ is an amino acid with an aromatic side chain. Preferred amino acids include L- or D-configuration Phe, Trp, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The C-terminus may be free or amidated. $R_2$ may also be the corresponding des-carboxyl amino acid of any of the foregoing. Alternatively, $R_2$ may be eliminated;

Ddd is an amino acid that provides an S, from a side chain group, for metal ion complexation. Preferred amino acids include L- or D-configuration Cys, Pen and Hcys;

$R_3$ is an amino acid with an aromatic side chain that provides an N for metal ion complexation. Preferred amino acids include L- or D-configuration Phe, Trp, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The C-terminus may be free or amidated. $R_3$ may also be the corresponding des-carboxyl amino acid of any of the foregoing;

R4 is a functionality that provides a cationic center. Preferred amino acids include L- or D-configuration Lys, Arg, Orn, Dpr or Dbu, and derivatives, analogs or homologs thereof, including both natural and synthetic amino acids. The N-terminus of the amino acid may be functionalized with any of a variety of neutral amino acid and non-peptide groups, including linear or branched alkyl, aryl, alkene, alkenyl or aralkyl chains;

Eee is an uncharged L- or D-configuration amino acid that provides an N for metal ion complexation. Preferred amino acids include Gly and L-configuration Ala, Nle, Leu, Val, Phe or Trp, and derivatives, analogs or homologs thereof, including both natural and synthetic amino acids. In a preferred embodiment, Eee is an amino acid with an aliphatic side chain;

Fff is an L- or D-configuration aromatic amino acid. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), Tyr(BzlCl$_2$), Tic, Tiq or Tca, and derivatives, analogs or homologs thereof, including both natural and synthetic amino acids. The aromatic ring in Fff may be substituted with halogen, alkyl or aryl groups. Fff does not provide an N for metal ion complexation;

Ggg is an L- or D-configuration aromatic amino acid. Preferred amino acids include L-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The aromatic ring in Ggg may be substituted with halogen, alkyl or aryl groups. Ggg provides an N for metal ion complexation;

$R_5$ is preferably an amide, substituted amide, ester or carboxylate group. $R_5$ may also be and L- or D-configuration amino acid or amino acid amide, including an aromatic, aliphatic, neutral or charged amino acid;

Hhh is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Hhh does not provide an N for metal ion complexation;

Iii is an L- or D-configuration amino acid that provides an N for metal ion complexation. Preferred amino acids includes Ala, Gly, Nle, Val, Leu, Ile, His, Lys, or Arg, and derivatives, analogs or homologs thereof, including both natural and synthetic amino acids;

Jjj is an L- or D-configuration amino acid with an aromatic side chain. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), or Tyr(BzlCl$_2$), and derivatives, analogs or homologs thereof. The aromatic ring in Jjj may be functionalized with halogens, alkyl or aryl groups. Jjj does not provide an N for metal ion complexation; and Kkk is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Aaa does not provide an N for metal ion complexation.

In the compositions of this invention, the metal ion-binding domain can be complexed with a metal ion, and such compositions are included within the invention. The invention further includes compositions wherein the composition is substantially more specific for one or more melanocortin receptors when the metal ion-binding domain is complexed with a metal ion than is the composition when the metal ion-binding amino acid sequence is not complexed with a metal ion.

The combinatorial libraries of this invention include libraries wherein the metal ion-binding domain further comprises at least one N available for binding to a metal ion upon removal of the orthogonal S-protecting group. The combinatorial libraries include compositions wherein the metal ion-binding domain comprises three residues forming an $N_3S_1$ ligand.

In the combinatorial libraries, the orthogonal S-protecting group is S-thio-butyl, acetamidomethyl, 4-methoxytrityl, S-sulfonate or 3-nitro-2-pyridinesulfenyl. The orthogonal S-protecting group may be removed from constituent library members thereof without otherwise altering the constituent library members or any amino acid side chain protecting group therein. In the combinatorial libraries, structural diversity may occurs in the metal ion-binding domain or outside the metal ion-binding domain.

In the combinatorial libraries, one or more constituent library members may include at least one amino acid residue or mimic of an amino acid residue in the sequence at the N- or C-terminus of the metal ion-binding domain containing at least one S wherein the said S is protected by a non-orthogonal S-protecting group, whereby the orthogonal S-protecting group may be removed without removing the non-orthogonal S-protecting group.

For combinatorial libraries limited to amino acids, the amino acid residue containing at least one S wherein the said S is protected by an orthogonal S-protecting group can be an L- or D-3-mercapto amino acid, including but not limited to L- or D-cysteine or L- or D-penicillamine. For combinatorial libraries including amino acid residues and mimics of amino acid residues, the residue containing at least one S wherein the said S is protected by an orthogonal S-protecting group can be an L- or D-3-mercapto amino acid, including but not limited to L- or D-cysteine or L- or D-penicillamine; 3-mercapto phenylananine; 2-mercaptoacetic acid; 3-mercaptopropionic acid; 2-mercaptopropionic acid; 3-mercapto-3,3,-dimethyl propionic acid; 3-mercapto-3,3,-diethyl proprionic acid; 3-mercapto,3-methyl propionic acid; 2-mercapto,2-methyl acetic acid; 3-cyclopentamethylene,3-mercaptopropionic acid; or 2-cyclopentamethylene,2-mercaptoacetic acid.

It is an object of this invention to devise, demonstrate and illustrate the preparation and use of highly specific conformationally restricted peptides, peptoids, related pseudopeptides, peptidomimetics and metallo-constructs formed by complexing sequences thereof to a desired metal ion so that the topography of the side chains in the resulting complex is a biologically active three-dimensional structure specific for melanocortin receptors.

Another object of this invention is to provide peptide-metal ion complexes specific for melanocortin receptors and which have a higher level of stability and are less susceptible to proteolysis than either the uncomplexed peptide, or other peptides known in the art.

Another object of this invention is to provide peptide-metal ion complexes that are specific for different subsets of melanocortin receptors, such as specific only for MC1-R or for MC4-R.

Another object of this invention is to provide peptide-metal ion complexes which are specific for melanocortin receptors and which are agonists or antagonists.

Another object of this invention is to provide for peptide analogs which are not conformationally restricted in the absence of a metal ion, whereby the uncomplexed peptide analog is either inactive or demonstrates low potency, but which is conformationally restricted on complexation with a metal ion and specific for melanocortin receptors with high potency.

Another object of this invention is to utilize metal complexation in a peptide specific for melanocortin receptors to cause specific regional conformational restrictions in the peptide so that the peptide conformation at the metal binding site is conformationally fixed on metal complexation.

Another object of this invention is to complex a peptide to a metal ion, whereby the resulting metallopeptide is specific for melanocortin receptors, and exhibits a preferred in vivo biodistribution profile, rate and mode of clearance, bioavailability and pharmacokinetics in mammals.

Another object of this invention is to provide peptide-metal ion complexes specific for melanocortin receptors utilizing stable non-radioactive metal ions, for use in therapeutic treatment of disease, including as an agent to modify energy metabolism and feeding behavior, such as for treatment of pathologic obesity and related conditions.

Another object of this invention is to provide peptide-metal ion complexes specific for melanocortin receptors utilizing metal ions which are radionuclides for use in diagnostic methods, including imaging and staging of melanoma tumors and melanoma tumor metastases.

Another object of this invention is to provide peptide-metal ion complexes specific for melanocortin receptors utilizing stable non-radioactive metal ions, for use as a prevention agent against ultra-violet radiation-induced DNA damages, including sunlight-induced DNA damage in the skin.

Another object of this invention is to provide peptide-metal ion complexes specific for melanocortin receptors utilizing stable non-radioactive metal ions, for use as a tanning agent, including but not limited to therapeutic use as a tanning agent.

Another object of this invention is to provide peptide-metal ion complexes specific for melanocortin receptors utilizing stable non-radioactive metal ions, for use as anti-inflammatory agents.

Another object of this invention is to complex peptides with radiometal ions, including but not limted to technetium-99m, for use in diagnostic imaging, so that the resulting peptide-metal ion complex is substantially more specific for melanocortin receptors than the uncomplexed peptide molecule, and the resulting radiolabeled species is essentially carrier-free in terms of specificity for melanocortin receptors.

Another object of this invention is to complex peptides with radiometal ions, including radioisotopes of rhenium such as rhenium-186 and rhenium-188, for use in targeted radiotherapy, such as for treatment of melanoma.

Another object of this invention is to provide peptide-metal ion complexes specific for melanocortin receptors that can transit the gut-blood barrier, without significant enzymatic or peptidase degradation, and may be adapted for oral administration.

Another object of this invention is to provide libraries of conformationally constrained peptide-metal ion complexes directed to melanocortin receptors.

Another object of this invention is to provide combinatorial peptide libraries of peptide-metal ion complexes specific for melanocortin receptors, wherein the peptides include a metal ion-binding domain, such that a specific conformational restriction is obtained upon labeling the peptides with a metal ion.

Another object of this invention is to provide combinatorial peptide libraries of peptide-metal ion complexes specific for melanocortin receptors, wherein the amino acids comprising the peptides may be naturally occurring amino acids, isomers and modifications of such amino acids, non-protein amino acids, post-translationally modified amino acids, enzymatically modified amino acids, constructs or structures designed to mimic amino acids, and the like, so that the library includes pseudopeptides and peptidomimetics.

Another object of this invention is to provide metallopeptide libraries specific for one or more melanocortin receptors, wherein the metallopeptides include a metal ion-binding domain, such that a determined conformational restriction is obtained upon labeling the peptides with a metal ion, and the metallopeptides further include distinct, unique and different amino acid sequences.

Another object of this invention is to provide both soluble and solid phase metallopeptide libraries specific for one or more melanocortin receptors, wherein the metallopeptides include a metal ion-binding domain.

Another object of this invention is to provide methods for synthesis of peptides specific for melanocortin receptors wherein the peptide contains a reactive SH group forming a part of a metal ion-binding domain, whereby the reactive SH group is protected during synthesis, and is deprotected only upon complexing the peptides with a metal ion.

Another object of this invention is to provide combinatorial metallopeptide libraries specific for melanocortin receptors wherein the peptides forming the library contain a reverse turn structure as a consequence of metal ion complexation.

Another object of this invention is to provide a method for rapid and efficient complexation of a pool of diverse peptides specific for melanocortin receptors with a metal ion, including a rhenium metal ion.

Another object of this invention is to provide libraries of conformationally constrained peptide-metal ion complexes as surrogates for reverse turn structures, such as beta turns and gamma turns commonly found in naturally occurring peptides and proteins specific for melanocortin receptors. The turns formed as a consequence of metal ion complexation are more stable than the naturally occurring turn structures, which are stabilized only by weaker interactions such as van der Waals' interactions and hydrogen bonds.

Another object of this invention is to provide combinatorial metallopeptide libraries wherein each of the peptides forming the library contain a reverse turn structure as a consequence of metal ion complexation.

Another object of this invention is to provide a method for the identification of specific metallopeptides through internal signatures resulting from use of metal ions with two or more isotopic peaks, such as through use of rhenium containing two isotopes in fixed relative abundance that differ in mass by 2 units.

Other objects, advantages and novel features, and the further scope of applicability of the present invention, will be set forth in part in the detailed description to follow, taken in conjunction with the accompanying drawings, and in part will become apparent to those skilled in the art upon examination of the following, or may be learned by practice of this invention. The objects and advantages of this invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIGS. 11A–11E are reversed phased HPLC profiles of a library pool of 4 metallopeptides synthesized according to Example 6.

DESCRIPTION OF THE PREFERRED EMBODIMENTS

Figure 1:
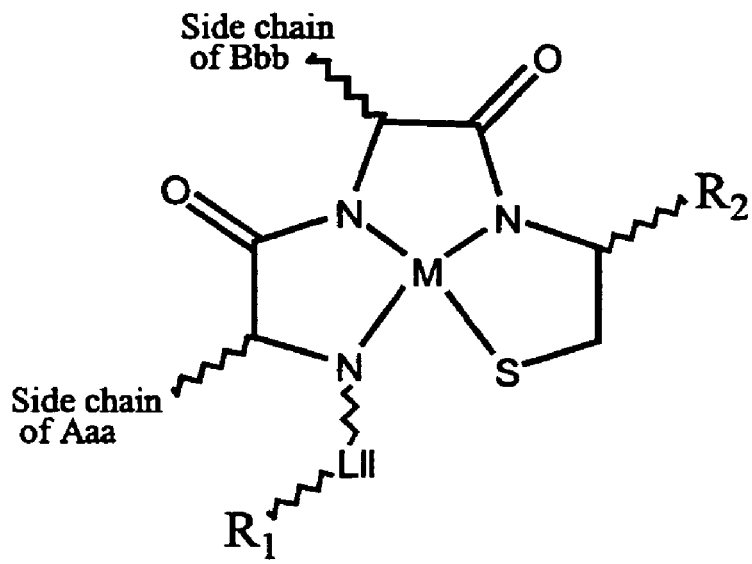
FIG. 1 is a molecular structure for Template 1.

Best Modes for Carrying Out the Invention

Definitions. Certain terms as used throughout the specification and claims are defined as follows:

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by ch mical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, the peptides of this invention comprise fewer than 100 amino acids, and preferably fewer than 60 amino acids, and most preferably ranging from about 2 to 20 amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249–262, 1990; and Toniolo C: *Int J Peptide Protein Res* 35:287–300, 1990; the teachings of all of which are incorporated herein by reference. In addition, the following abbreviations have the meanings giving:

| | |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| 7-Ahept | 7-amino heptanoic acid |
| Aic | 2-aminoindane-2-carboxylic acid |
| 6-Ahx | 6-amino hexanoic acid |
| 8-Aoc | 8-amino octanoic acid |
| Arg(Tos) | $N^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| D/L Atc | (D,L)-2-aminot tralin-2-carboxylic acid |
| 11-Aun | 11-amino und canoic acid |
| AVA | 5-amino valeric acid |
| Bip | biphenylalanine |
| Bz | Benzoyl |
| Cha | Cyclohexylalanine |
| Chg | Cyclohexylglycine |
| Dip | 3,3-Diphenylalanine |
| Et— | Ethyl |
| GAA | epsilon-guanidino acetic acid |
| GBzA | 4-guanidino benzoic acid |
| B-Gpa | 3-guanidino propionic acid |
| GVA(Cl) | beta-chloro-epsilon-guanidino valeric acid |
| Hphe | Homophenylalanine |
| Inp | isonipecotic acid |
| Lys(Z) | N-epsilon-benzyloxycarbonyl-lysine |
| Me— | Methyl |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| (N-PhEt)Nal 2 | N(2-phenylethyl)-3-(2-naphthyl) alanine |
| Phg | Phenylglycine |
| pF-Phe | para-fluoro-phenylalanine |
| Phe(4-Br) | 4-bromo-phenylalanine |
| Phe(4-CF$_3$) | 4-trifluoromethyl-phenylalanine |
| Phe(4-Cl) | 4-chloro-phenylalanine |

-continued

| | |
|---|---|
| Phe(2-Cl) | 2 chloro-phenylalanine |
| Phe(2,4-diCl) | 2,4,-dichloro-phenylalanine |
| Phe(3,4-diCl) | 3,4,-dichloro-phenylalanine |
| Phe(3,4-diF) | 3,4,-difluoro-phenylalanine |
| Phe(4-I) | 4-iodo-phenylalanine |
| Phe(3,4-di-OMe) | 3,4,-dimethoxy-phenylalanine |
| Phe(4-Me) | 4-methyl-phenylalanine |
| Phe(4-NO$_2$) | 4-nitro-phenylalanine |
| Pip | Pipecolic acid |
| Qal(2') | beta-(2-quinolyl)-alanine |
| Sal | 3-styrylalanine |
| TFA | trifluoroacetyl |
| Tic | 1,2,3,4-tetrahydroisoquinoline-3-carboxylic acid |
| Tle | tert-butylalanine |
| Tyr(Bzl) | O-benzyl-tyrosine |
| Tyr(BzlDiCl 2,6) | O-(2,6 dichloro)benzyl-tyrosine |

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

The library constructs of this invention also include a metal ion, which may be an ionic form of any element in metallic form, including but not limited to metals and metalloids. The metal ion may, but need not, be radioactive, paramagnetic or superparamagnetic. The metal ion can be of any oxidation state of any metal, including oxidation states of vanadium (V), manganese (Mn), iron (Fe), cobalt (Co), nickel (Ni), copper (Cu), zinc (Zn), gallium (Ga), arsenic (As), selenium (Se), yttrium (Y), molybdenum (Mo), technetium (Tc), ruthenium (Ru), rhodium (Rh), palladium (Pd), silver (Ag), cadmium (Cd), indium (In), tin (Sn), tungsten (W), rhenium (Re), osmium (Os), iridium (Ir), platinum (Pt), gold (Au), mercury (Hg), thallium (Tl), lead (Pb), bismuth (Bi), polonium (Po), astatine (At), samarium (Sm), europium (Eu), and gadolinium (Gd). The metal ion can also be a radionuclide of any of the foregoing, including In, Au, Ag, Hg, Tc, Re, Sn, At, Y and Cu. A preferred metal ion with a tetradentate coordination sphere is Re. For radiopharmaceutical applications, or applications wherein a radioisotope is desirable for screening, an alpha-, gamma- or beta-emitting radionuclide may be employed.

The coordination sphere of various common metal ions, in general, is tetradentate to hexadentate. In one embodiment according to this invention, an amino acid or amino acid mimetic sequence is included within each library member such that it contains the desired number of groups (4 to 6 in most cases) for complexing with the metal. The molecule is designed so that, upon complexing with a metal, it forms a mimic of a reverse turn structure about the site of metal complexation. A metal with coordination number 4, 5 or 6, and complexing respectively with an amino acid sequence forming a tetra, penta, or hexadentate ligand, will fold and constrain the ligand. The amino acid or amino acid mimetic sequence forming a ligand is defined as the metal ion-binding domain ("MBD") of the peptide or peptidomimetic. A highly flexible molecule like a peptide, in other words, is folded to form a kind of reverse turn upon its complexation with a metal. This resulting turn is a highly constrained structure in the conformational sense.

The biological-binding domain ("BBD") of the peptide or peptidomimetic is defined in the specification and claims as a sequence of one or more amino acids which constitute a biologically active sequence, exhibiting binding to a melanocotin-associated receptor, including MC1-R, MC2-R, MC3-R, MC4-R and MC5-R, thereby constituting the peptide as a member of a specific binding pair. The BBD also includes any sequence, which may be consecutive amino acids or mimetics (sychnological) or nonconsecutive amino acids or mimetics (rhegnylogical) which forms a melanocortin-associated ligand, which ligand is capable of forming a specific interaction with its acceptor or receptor. The term "receptor" is intended to include both acceptors and receptors. The receptor may be a biological receptor. The sequence or BBD may transmit a signal to the cells, tissues or other materials associated with the biological receptor after binding, but such is not required. The BBD may be either an agonist or antagonist, or a mixed agonist-antagonist. A peptide or peptidomimetic complexed to a metal ion with such a BBD constitutes a member of a "specific binding pair," which specific binding pair is made up of at least two different molecules, where one molecule has an area on the surface or in a cavity which specifically binds to a particular spatial and polar organization of the other molecule. Frequently, the members of a specific binding pair are referred to as ligand and receptor or anti-ligand.

The BBD is further defined to include the portion of a construct, wherein the construct is a peptidomimetic, peptide-like, or metallo-construct molecule, which upon binding of the construct with a metal ion, is biologically active, exhibiting binding to a melanocortin receptor found on cells, tissues, organs and other biological materials. The BBD may, in this instance, be sychnological or rhegnylogical, and generally has the attributes and functions of a BBD of a peptide. The BBD may be coextensive with all or a portion of the MBD, so that the same amino acids or other residues which constitute the MBD also constitute all or a part of the BBD. In some instances, one or amino acids of the MBD will form a part of the BBD, and one or more additional amino acids, which are not part of the MBD, form the remainder of the BBD.

Conformational constraint refers to the stability and preferred conformation of the three-dimensional shape assumed by a peptide or other construct. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure. See generally *Synthetic Peptides: A User's Guide*, cited above.

The primary structure of a peptide is its amino acid sequence. The secondary structure deals with the conformation of the peptide backbone and the folding up of the segments of the peptide into regular structures such as α-helices, β-sheets, turns and the like. Thus, the three-dimensional shape assumed by a peptide is directly related to its secondary structure. See generally *Synthetic Peptides: A User's Guide*, cited above, including the text, figures and tables set forth at pages 24–33, 39–41 and 58–67. A global structure refers to a peptide structure which exhibits a preference for adopting a conformationally constrained three-dimensional shape.

The product resulting from the methods set forth herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals. The products of this invention may optionally employ radionuclide ions, which may be used for diagnostic imaging purposes or for radiotherapeutic purposes.

Peptide and Metallo-Construct Molecule Libraries and Combinatorial Chemistries. Using the methods of this invention, libraries of peptides and peptidomimetics are designed wherein each constituent library member includes an MBD sequence necessary for providing a coordination site for complexation with a metal, it being understood that such sequence may differ among the constituent members of the library. Upon complexing the MBD with a metal, a specific structure results, forming a mimic of a reverse turn structure. The specific stereochemical features of this complex are due to the stereochemistry of the coordination sphere of the complexing metal ion. Thus the preferred geometry of the coordination sphere of the metal dictates and defines the nature and extent of conformational restriction.

Libraries of this invention contain constituents which are either locally or globally constrained structures. Libraries may include molecules with either local conformation restrictions or global conformation restrictions, or some combination thereof. This aspect of the invention includes a variety of methods of synthesis, screening and structural elucidation of positive hits in screening systems. The importance of these aspects is well known to those skilled in the art and will also become evident from the following description and examples.

In general, most of the metals that may prove useful in this invention have a coordination number of 4 to 6, and rarely as high as 8, which implies that the putative MBD must be made of residues with reactive groups located in a stereo-compatible manner so as to establish a bond with a metal ion of given geometry and coordination sphere. Coordinating groups in the peptide chain include nitrogen atoms of amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as oxime, hydrazino, sulfhydryl, phosphate, cyano, pyridino, piperidino, or morpholino groups. For a metal with a coordination number of 4, a tetrapeptide amino acid sequence may be employed (such as Gly-Gly-Gly-Gly (SEQ ID NO:2)), or a tripeptide amino acid sequence in which at least one of the amino acids has a side chain with a coordinating group can similarly be employed (such as Gly-Gly-Cys). The side chain can have a nitrogen, oxygen or sulfur-based coordination group. Thus, an amino acid sequence can provide an $N_4$, $N_3S$, $N_2S_2$, $NS_3$, $N_2SO$ or similar ligand, yielding tetradentate coordination of a metal ion utilizing nitrogen, sulfur and oxygen atoms.

In another embodiment of the invention, the MBD includes one or more amino acid residues and one or more derivatized amino acids or spacer sequences, with the derivatized amino acid or spacer sequence having a nitrogen, sulfur or oxygen atom available for complexing with the various oxidation states of the metal. Examples of derivatized amino acids include amide, primary alkyl or aryl amide, 1,2,3,4-tetrahydroisoquinoline-2-carboxylic acid and its corresponding 7-hydroxy derivative, N-carboxymethylated amino acids, 2'-mercapto-Trp, $N^\beta$-(2 mercaptoethane)-α,β-diaminopropionic acid and similar higher homologs of other homologous amino acids, $N^\beta$-(2 aminoethane)-α,β-diaminopropionic acid and similar higher homologs of other homologous amino acids, $N^\beta$-(picolinoyl)-α,β-diaminopropionic acid and similar higher homologs of other homologous amino acids, β-(picolylamide)-Asp and similar homologs of other homologous amino acids, $N^β$-(2-aminobenzoyl)-α,β-diaminopropionic acid and similar higher homologs of other homologous amino acids, β-(2-amidomethylpyridine)-Asp and similar homologs of other homologous amino acids, N-benzyloxycarbonyl amino acid, N-tert butyloxycarbonyl amino acid, N-fluorenylmethyloxycarbonyl amino acid and other similar urethane-protected amino acid derivatives, and other derivatized or synthetic amino acids relating to any of the foregoing. Examples of spacer sequences which may be employed in this invention include 2-mercaptoethylamine, succinic acid, glutaric acid, 2-mercaptosuccinic acid, ethylenediamine, diethylenetriamine, triethylenetetraamine, tetraethylenepentaamine, glycol, polyethylene glycol, thioglycolic acid, mercaptopropionic acid, pyridine-2-carboxylate, picolylamine, 2-mercaptoaniline, 2-aminobenzoic acid, and 2-aminomethylpyridine. In general, any sequence which may be linked, directly or indirectly, to one or two amino acids so as to form a continuous sequence, and which has a nitrogen, sulfur or oxygen atom available for complexing with the valences of the metal ion, may be employed as an element of the MBD.

S-Protected Thiol Group Compounds in Metallo-Libraries. A free thiol (SH) group is preferred for complexation of most metal ions to the peptides and peptidomimetics of this invention, and in many cases an SH group is necessary in order to form a stable exchange-inert complex with a metal. Peptides and other organic molecules with free SH groups, however, are easily oxidized in air and in solution, and can often form a disulfide-linked dimer. If more than one free SH group is present in a molecule, oxidation may lead to a complex polymer. Similarly, if a mixture of different peptides or organic molecules with free SH groups are prepared, oxidation generally leads to a complex mixture of polymers of unknown composition. This is of serious concern in preparing libraries of metallopeptides or other organic molecules where one or more SH group is intended for use in metal complexation.

A variety of SH protecting groups have been employed for a variety of purposes, including radiopharmaceutical manufacture and formulation. For example, in its protected form S-Benzoyl-mercaptoacetyl-glycyl-glycyl-glycine (Bz-MAG$_3$) has been used to complex Tc-99m ($^{99m}$Tc) under conditions where the S-Bz group splits during $^{99m}$Tc complexation. The use of S-Bz protection, how ver, is not compatible with the methods of peptide synthesis.

In order to construct metallopeptide libraries of this invention which incorporate an SH group, if mixed pool synthesis is employed the peptides must be S-protected derivatives. The SH protecting group is chosen such that (a) the synthesis of peptide derivatives with S-protecting group is compatible with methods of solution and solid phase peptide synthesis, so that the S-protecting group is stable during synthetic procedures, and (b) the S-protecting group can be deprotected in situ, without cleavage from the resin in the case of solid phase synthesis, during the metal complexation step. Many prior art methods, such as Bz-MAG$_3$, meet at most only one of the two criteria specified above (Bz-MAG$_3$ meets only criterion (a) above).

Use of orthogonally S-protected thiol groups permits synthesis of metallo-compounds in a single pot. A mixture of compounds, each compound containing an orthogonal S-protected group ("OSPG"), is used for complexation with a metal ion, and it is only during metal ion complexation that the S-protected group is deprotected, and accordingly polymerization and cross-linking is avoided. This procedure thus provides homogenous libraries of metallo-compounds.

One OSPG meeting the criteria specified above, and which can be used in this invention, employs an S$^t$Bu (S-thio-butyl or S-t-butyl) group to protect the SH group. The S$^t$Bu group is stable under both the acidic and basic conditions typically employed in peptide synthesis. Further, the S$^t$Bu group may be cleaved by reduction using a suitable phosphine reagent, which reduction step may be employed immediately prior to or in conjunction with complexation of a metal ion to the peptide. Such OSPG cleavage does not cleave the peptide from the resin, or otherwise alter the structure of the peptide.

Another OSPG meeting the criteria specified above and suitable for this invention employs an S-Acm (S-acetamidomethyl) group to protect the SH group. The Acm group is also stable under the acid and base conditions usually employed during peptide synthesis. The S-Acm group may be removed by treatment of S-Acm-protected peptide or peptide resin with mercury (II) acetate or silver (I) tertrafluoroborate, which liberates the thiol peptide in its mercury or silver ion-complexed state. Free thiol-containing peptide can then be recovered by treating the mercury or silver ion and thiol complexed salts with an excess of a thiol-containing reagent, such as beta-mercaptoethanol or dithiothreitol. The resulting peptide is then used for metal complexation. Alternatively, the mercury or silver ion and thiol complexed peptide may be directly treated with a metal ion complexing reagent to form the desired metallopeptide.

Other examples of OSPGs for metallopeptides include 4-methoxytrityl (Mmt), 3-nitro-2-pyridinesulfenyl (Npys) and S-sulfonate (SO$_3$H). Mmt is selectively removed upon treatment with 1% TFA in dichloromethane. Npys and S-sulfonate are selectively removed by treatment with a thiol-containing reagent such as beta-mercaptoethanol or dithiothreitol or a phosphine reagent such as tributyl phosphine. The Npys group (R. G. Simmonds R G et al: *Int J Peptide Protein Res*, 43:363,1994) is compatible with Boc chemistry for peptide synthesis and the S-sulfonate (Maugras I et al: *Int J Peptide Protein Res*, 45:152, 1995) is compatible with both Fmoc and Boc chemistries. Similar OSPGs derived from homologous series of S-alkyl, or S-aryl, or S-aralkyl may also be used in this invention. A primary characterization of the OSPG is that its use results in the formation of a disulfide (S—S) bond utilizing one sulfur atom each from the thiol-containing amino acid and the protecting group. In addition, the resulting disulfide (S—S) bond is cleavable by the use of any of a variety of disulfide cleaving agents, including but not limited to phosphine and thiol-containing reagents.

The method employing S$^t$Bu protected SH groups, or other OSPGs, may be employed for the generation of either solid phase or soluble libraries. For solid phase libraries, peptides may be synthesized by use of conventional Fmoc chemistry. In the case of conventional Fmoc chemistry, Fmoc-L-Cys-(S$^t$Bu) is coupled to an appropriate resin, via one or more intermediate amino acids, and additional amino acids are thereafter coupled to the L-Cys-(S$^t$Bu) residue. S$^t$Bu may be employed with either L- or D-Cys, and any of a variety of other amino acids, including designer or unnatural amino acids and mimics thereof, characterized by an SH group available for binding to a metal ion, including, but not limited to, 3-mercapto phenylananine and other related 3-mercapto amino acids such as 3-mercapto valine (penicillamine); 2-mercaptoacetic acid; 3-mercaptopropionic acid; 2-mercaptopropionic acid; 3-mercapto-3,3,-dimethyl propionic acid; 3-mercapto,3-methyl propionic acid; 3-mercapto- 3,3-,diethyl propionic acid; 2-mercapto,2-methyl acetic acid; 3-cyclopentamethlene,3-mercaptopropionic acid; 2-cyclopentamethlene,2-mercaptoacetic acid and related amino acids. In all these cases, S-protection can be by S$^t$Bu, S-Acm, Mmt, Npys, S-sulfonate and related groups, as described above.

Metal Ion Complexation to MBD. The complexation of metal ions to the sequences in a library, and specifically to the MBD, is achieved by mixing the sequences with the metal ion. This is conveniently done in solution, with the solution including an appropriate buffer. In one approach, the metal ion is, when mixed with the peptide or peptidomimetic constituents, already in the oxidation state most preferred for complexing to the MBD. Some metal ions are complexed in their most stable oxidation state, such as calcium (II), potassium (I), indium (III), manganese (II), copper (II), zinc (II) and other metals. In other instances, the metal must be reduced to a lower oxidation state in order to be complexed to the MBD. This is true of ferrous, ferric, stannous, stannic, technetiumoxo[V], pertechnetate, rheniumoxo[V], perrhenate and other similar metal ions. Reduction may be performed prior to mixing with the sequences, simultaneously with mixing with the sequences, or subsequent to mixing with the sequences. Any means of reduction of metal ions to the desired oxidation state known to the art may be employ d.

For tetradentate coordination with a metal ion, rhenium is a preferred ion. Solid phase resin bound peptide or peptidomimetic sequences may be labeled with rhenium ion by treatment with the rhenium transfer agent ReOCl$_3$(PPh$_3$)$_2$ in the presence of 1,8-Diazabicyclo[5,4,0] undec-7-ene as a base. The sequences may then be cleaved from the resin. Alternatively, peptide or peptidomimetic sequences in a soluble library may similarly be labeled by treatment with the rhenium transfer agent ReOCl$_3$(PPh$_3$)$_2$ in the presence of 1,8-Diazabicyclo[5,4,0] undec-7-ene as a base. Metal complexation in the presence of 1,8-Diazabicyclo[5,4,0]undec-7-ene (DBU) as a base can conveniently be accomplished at ambient room temperature.

In an alternative method of metal complexation a mild base, such as sodium acetate, can be used. In this case the thiol-containing sequence, either in solution or bound to solid phase, is taken in a suitable solvent, such as DMF, NMP, MeOH, DCM or a mixture thereof, and heated to 60–70° C. with the rhenium transfer agent ReOCl$_3$(PPh$_3$)$_2$ in the presence of sodium acetate for 15 minutes. Similarly, other bases such as triethylamine, ammonium hydroxide and so on, may be employed. According to this invention, MeOH is a preferred choice of solvent for rhenium complexation in the case of S-deprotected peptides in solution. The solvent choice for S-deprotected peptides still attached to the solid phase is guided mainly by considerations of superior solvation (swelling) of the solid phase. DMF and NMP may be employed. Various mixtures of these solvents, also in combination with MeOH, and DCM, CHCl$_3$ and so on, may also be employed to yield optimized complexation results.

In one embodiment of this invention, an S$^t$Bu protected peptide is treated in situ with rhenium transfer agent in the presence of DBU and tributylphosphine to effect S-deprotection and rhenium complexation in one pot. Alternately, complexation of rhenium to the S$^t$Bu protected peptide in the presence of rhenium perrhenate may be accomplished by treatment with Sn[II]Cl$_2$. This reagent effects S-deprotection as well as conversion of ReO$_4$ state to ReO state in situ to cause complexation of the rhenium to the S-deprotected peptide. A preferred procedure in this invention is the use of S$^t$Bu protected peptide with S-deprotection by treatment with tributylphosphine, and metal complexation of the resulting peptide utilizing ReOCl$_3$(PPh$_3$)$_2$ in the presence of DBU at room temperature.

In the libraries of this invention, the MBD forms a reverse turn structure upon complexation with a metal ion, with the library constructed such that side chains of amino acids within the MBD are varied, and similarly amino acids not forming a part of the MBD are also varied. Various compounds in a library of metallopeptides can be obtained by varying the sequence of amino acids in a set of peptides that are all optimized to form a complex of nearly similar geometry when coordinated with a metal ion. This optimization can be obtained, for example, by appropriate positioning of amino acids having high affinity to complex a metal ion. Examples of naturally occurring amino acids with high affinity for metal complexation include Cys and His. A library of such peptides, therefore, would have at least one of these amino acids that is suitably placed in the sequence, with this amino acid being common to all the molecules in the library, with this amino acid thus non-randomized.

A conceptual, generalized view of a solid phase library of metallopeptides that is constructed using local conformational restriction is:

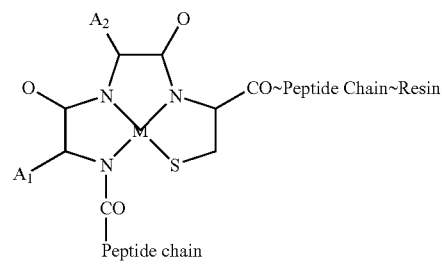

where M is a metal ion, $A_1$ and $A_2$ are amino acid side chains forming parts of the reverse turn structure which is the BBD, and "Peptide Chain" denotes one or more amino acids. A similar library can also be constructed in which the components are soluble, and thus not bound to a resin.

Another embodiment of this invention provides for construction of a library with global conformational restriction. In this embodiment, the MBD can be held constant, and a randomized or selected series of sequences of amino acids or mimetics varied to form the library. This type of library encompasses metallopeptides in which a MBD is an isosteric replacement for a disulfide, lactam, lactone, thioether or thioester moiety in cyclic peptides. In these constructs a set MBD is introduced between two pre-selected ends of a linear peptide or peptidomimetic that contains the randomized or selected series of sequences of amino acids or mimetics under investigation. The general structure of a metallopeptide library of this type is:

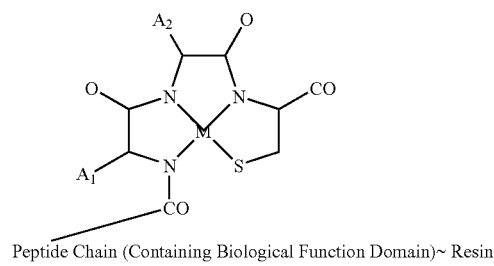

where M is a metal ion and $A_1$ and $A_2$ are structural elements that may provide additional stability to metal complexation, or may modulate biological activity, such as determining the organ of clearance, or altering biodistribution patterns or pharmacokinetics. The "Peptide Chain" sequence may be randomly varied, thereby resulting in a random library, or may be directed in a predetermined fashion, based upon known characteristics of the target molecule.

One illustration of a globally-constrained metallopeptide library is a library of peptides wherein all the individual members of the library include a metal ion-binding domain and the library is directed specifically towards a family of melanocortin receptors. The general formula of this library of peptides, before complexation to a metal ion, is:

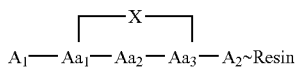

where X is a fixed MBD including a plurality of amino acids, so that all of the valences of the metal ion are satisfied upon complexation of the metal ion with X, $A_1$ and $A_2$ each comprise from 0 to about 20 amino acids, and $Aa_1$, $Aa_2$ and $Aa_3$ each comprise one or more amino acids connected to X through an amide, thioether, thioester, ester, carbamate, or urethane bond, wherein each of $Aa_1$, $Aa_2$ and $Aa_3$ is varied. In this example, the MBD may include an OSPG. Other thiols in the sequence may optionally include S-protecting groups that are not orthogonal, such that the OSPG may be removed without removal of other S-protecting groups in the sequence.

For solid phase libraries the peptide constructs are attached to a resin, and the resin is omitted for soluble libraries. The functional equivalent of each these peptide libraries may also be obtained through the development of a library of non-amino acid building blocks so as to result in structural mimics of these peptides. The peptide bonds may be replaced by pseudopeptide bonds, such as thioamides, thioethers, substituted amines, carbanate, urethane, aliphatic moieties, and functionally similar constructs.

A peptide library is first assembled according to the sequence specification and degeneration, as described above, by well-known methods of peptide synthesis. These libraries can be synthesized as discreet, spatially addressable compounds in parallel synthesis, using split synthesis approaches, or by deconvolution techniques of soluble libraries. Using similar methods, a pseudopeptide, peptidomimetic or non-peptide library can be obtained. The non-peptide libraries may also optionally incorporate one of various tagging approaches that are well known to those skilled in the art. Both solid-phase and soluble libraries can be obtained in this manner. The entire library is then reacted with an appropriate metal-complexing agent to obtain the corresponding metal-coordinated library, comprising a similar class of predetermined structures. For example, to complex a peptide library with rheniumoxo metal ion, the peptide library can be treated with $Re(O)Cl_3(PPh_3)_2$ in the presence of sodium acetate. This procedure results in quantitative complexation of ReO with the peptide. In order to complex Zn, Co, Mn, Fe or Cu ions, the peptide library is treated with chloride or other suitable salts of these metal ions to yield the library of corresponding metal ions. Essentially, a variety of metal ions can be used to construct different metallopeptide libraries. One limiting factor in selection of the appropriate metal ion is the relative stability of a particular metal-peptide complex, related in large part to the metal-peptide binding constant or constants. It is well known in the art that some metal-peptide constructs are stable only within specified pH or other special conditions, or are easily oxidized in air. Some peptide-metal ion complexes, such as those with ReO, are stable in pure form and can be isolated and stored under normal storage conditions for a long period of time.

A metallopeptide library constructed according to this invention can be screened to identify one or more receptor-binding or pharmacologically-active melanocortin receptor-specific candidates by various techniques that have been reported in the prior art. Both soluble and solid phase libraries may be directly employed in these assays. These techniques include direct target binding approaches as described by Lam and coworkers (Lam K S et al: *Nature* 354:82–84, 1991; Lam K S et al: *Nature* 360:768, 1992), deconvolution and iterative re-synthesis approaches (Houghten R A et al: *Proc Natl Acad Sci USA* 82:5131–5135, 1985; Berg et al: *J Am Chem Soc* 111: 8024–8026, 1989; Dooley C T et al: *Science* 266:2019–2022, 1994; Blondelle S E: *Antimicrob Agents Chemother* 38:2280–2286, 1994; Panilla C: *Biopolymers* 37:221–240, 1995), approaches using orthogonal pools of two co-synthesized libraries according to Tartar and coworkers (Deprez B et al: *J Am Chem Soc* 117: 5405–5406, 1995), positional scanning methods devised by Houghton and coworkers that eliminate iterative re-synthesis (Dooley C T et al: *Life Sci* 52:1509–1517, 1993; Pinilla C et al: *Biotechniques* 13:901–905, 1992; Pinilla C et al: *Drug Dev Res* 33:133–145, 1992), and a combination of the positional scanning method with split synthesis methods (Erb E et al: *Proc Natl Acad Sci USA*, 91:11422–11426,1994).

Among these techniques, the deconvolution and iterative resynthesis approach, the approach involving orthogonal pools of two co-synthesized libraries, and the positional scanning method may be directly applied to soluble metallopeptide libraries to elucidate the structure of a "hit," or peptide identified as a receptor-binding or pharmacologically-active candidate in the screening process. For solid phase libraries, other than spatially addressable parallel synthesis libraries, the structure of hits can be directly determined by various strategies well known to those skilled in the art. These include direct mass spectrometric analysis of compounds covalently bound to solid phase matrix of particles by the use of matrix-assisted laser desorption/ionization (MALDI) techniques (Siuzdak G et al: *Bioorg Med Chem Lett* 6:979, 1996; Brown BB et al: *Molecular Diversity* 1:4–12, 1995). The technique of creating a series of partially end-capped compounds at each of the synthetic steps during library assembly also helps in unambiguous identification by mass spectrometry (Youngquist R S et al: *J Am Chem Soc,* 117:3900–3906, 1995; Youngquist RS et al: *Rapid Commun Mass Spectr* 8:77–81, 1994). In addition to these analytical techniques, various encoding strategies that have been devised for structure elucidation in organic molecule-based libraries, including non-peptide and non-nucleotide libraries, may be utilized. Various encoding strategies, such as DNA encoding, peptide encoding, haloaromatic tag encoding, and encoding based on radiofrequency transponders, are now well known in the art and can be used directly in combination with metallopeptide libraries. These tagging strategies require the incorporation of the tags during the course of synthesis of libraries, which can be accomplished during the construction of a metallopeptide libraries, since metal complexation is a final, post-synthesis step.

Structural Diversity of Melanocortin Receptor-Specific Library Members. Examples of some of the molecular templates which may be employed in this invention are shown below for tetradentate metal ion complexation. In general, these molecular templates define groups of metallopeptides of this invention which, by substitution as provided, give rise to libraries of metallopeptides for use in determining melanocortin receptor-specific compounds, which may be either agonist or antagonist compounds. The templates are provided without the metal ion, it being understood that the compounds exhibit enhanced specificity for melanocortin receptors only upon metal ion complexation.

$R_1$-Lll-Aaa-Bbb-C-$R_2$     Template 1 and $R_1$-Bbb-Aaa-Ccc-$R_2$     Template 2

Where $R_1$ is any functionality that potentiates the intrinsic activity of the remainder of the molecule, including but not limited to providing an auxiliary or secondary receptor contact. Any of a variety of amino acids and non-peptide groups may be employed, including an amino acid chain from one to about four neutral or charged L- or D-configuration amino acid residues. If $R_1$ is a non-peptide group, it may be a linear or branched alkyl, aryl, alkene, alkenyl or aralkyl chain.

Where Aaa is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Aaa provides an N (nitrogen atom) for metal ion complexation.

Where Bbb is an L- or D-configuration amino acid with an aromatic side chain. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), or Tyr(BzlCl$_2$), and derivatives, analogs or homologs thereof. The aromatic ring in Bbb may be functionalized with halogen, alkyl or aryl groups. Bbb provides an N for metal ion complexation.

Where Ccc is an amino acid that provides both an N, from the alpha amino group, and an S (sulfur atom), from a side chain group, for metal ion complexation. Preferred amino acids include L- or D-configuration Cys, Pen and Hcys.

Where Lll is a D-configuration amino acid with an aromatic side chain. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), or Tyr(BzlCl$_2$), and derivatives, analogs or homologs thereof. The aromatic ring in Ll may be functionalized with halogen, alkyl or aryl groups. Lll does not provide an N for metal ion complexation.

Where $R_2$ is an amino acid with an aromatic side chain. Preferred amino acids include L- or D-configuration Phe, Trp, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The C-terminus may be free or amidated. $R_2$ may also be the corresponding des-carboxyl amino acid of any of the foregoing. Alternatively, $R_2$ may be eliminated.

Figure 2:
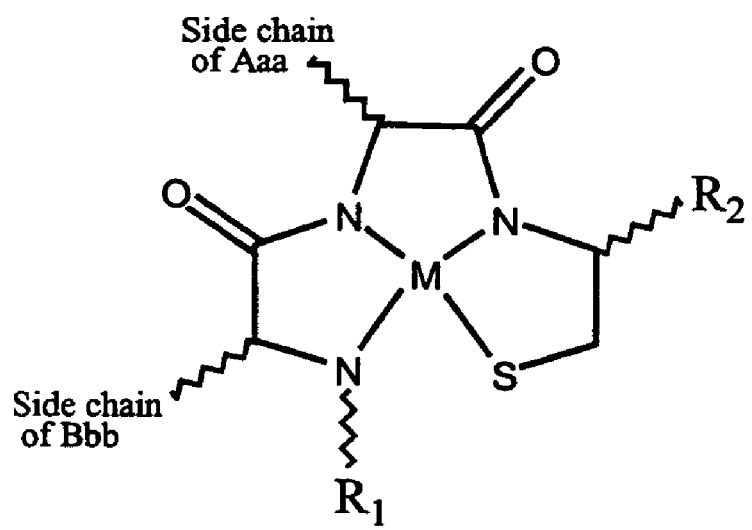
FIG. 2 is a molecular structure for Template 2.

FIG. 1 depicts the structure of Template 1, and FIG. 2 depicts the structure of Template 2, in both cases showing coordination with a tetradenate coordination sphere metal ion, resulting in an $N_3$ μl metal ion bond.

$R_1$-Ddd-Bbb-Aaa-$R_3$     Template 3

Where $R_1$, Bbb and Aaa are as described above.

Where Ddd is an amino acid that provides an S, from a side chain group, for metal ion complexation. Preferred amino acids include L- or D-configuration Cys, Pen and Hcys.

Where $R_3$ is an amino acid with an aromatic side chain that provides an N for metal ion complexation. Preferred amino acids include L- or D-configuration Phe, Trp, Phe (4'Cl), Phe(3',4' Di-Cl), Phe(4'-nitro), Phe(4'-methyl), Phe (4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids. The C-terminus may be free or amidated. $R_3$ may also be the corresponding des-carboxyl amino acid of any of the foregoing.

Figure 3:
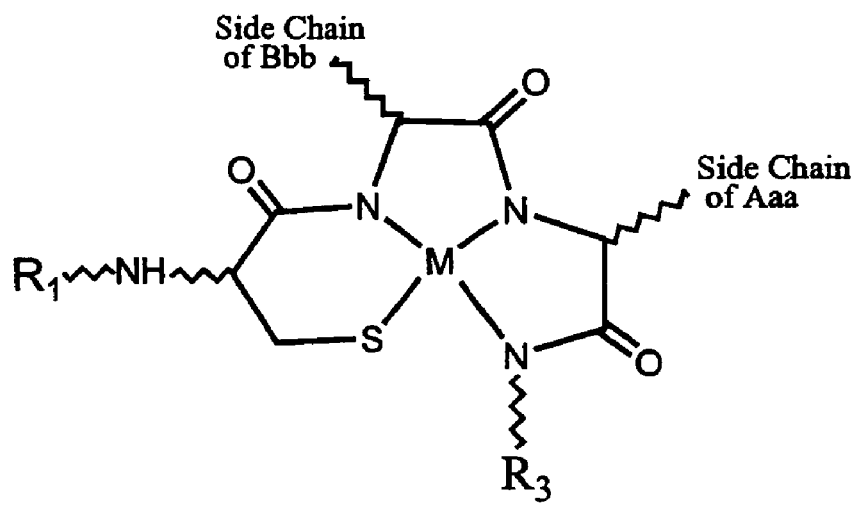
FIG. 3 is a molecular structure for Template 3.

FIG. 3 depicts the structure of Template 3, showing coordination with a tetradenate coordination sphere metal ion, resulting in an $N_3S_1$ metal ion bond.

$R_4$-Eee-Bbb-Ccc-$R_2$     Template 4

Where $R_2$, Bbb and Ccc are as described above.

Where $R_4$ is a functionality that provides a cationic center. Preferred amino acids include L- or D-configuration Lys, Arg, Orn, Dpr or Dbu, and derivatives, analogs or homologs thereof, including both natural and synthetic amino acids. The N-terminus of the amino acid may be functionalized with any of a variety of neutral amino acid and non-peptide groups, including linear or branched alkyl, aryl, alkene, alkenyl or aralkyl chains.

Where Eee is an uncharged L- or D-configuration amino acid that provides an N for metal ion complexation. Preferred amino acids include Gly and L-configuration Ala, Nle, Leu, Val, Phe or Trp, and derivatives, analogs or homologs thereof, including both natural and synthetic amino acids. In a preferred embodiment, Eee isn an amino acid with an aliphatic side chain.

Figure 4:
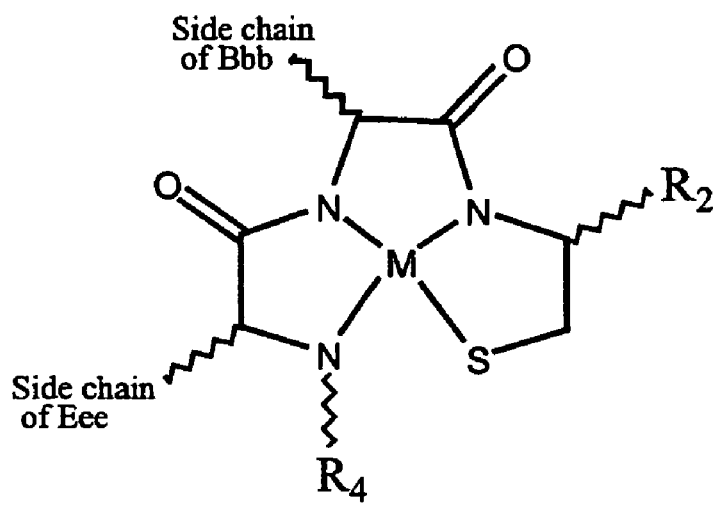
FIG. 4 is a molecular structure for Template 4.

FIG. 4 depicts the structure of Template 4, showing coordination with a tetradenate coordination sphere metal ion, resulting in an $N_3S_1$ metal ion bond.

$R_1$-Fff-Aaa-Ggg-Ccc-$R_5$     Template 5

Where $R_1$, Aaa and Ccc are as described above.

Where Fff is an L- or D-configuration aromatic amino acid. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), Tyr(BzlCl$_2$), Tic, Tiq or Tca, and derivatives, analogs or homologs thereof, including both natural and synthetic amino acids. The aromatic ring in Fff may be substituted with halogen, alkyl or aryl groups. Fff does not provide an N for metal ion complexation.

Where Ggg is an L- or D-configuration aromatic amino acid. Preferred amino acids include L-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl) or Tyr (BzlCl$_2$), and derivatives, analogs or homologs thereof, including both natural and synthetic amino acids. The aromatic ring in Ggg may be substituted with halogen, alkyl or aryl groups. Ggg provides an N for metal ion complexation.

Where R₅ is preferably an amide, substituted amide, ester or carboxylate group. R₅ may also be and L- or D-configuration amino acid or amino acid amide, including an aromatic, aliphatic, neutral or charged amino acid.

Figure 5:
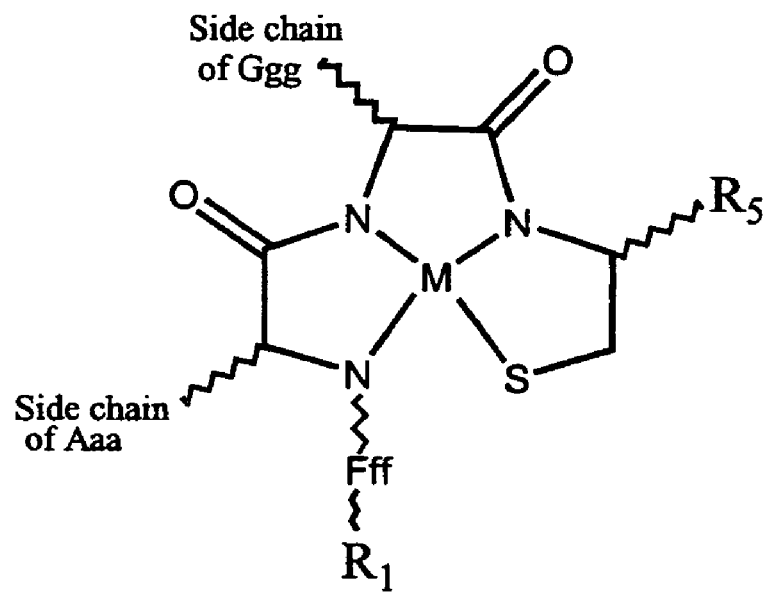
FIG. 5 is a molecular structure for Template 5.

FIG. 5 depicts the structure of Template 5, showing coordination with a tetradenate coordination sphere metal ion, resulting in an $N_3S_1$ metal ion bond.

R₁-Hhh-Aaa-Bbb-Ccc-R₅     Template 6

Where R₁, Aaa, Bbb, Ccc and R₂ are as described above.

Where Hhh is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Hhh does not provide an N for metal ion complexation.

Figure 6:
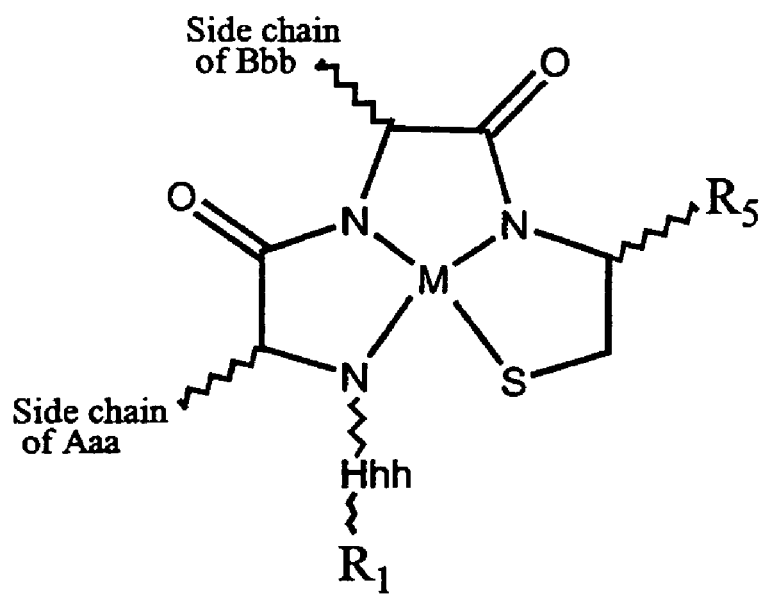
FIG. 6 is a molecular structure for Template 6.

FIG. 6 depicts the structure of Template 6, showing coordination with a tetradenate coordination sphere metal ion, resulting in an $N_3S_1$ metal ion bond.

R₁-Iii-Iii-Ccc-Jjj-Kkk-R₂     Template 7

Where R₁, Ccc and R₂ are as described above.

Where Iii is an L- or D-configuration amino acid that provides an N for metal ion complexation. Preferred amino acids includes Ala, Gly, Nle, Val, Leu, Ile, His, Lys, or Arg, and derivatives, analogs or homologs thereof, including both natural and synthetic amino acids.

Where Jjj is an L- or D-configuration amino acid with an aromatic side chain. Preferred amino acids include D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), or Tyr(BzlCl₂), and derivatives, analogs or homologs thereof. The aromatic ring in Jjj may be functionalized with halogens, alkyl or aryl groups. Jjj does not provide an N for metal ion complexation.

Where Kkk is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Aaa does not provide an N for metal ion complexation.

Figure 7:
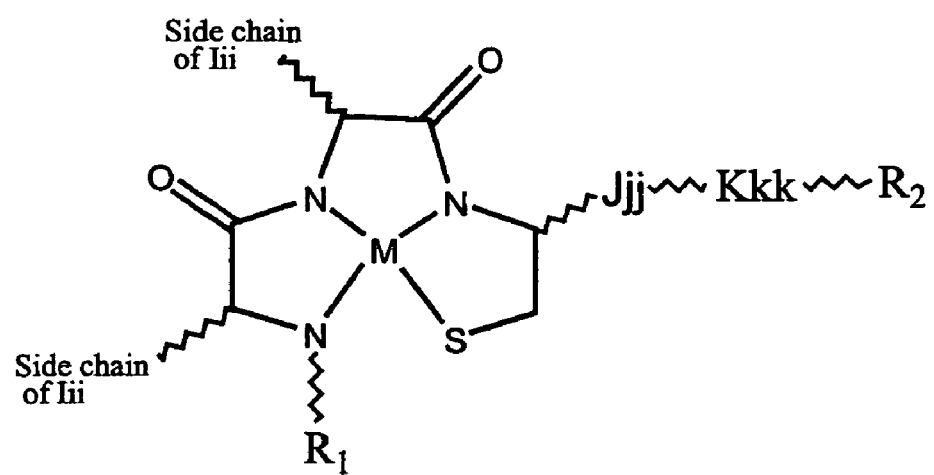
FIG. 7 is a molecular structure for Template 7.

FIG. 7 depicts the structure of Template 7, showing coordination with a tetradenate coordination sphere metal ion, resulting in an $N_3S_1$ metal ion bond.

The foregoing templates may be employed with tetradentate coordination sphere metal ions, such as various forms of technetium and rhenium. Corresponding templates may be constructed for use with metal ions of other coordination spheres.

Where Kkk is an L- or D-configuration cationic amino acid with a positively charged side chain. Preferred amino acids include L-configuration Lys, Arg, Orn, Dpr or Dbu, and derivatives, analogs or homologs thereof, including both natural and synthetic amino acids. Aaa does not provide an N for metal ion complexation.

FIG. 7 depicts the structure of Template 7, showing coordination with a tetradenate coordination sphere metal ion, resulting in an $N_3S_1$ metal ion bond.

The foregoing templates may be employed with tetradentate coordination sphere metal ions, such as various forms of technetium and rhenium. Corresponding templates may be constructed for use with metal ions of other coordination spheres.

Representative Peptides of this Invention. Representative peptides of this invention were made using library and synthesis methods described herein, and selected peptides were tested using a binding assay. Table 1 sets forth peptides of this invention, and the results of competitive inhibition binding assays. The peptides were synthesized using conventional peptide synthesis methods, and were complexed with rhenium using the methods described herein.

The competitive inhibition binding assay was conducted using membranes prepared from hMC4-R and B-16 mouse melanoma cells (containing MC1-R) using 0.4 nM $^{125}$I-NDP-alpha-MSH (New England Nuclear, Boston, Mass., USA) in 50 mM HEPES buffer containing 1 mM MgCl₂, 2 mM CaCl₂, and 5 mM KCl, at pH 7.2. The assay tube also contained a chosen concentration of the test peptide of this invention, complexed to a rhenium metal ion as indicated, for determining its efficacy in inhibiting the binding of $^{125}$I-NDP-alpha-MSH to its receptor. Non-specific binding was measured by complete inhibition of binding of $^{125}$I-NDP-alpha-MSH in the assay with the presence of 1 μM alpha-MSH. Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM alpha-MSH. The cpm obtained in presence of test compounds were normalized with respect to 100% specific binding to determine the percent inhibition of $^{125}$I-NDP-alpha MSH binding. Each assay was conducted in triplicate and the actual mean valves are described in Table 1. Negative numbers in Table 1 under "% Inhibition" result from experimental variance, and are indicative of no inhibition; similarly, values over 100% also result from experimental variance, and are indicative of complete inhibition.

TABLE 1

Melanocortin Receptor Screening Results: Receptor Binding Assay

| Compound ID | Metal ion/ Linear peptide | Sequence Structure | Conc. Cut off (μM) | % Inhibition MC4-R | MC1-R (B-16) |
|---|---|---|---|---|---|
| PL-808 | ReO[V] | Ac-L-His-L-Trp-L-Cys-L-Trp-NH₂ (SEQ ID NO: 3) | 1 | 0 | −3 |
| PL-809 | ReO[V] | Ac-L-His-L-Hphe-L-Cys-L-Trp-NH₂ (SEQ ID NO: 4) | 1 | 0 | −4 |
| PL-810 | ReO[V] | Ac-L-His-L-Nal 2-L-Cys-L-Trp-NH₂ (SEQ ID NO: 5) | 1 | −1 | −2 |
| PL-811 | ReO[V] | Ac-L-His-L-Phg-L-Cys-L-Trp-NH₂ (SEQ ID NO: 6) | 1 | 0 | −5 |
| PL-812 | Linear | Ac-L-His-L-Phe-L-Cys-L-Trp-NH₂ (SEQ ID NO: 7) | 10 | 29 | 54 |
| PL-813 | Linear | Ac-L-His-D-Phe-L-Cys-L-Trp-NH₂ | 10 | 8 | 91 |

TABLE 1-continued

Melanocortin Receptor Screening Results: Receptor Binding Assay

| Compound ID | Metal ion/ Linear peptide | Sequence Structure | Conc. Cut off (μM) | % Inhibition MC4-R | MC1-R (B-16) |
|---|---|---|---|---|---|
| PL-814 | ReO[V] | Ac-L-His-L-Phe-L-Cys-L-Trp-NH$_2$ (SEQ ID NO: 7) | 1 | 0 | −4 |
| PL-815 | ReO[V] | Ac-L-His-D-Phe-L-Arg-L-Cys-L-Trp-NH$_2$ | 10 | 7 | 93 |
| PL-816 | ReO[V] | Ac-L-His-D-Phe-L-Cys-L-Trp-NH$_2$ | 10 | 28 | 70 |
| PL-836 | ReO[V] | Ac-L-His-L-Phe-D-Arg-L-Cys-L-Trp-NH$_2$ | 10 | 26 | 78 |
| PL-837 | ReO[V] | Ac-L-His-D-Phe-D-Arg-L-Cys-L-Trp-NH$_2$ | 10 | 0 | 54 |
| PL-838 | ReO[V] | Ac-L-His-L-Phe-L-Arg-L-Cys-L-Trp-NH$_2$ (SEQ ID NO: 8) | 10 | 0 | 35 |
| PL-839 | ReO[V] | Ac-L-His-L-Phe-L-Trp-L-Cys-NH$_2$ (SEQ ID NO: 9) | 10 | 9 | 12 |
| PL-840 | ReO[V] | Ac-L-His-L-Phe-D-Trp-L-Cys-NH$_2$ | 10 | 10 | 8 |
| PL-841 | ReO[V] | Ac-L-His-D-Phe-D-Trp-L-Cys-NH$_2$ | 10 | 0 | 19 |
| PL-842 | ReO[V] | Ac-L-His-D-Phe-L-Trp-L-Cys-NH$_2$ | 10 | 2 | 4 |
| PL-843 | ReO[V] | Ac-D-Phe-Gly-L-Cys-L-Trp-NH$_2$ | 10 | 1 | 10 |
| PL-844 | ReO[V] | Ac-L-Phe-Gly-L-Cys-L-Trp-NH$_2$ (SEQ ID NO: 10) | 10 | 2 | 10 |
| PL-845 | ReO[V] | Ac-D-Phe-L-His-Gly-L-Cys-L-Trp-NH$_2$ | 10 | 0 | 5 |
| PL-846 | ReO[V] | Ac-L-Phe-D-His-Gly-L-Cys-L-Trp-NH$_2$ | 10 | 0 | 2 |
| PL-847 | ReO[V] | Ac-L-Phe-L-His-Gly-L-Cys-L-Trp-NH$_2$ (SEQ ID NO: 11) | 10 | 6 | −6 |
| PL-848 | ReO[V] | Ac-D-Phe-D-His-Gly-L-Cys-L-Trp-NH$_2$ | 10 | 10 | 19 |
| PL-989 | ReO[V] | Bz-D-Tyr-L-Nal-L-Cys-L-Phe-NH$_2$ | 10 | 11 | 35 |
| PL-997 | ReO[V] | Bz-D-Nal-L-Tyr-L-Cys-L-Phe-NH$_2$ | 10 | 36 | 6 |
| PL-1073 | ReO[V] | Ac-L-Ala-L-Tle-L-Cys-L-Trp-NH$_2$ (SEQ ID NO: 12) | 1 | 13 | −6 |
| PL-1089 | ReO[V] | Ac-L-Ala-L-pF-Phe-L-Cys-L-Trp-NH$_2$ (SEQ ID NO: 13) | 10 | 10 | 0 |
| PL-1090 | ReO[V] | Ac-L-Ala-L-Tyr(3',5' di-I, 4'-Ac)-L-Cys-L-Trp-NH$_2$ (SEQ ID NO: 14) | 1 | 10 | 2 |
| PL-1091 | ReO[V] | BAla-Gly-L-Cys(Bzl)-L-Cys-L-Trp-NH$_2$ (SEQ ID NO: 15) | 1 | 13 | −1 |
| PL-1092 | ReO[V] | BAla-Gly-L-Lys(TFA)-L-Cys-L-Trp-NH$_2$ (SEQ ID NO: 16) | 1 | 4 | 4 |
| PL-1093 | ReO[V] | BAla-Gly-L-Phe(2,4-di Cl)-L-Cys-L-Trp-NH$_2$ (SEQ ID NO: 17) | 1 | 2 | 2 |
| PL-1094 | ReO[V] | BAla-Gly-L-Phe(2-Cl)-L-Cys-L-Trp-NH$_2$ (SEQ ID NO: 18) | 10 | 19 | 57 |
| PL-1095 | ReO[V] | BAla-Gly-L-Lys(Z)-L-Cys-L-Trp-NH$_2$ (SEQ ID NO: 19) | 10 | 8 | 3 |
| PL-1096 | ReO[V] | BAla-Gly-L-Leu-L-Cys-L-Trp-NH$_2$ (SEQ ID NO: 20) | 10 | 12 | 6 |
| PL-1102 | ReO[V] | BAla-Gly-D-Nal 2-L-Cys-L-Trp-NH$_2$ | 10 | 60 | 9 |
| PL-1103 | ReO[V] | BAla-Gly-D-Phg-L-Cys-L-Trp-NH$_2$ | 10 | 12 | −3 |
| PL-1109 | ReO[V] | L-Lys-L-His-D-Phe-L-Cys-L-Trp-NH$_2$ | 10 | 37 | 73 |
| PL-1110 | ReO[V] | L-Lys-L-His-L-Phe-L-Cys-L-Trp-NH$_2$ (SEQ ID NO: 21) | 10 | 36 | 11 |
| PL-1111 | ReO[V] | L-His-D-Phe-L-Cys-L-Trp-NH$_2$ | 10 | 0 | 0 |
| PL-1112 | ReO[V] | L-His-L-Phe-L-Cys-L-Trp-NH$_2$ (SEQ ID NO: 7) | 10 | 8 | 0 |
| PL-1113 | ReO[V] | BAla-L-His-D-Phe-L-Cys-L-Trp-NH$_2$ | 10 | 31 | 82 |
| PL-1114 | ReO[V] | BAla-L-His-L-Phe-L-Cys-L-Trp-NH$_2$ (SEQ ID NO: 22) | 10 | 10 | 2 |
| PL-1140 | ReO[V] | Ac-D-Phe-Arg-L-Cys-L-Phe-NH$_2$ | 10 | 12 | 62 |
| PL-1141 | ReO[V] | Ac-D-Phe-Arg-L-Cys-L-Trp-NH$_2$ | 10 | 11 | 57 |
| PL-1144 | ReO[V] | Ac-L-Nle-L-Ala-L-His-D-Phe-L-Arg-L-Cys-L-Phe-NH$_2$ | 1 | 14 | 99 |
| PL-1145 | ReO[V] | Ac-L-Nle-L-Ala-L-His-D-Phe-L-Arg-L-Cys-L-Trp-NH$_2$ | 1 | 17 | 96 |
| PL-1146 | ReO[V] | Ac-D-Phe-Gly-L-Cys-L-Phe-NH$_2$ | 10 | 9 | 39 |
| PL-1147 | ReO[V] | Ac-D-Pip-Gly-L-Cys-L-Phe-NH$_2$ | 10 | 12 | 40 |
| PL-1156 | ReO[V] | Ac-D-Phe-L-Tle-L-Cys-L-Trp-NH$_2$ | 10 | 14 | −19 |
| PL-1157 | ReO[V] | Ac-L-Nle-L-Arg-Gly-D-Nal 2-L-Cys-L-Trp-NH$_2$ | 10 | 92 | 53 |
| PL-1158 | ReO[V] | BAla-L-Ala-D-Nal 2-L-Cys-L-Trp-NH$_2$ | 10 | 62 | 0 |
| PL-1159 | ReO[V] | BAla-L-His-D-Nal 2-L-Cys-L-Trp-NH$_2$ | 10 | 63 | 67 |
| PL-1160 | ReO[V] | BAla-L-Phe-D-Nal 2-L-Cys-L-Trp-NH$_2$ | 10 | 66 | 1 |
| PL-1161 | ReO[V] | BAla-L-Nal 2-D-Nal 2-L-Cys-L-Trp-NH$_2$ | 10 | 64 | 3 |
| PL-1162 | ReO[V] | Heptanoyl-L-Arg-Gly-D-Nal 2-L-Cys-L-Trp-NH$_2$ | 10 | 79 | 64 |
| PL-1163 | ReO[V] | BAla-D-Ala-D-Nal 2-L-Cys-L-Trp-NH$_2$ | 10 | 51 | 4 |
| PL-1164 | ReO[V] | BAla-D-His-D-Nal 2-L-Cys-L-Trp-NH$_2$ | 10 | 42 | 2 |
| PL-1165 | ReO[V] | BAla-D-Phe-D-Nal 2-L-Cys-L-Trp-NH$_2$ | 10 | 43 | 7 |
| PL-1166 | ReO[V] | BAla-D-Nal 2-D-Nal 2-L-Cys-L-Trp-NH$_2$ | 10 | 44 | 5 |
| PL-1167 | ReO[V] | Abu-Gly-D-Nal 2-L-Cys-L-Trp-NH$_2$ | 10 | 31 | −1 |
| PL-1168 | ReO[V] | Axh-Gly-D-Nal 2-L-Cys-L-Trp-NH$_2$ | 10 | 41 | −2 |
| PL-1169 | ReO[V] | 8-Aoc-Gly-D-Nal 2-L-Cys-L-Trp-NH$_2$ | 10 | 41 | −3 |
| PL-1170 | ReO[V] | 11-Aun-Gly-D-Nal 2-L-Cys-L-Trp-NH$_2$ | 10 | 27 | 9 |
| PL-1171 | ReO[V] | 12-Ado-Gly-D-Nal 2-L-Cys-L-Trp-NH$_2$ | 10 | 29 | −5 |
| PL-1172 | ReO[V] | Ac-L-Arg-Gly-D-Nal 2-L-Cys-L-Trp-NH$_2$ | 10 | 58 | −7 |
| PL-1173 | ReO[V] | Ac-L-Lys-Gly-D-Nal 2-L-Cys-L-Trp-NH$_2$ | 10 | 41 | −2 |
| PL-1174 | ReO[V] | Ac-L-Orn-Gly-D-Nal 2-L-Cys-L-Trp-NH$_2$ | 10 | 53 | −2 |
| PL-1175 | ReO[V] | Ac-L-Nle-L-Arg-Gly-D-Nal 2-L-Cys-L-Trp-NH$_2$ | 10 | 96 | 88 |
| PL-1176 | ReO[V] | 7-Ahept-Gly-D-Nal 2-L-Cys-L-Trp-NH$_2$ | 10 | 40 | −8 |
| PL-1177 | ReO[V] | B-Gpa-Gly-D-Nal 2-L-Cys-L-Trp-NH$_2$ | 10 | 48 | −6 |
| PL-1178 | ReO[V] | Ac-L-Nle-L-Ala-L-His-D-HPhe-L-Arg-L-Cys-L-Trp-NH$_2$ | 1 | 4 | 51 |
| PL-1179 | ReO[V] | Ac-L-Nle-L-Ala-L-His-D-His-L-Arg-L-Cys-L-Trp-NH$_2$ | 1 | 21 | −5 |
| PL-1180 | ReO[V] | Ac-L-Nle-L-Ala-L-His-D-Trp-L-Arg-L-Cys-L-Trp-NH$_2$ | 1 | 24 | 86 |
| PL-1181 | ReO[V] | Ac-L-Nle-L-Ala-L-His-D-Tyr-L-Arg-L-Cys-L-Trp-NH$_2$ | 1 | 27 | 86 |
| PL-1183 | ReO[V] | Ac-L-Nle-L-Ala-L-Arg-D-Nal 2-L-Arg-L-Cys-L-Trp-NH$_2$ | 1 | 82 | 96 |
| PL-1184 | ReO[V] | Ac-L-Nle-L-Ala-L-Tyr-D-Nal 2-L-Arg-L-Cys-L-Trp-NH$_2$ | 1 | 58 | 36 |
| PL-1185 | ReO[V] | Ac-L-Nle-L-Ala-L-Phe-D-Nal 2-L-Arg-L-Cys-L-Trp-NH$_2$ | 1 | 35 | 52 |
| PL-1186 | ReO[V] | Ac-L-Nle-L-Ala-L-Trp-D-Nal 2-L-Arg-L-Cys-L-Trp-NH$_2$ | 1 | 35 | 17 |
| PL-1187 | ReO[V] | Ac-L-Ala-L-His-D-Nal 2-L-Arg-L-Cys-L-Trp-NH$_2$ | 1 | 48 | 58 |

TABLE 1-continued

Melanocortin Receptor Screening Results: Receptor Binding Assay

| Compound ID | Metal ion/ Linear peptide | Sequence Structure | Conc. Cut off (µM) | % Inhibition MC4-R | MC1-R (B-16) |
|---|---|---|---|---|---|
| PL-1188 | ReO[V] | Ac-L-Nle-L-Ala-D-Trp-D-Nal 2-L-Arg-L-Cys-L-Trp-NH$_2$ | 1 | 38 | −12 |
| PL-1189 | ReO[V] | Ac-L-Nle-L-Ala-D-Phe-D-Nal 2-L-Arg-L-Cys-L-Trp-NH$_2$ | 1 | 36 | −15 |
| PL-1190 | ReO[V] | Ac-L-Nle-L-Ala-D-His-D-Nal 2-L-Arg-L-Cys-L-Trp-NH$_2$ | 1 | 31 | 17 |
| PL-1191 | ReO[V] | Ac-L-Nle-L-Ala-D-Arg-D-Nal 2-L-Arg-L-Cys-L-Trp-NH$_2$ | 1 | 41 | 38 |
| PL-1192 | ReO[V] | Ac-L-Nle-L-Ala-D-Tyr-D-Nal 2-L-Arg-L-Cys-L-Tyr-NH$_2$ | 1 | 26 | −5 |
| PL-1193 | ReO[V] | Ac-L-Glu-L-Ala-D-Nal 2-L-Arg-L-Cys-L-Trp-NH$_2$ | 1 | 29 | 51 |
| PL-1194 | ReO[V] | HOOC-(CH$_2$)$_3$-CO-L-His-D-Nal 2-L-Arg-L-Cys-L-Trp-NH$_2$ | 1 | −3 | 23 |
| PL-1195 | ReO[V] | Ac-L-Ala-L-Glu-L-His-D-Nal 2-L-Arg-L-Cys-L-Trp-NH$_2$ | 1 | 9 | 45 |
| PL-1196 | ReO[V] | Ac-L-Nle-L-Glu-L-His-D-Nal 2-L-Arg-L-Cys-L-Trp-NH$_2$ | 1 | 31 | 89 |
| PL-1197 | ReO[V] | Ac-L-Glu-L-His-D-Nal 2-L-Arg-L-Cys-L-Trp-NH$_2$ | 1 | 9 | 44 |
| PL-1198 | ReO[V] | Ac-L-Glu-L-His-D-Nal 2-L-Cys-L-Arg-NH$_2$ | 1 | 4 | −5 |
| PL-1199 | ReO[V] | Ac-L-Glu-L-His-L-Cys-D-Nal 2-L-Arg-NH$_2$ | 1 | 1 | −11 |
| PL-1200 | ReO[V] | Ac-L-Glu-L-His-D-Nal 2-L-Cys-L-Arg-L-Trp-NH$_2$ | 1 | 10 | 8 |
| PL-1201 | ReO[V] | Ac-L-Glu-L-His-L-Cys-D-Nal 2-L-Arg-L-Trp-NH$_2$ | 1 | 65 | −7 |
| PL-1202 | ReO[V] | Ac-L-Nle-L-Ala-D-Trp-D-Phe-L-Arg-L-Cys-L-Trp-NH$_2$ | 1 | 17 | 10 |
| PL-1203 | ReO[V] | Ac-L-Nle-L-Ala-D-Nal 2-D-Nal 2-L-Arg-L-Cys-L-Trp-NH$_2$ | 1 | 35 | 4 |
| PL-1204 | ReO[V] | Ac-L-Nle-L-Ala-D-Nal 1-D-Nal 2-L-Arg-L-Cys-L-Trp-NH$_2$ | 1 | 32 | 0 |
| PL-1205 | ReO[V] | Ac-L-Nle-L-Ala-Gly-D-Nal 2-L-Arg-L-Cys-L-Trp-NH$_2$ | 1 | 54 | 60 |
| PL-1206 | ReO[V] | Heptanoyl-D-Trp-D-Nal 2-L-Arg-L-Cys-L-Trp-NH$_2$ | 1 | 17 | 0 |
| PL-1207 | ReO[V] | Ac-L-Ala-L-His-D-Nal 2-L-Cys-D-Nal 2-L-Arg-L-Trp-NH$_2$ | 1 | 84 | 26 |
| PL-1209 | ReO[V] | Ac-L-Nal 2-L-His-D-Nal 2-L-Cys-D-Nal 2-L-Arg-L-Trp-NH$_2$ | 1 | 77 | 1 |
| PL-1210 | ReO[V] | Ac-D-Nal 2-L-His-D-Nal 2-L-Cys-D-Nal 2-L-Arg-L-Trp-NH$_2$ | 1 | 71 | 0 |
| PL-1211 | ReO[V] | Heptanoyl-L-Glu-L-His-D-Nal 2-L-Cys-D-Nal 2-L-Arg-L-Trp-NH$_2$ | 1 | 67 | 26 |
| PL-1212 | ReO[V] | Ac-L-Glu-D-Trp-D-Nal 2-L-Cys-D-Nal 2-L-Arg-L-Trp-NH$_2$ | 1 | 80 | 0 |
| PL-1213 | ReO[V] | Ac-D-Trp-D-Arg-L-Nal 2-D-Nal 2-L-Cys-D-Nal 2-L-Arg-L-Trp-NH$_2$ | 1 | 94 | 34 |
| PL-1214 | ReO[V] | Heptanoyl-L-Arg-Gly-D-Nal 2-D-Nal 2-L-Cys-D-Nal 2-L-Arg-L-Trp-NH$_2$ | 1 | 78 | 47 |
| PL-1215 | ReO[V] | Gly-Gly-D-Nal 2-L-Cys-L-Trp-NH$_2$ | 10 | 31 | 20 |
| PL-1216 | ReO[V] | L-Lys-Gly-D-Nal 2-L-Cys-L-Trp-NH$_2$ | 10 | 47 | 0 |
| PL-1217 | ReO[V] | L-Lys(Z)-Gly-D-Nal 2-L-Cys-L-Trp-NH$_2$ | 10 | 52 | 24 |
| PL-1218 | ReO[V] | BAla-L-Arg(Tos)-D-Nal 2-L-Cys-L-Trp-NH$_2$ | 10 | 57 | 1 |
| PL-1220 | ReO[V] | BAla-L-Tle-D-Nal 2-L-Cys-L-Trp-NH$_2$ | 10 | 69 | 30 |
| PL-1221 | ReO[V] | BAla-L-Tyr(BzlDiCl 2,6)-D-Nal 2-L-Cys-L-Trp-NH$_2$ | 10 | 35 | 37 |
| PL-1222 | ReO[V] | BAla-Gly-D-Phe-L-CysL-Trp-NH$_2$ | 10 | 27 | 9 |
| PL-1223 | ReO[V] | Ac-L-Nle-L-Arg-D-Phe-D-Nal 2-L-Cys-L-Trp-NH$_2$ | 10 | 64 | 79 |
| PL-1225 | ReO[V] | GBzA-Gly-D-Nal 2-L-Cys-L-Trp-NH$_2$ | 10 | 12 | 0 |
| PL-1226 | ReO[V] | AVA-Gly-D-Nal 2-L-Cys-L-Trp-NH$_2$ | 10 | 19 | 0 |
| PL-1227 | ReO[V] | 2-Abz-Gly-D-Nal 2-L-Cys-L-Trp-NH$_2$ | 10 | 5 | 0 |
| PL-1228 | ReO[V] | BAla-L-His-Gly-D-Nal 2-L-Cys-L-Trp-NH$_2$ | 10 | 11 | 64 |
| PL-1229 | ReO[V] | BAla-L-Nle-Gly-D-Nal 2-L-Cys-L-Trp-NH$_2$ | 10 | 32 | 21 |
| PL-1230 | ReO[V] | GAA-Gly-D-Nal 2-L-Cys-L-Trp-NH$_2$ | 10 | 32 | 20 |
| PL-1231 | ReO[V] | GVA(Cl)-Gly-D-Nal 2-L-Cys-L-Trp-NH$_2$ | 10 | 32 | 28 |
| PL-1232 | ReO[V] | Ac-L-Nle-L-Arg-L-Ala-D-Nal 2-L-Cys-L-Trp-NH$_2$ | 1 | 90 | 49 |
| PL-1233 | ReO[V] | BAla-L-Arg-D-Nal 2-L-Cys-L-Trp-NH$_2$ | 10 | 94 | 100 |
| PL-1234 | ReO[V] | BAla-D-Arg-D-Nal 2-L-Cys-L-Trp-NH$_2$ | 10 | 83 | 84 |
| PL-1235 | ReO[V] | Heptanoyl-L-Arg-D-Nal 2-L-Cys-L-Trp-NH$_2$ | 10 | 96 | 100 |
| PL-1236 | ReO[V] | Heptanoyl-D-Arg-D-Nal 2-L-Cys-L-Trp-NH$_2$ | 10 | 54 | 70 |
| PL-1237 | ReO[V] | BAla-Gly-D-Lys(Z)-L-Cys-L-Trp-NH$_2$ | 10 | 26 | 86 |
| PL-1238 | ReO[V] | BAla-Gly-D-Tyr(Bzl)-L-Cys-L-Trp-NH$_2$ | 10 | 40 | 40 |
| PL-1239 | ReO[V] | BAla-Gly-D-Phe(DiF 3,4)-L-Cys-L-Trp-NH$_2$ | 10 | 20 | 18 |
| PL-1240 | ReO[V] | BAla-Gly-D-Val-L-Cys-L-Trp-NH$_2$ | 10 | 13 | 0 |
| PL-1241 | ReO[V] | BAla-Gly-D-Nal 1-L-Cys-L-Trp-NH$_2$ | 10 | 34 | 23 |
| PL-1242 | ReO[V] | D-Nal 2-Gly-L-Arg-L-Cys-L-Trp-NH$_2$ | 10 | 61 | 80 |
| PL-1243 | ReO[V] | D-Nal 2-Gly-D-Arg-L-Cys-L-Trp-NH$_2$ | 10 | 62 | 88 |
| PL-1244 | ReO[V] | D-Phe-Gly-L-Arg-L-Cys-L-Trp-NH$_2$ | 10 | 46 | 69 |
| PL-1245 | ReO[V] | D-Phe-Gly-D-Arg-L-Cys-L-Trp-NH$_2$ | 10 | 50 | 74 |
| PL-1248 | ReO[V] | Ac-L-Nle-D-Arg-L-Ala-D-Nal 2-L-Cys-L-Trp-NH$_2$ | 10 | 69 | 63 |
| PL-1249 | ReO[V] | BAla-L-Nle-L-Ala-D-Nal 2-L-Cys-L-Trp-NH$_2$ | 10 | 64 | 40 |
| PL-1250 | ReO[V] | BAla-D-Nle-L-Ala-D-Nal 2-L-Cys-L-Trp-NH$_2$ | 1 | 79 | 10 |
| PL-1251 | ReO[V] | Ac-L-Nle-L-Arg-L-Phe-D-Nal 2-L-Cys-L-Trp-NH$_2$ | 1 | 82 | 77 |
| PL-1252 | ReO[V] | D-Lys(Z)-L-Ala-D-Nal 2-L-Cys-L-Trp-NH$_2$ | 10 | 44 | 34 |
| PL-1253 | ReO[V] | L-Ala-L-Ala-D-Nal 2-L-Cys-L-Trp-NH$_2$ | 10 | 54 | 27 |
| PL-1254 | ReO[V] | L-Ala-D-Nal 2-L-Cys-L-Trp-NH$_2$ | 10 | 40 | 43 |
| PL-1255 | ReO[V] | Bz-L-Arg-L-Ala-D-Nal 2-L-Cys-L-Trp-NH$_2$ | 1 | 85 | 14 |
| PL-1256 | ReO[V] | L-Arg-D-Nal 2-L-Cys-L-Trp-NH$_2$ | 10 | 60 | 57 |
| PL-1257 | ReO[V] | HOOC(CH$_2$)$_2$-CO-L-Arg-D-Nal 2-L-Cys-L-Trp-NH$_2$ | 10 | 51 | 43 |
| PL-1258 | ReO[V] | BAla-L-Nle-D-Nal 2-L-Cys-L-Trp-NH$_2$ | 10 | 66 | 57 |
| PL-1259 | ReO[V] | Ac-L-Nle-L-Ala-L-His-D-Phe-L-Arg-L-Cys-NH$_2$ | 1 | 31 | 82 |
| PL-1260 | ReO[V] | Ac-L-Nle-L-Arg-L-Ala-D-Nal 2-L-Cys-NH$_2$ | 1 | 74 | 49 |
| PL-1261 | ReO[V] | Heptanoyl-L-His-D-Phe-L-Arg-L-Cys-L-Trp-NH$_2$ | 1 | 30 | 101 |
| PL-1262 | ReO[V] | Heptanoyl-D-Phe-L-Arg-L-Cys-L-Trp-NH$_2$ | 1 | 20 | 44 |
| PL-1263 | ReO[V] | Ac-L-Arg(Tos)-D-Phe-L-Arg-L-Cys-L-Trp-NH$_2$ | 1 | 26 | 33 |
| PL-1264 | ReO[V] | Ac-L-Nle-L-Glu-L-His-D-Nal 2-L-Arg-L-Trp-L-Cys-NH$_2$ | 0.1 | 54 | 45 |

TABLE 1-continued

Melanocortin Receptor Screening Results: Receptor Binding Assay

| Compound ID | Metal ion/ Linear peptide | Sequence Structure | Conc. Cut off (μM) | % Inhibition MC4-R | MC1-R (B-16) |
|---|---|---|---|---|---|
| PL-1265 | ReO[V] | Ac-L-Glu-L-His-Gly-L-Arg-L-Trp-L-Cys-NH$_2$ (SEQ ID NO: 23) | 1 | 67 | 34 |
| PL-1266 | ReO[V] | Ac-L-Nle-L-Ala-D-Trp-D-Nal 2-L-Arg-L-Trp-L-Cys-NH$_2$ | 1 | 87 | 30 |
| PL-1267 | ReO[V] | Admentoyl-Gly-D-Nal 2-L-Arg-L-Trp-L-Cys-NH$_2$ | 1 | 55 | 36 |
| PL-1268 | ReO[V] | Bz-His-Gly-D-Nal 2-L-Arg-L-Trp-L-Cys-NH$_2$ | 1 | 97 | 57 |
| PL-1269 | ReO[V] | Bz-L-His-L-Cys-D-Nal 2-L-Arg-L-Trp-NH$_2$ | 1 | 99 | 25 |
| PL-1270 | Linear | Ac-L-Nle-L-Ala-L-His-D-Phe-L-Arg-L-Cys-L-Trp-NH$_2$ | 1 | 57 | 101 |
| PL-1271 | ReO[V] | Ac-D-Trp-D-Arg-L-Nal 2-L-Cys-D-His-L-Nal 2-NH$_2$ | 1 | 32 | 35 |
| PL-1272 | Linear | Heptanoyl-L-His-D-Phe-L-Arg-L-Cys-L-Trp-NH$_2$ | 1 | 36 | 100 |
| PL-1273 | ReO[V] | Ac-L-Nle-L-Arg-D-Ala-D-Nal 2-L-Cys-L-Trp-NH$_2$ | 10 | 53 | 78 |
| PL-1274 | ReO[V] | Ac-L-Nle-L-Arg-D-Phe-D-Nal 2-L-Cys-L-Trp-NH$_2$ | 10 | 45 | 75 |
| PL-1275 | ReO[V] | Des-aminoTyr-L-Lys-L-Ala-D-Nal 2-L-Cys-L-Trp-NH$_2$ | 1 | 17 | −4 |
| PL-1276 | ReO[V] | Heptanoyl-L-Lys-L-Ala-D-Nal 2-L-Cys-L-Trp-NH$_2$ | 1 | 64 | 4 |
| PL-1277 | ReO[V] | 3-Pyridine propionyl-L-Lys-L-Ala-D-Nal 2-L-Cys-L-Trp-NH$_2$ | 1 | 38 | −17 |
| PL-1278 | ReO[V] | EtOOC-(CH$_2$)$_4$-CO-L-Lys-L-Ala-D-Nal 2-L-Cys-L-Trp-NH$_2$ | 1 | 32 | −13 |
| PL-1279 | ReO[V] | (s)-2-OH-isocaproyl--L-Lys-L-Phe-D-Nal 2-L-Cys-L-Trp-NH$_2$ | 1 | 55 | −10 |
| PL-1280 | ReO[V] | 4-MePhenoxyacetyl--L-Lys-L-Ala-D-Nal 2-L-Cys-L-Trp-NH$_2$ | 1 | 49 | −11 |
| PL-1281 | ReO[V] | Heptanoyl-L-Lys-L-Ala-D-Phe-L-Cys-L-Trp-NH$_2$ | 1 | 29 | 60 |
| PL-1282 | ReO[V] | Heptanoyl-L-Lys-L-Ala-D-Phe-D-Cys-L-Trp-NH$_2$ | 1 | 14 | −30 |
| PL-1283 | ReO[V] | Des-aminoPhe-L-Lys-L-Ala-D-Nal 2-L-Cys-L-Trp-NH$_2$ | 1 | 45 | −20 |
| PL-1284 | ReO[V] | BAla-L-Lys(Ac)-L-Ala-D-Nal 2-L-Cys-L-Trp-NH$_2$ | 1 | 27 | −26 |
| PL-1285 | ReO[V] | Ac-L-Nle-L-Ala-D-Trp-D-Phe-L-Arg-L-Trp-L-Cys-NH$_2$ | 1 | 32 | 54 |
| PL-1286 | ReO[V] | Ac-L-Nle-L-Ala-D-Nal 2-D-Phe-L-Arg-L-Trp-L-Cys-NH$_2$ | 1 | 34 | 7 |
| PL-1287 | ReO[V] | Ac-L-Nle-L-Ala-D-His-D-Phe-L-Arg-L-Trp-L-Cys-NH$_2$ | 1 | 40 | 62 |
| PL-1288 | ReO[V] | EtOOC-(CH$_2$)$_4$-CO-D-Phe-L-Arg-L-Cys-L-Trp-NH$_2$ | 1 | 16 | −3 |
| PL-1289 | ReO[V] | 4-n-Heptanoyl-D-Phe-L-Arg-L-Cys-L-Trp-NH$_2$ | 1 | 31 | −7 |
| PL-1290 | ReO[V] | Des-aminoTyr-D-Phe-L-Arg-L-Cys-L-Trp-NH$_2$ | 1 | 24 | −22 |
| PL-1291 | ReO[V] | Me2-CH—CH(L-OH)-CO-D-Phe-L-Arg-L-Cys-L-Trp-NH$_2$ | 1 | 29 | 1 |
| PL-1292 | ReO[V] | Ac-D-Ala-L-HisL-Cys-D-Nal 2-L-Arg-Tryptamide | 1 | 87 | 25 |
| PL-1293 | ReO[V] | Ac-D-Ala-L-HisL-Cys-D-Nal 2-L-Arg-Tryptamide | 1 | 96 | 21 |
| PL-1294 | ReO[V] | Bz-L-His-L-Cys-D-Phe-L-Arg-L-Trp-NH$_2$ | 1 | 65 | 62 |
| PL-1295 | ReO[V] | Bz-L-Ala-L-Cys-D-Phe-L-Arg-L-Trp-NH$_2$ | 1 | 72 | 62 |
| PL-1296 | ReO[V] | Bz-L-Nal 2-L-Cys-D-Phe-L-Arg-L-Trp-NH$_2$ | 1 | 51 | 51 |
| PL-1297 | ReO[V] | Des-aminoPhe-L-Cys-D-Nal 2-L-Arg-L-Trp-NH$_2$ | 1 | 91 | 31 |
| PL-1298 | ReO[V] | Heptanoyl-L-Cys-D-Nal 2-L-Arg-L-Trp-NH$_2$ | 1 | 95 | 43 |
| PL-1299 | ReO[V] | Heptanoyl-BAla-L-Arg-L-Cys-L-Trp-NH$_2$ (SEQ ID NO: 24) | 1 | 19 | 1 |
| PL-1300 | ReO[V] | Heptanoyl-L-Ala-L-Arg-L-Cys-L-Trp-NH$_2$ (SEQ ID NO: 25) | 1 | 22 | 62 |
| PL-1301 | ReO[V] | L-Lys(Z)-L-Ala-D-Nal 2-L-Cys-L-Trp-NH$_2$ | 1 | 72 | 49 |
| PL-1302 | ReO[V] | Heptanoyl-L-His-D-Phe-L-Arg-D-Cys-L-Trp-NH$_2$ | 1 | 24 | 77 |
| PL-1303 | ReO[V] | Heptanoyl-L-His-D-Nal 2-L-Arg-D-CysL-Trp-NH$_2$ | 1 | 60 | 39 |
| PL-1304 | ReO[V] | D-Lys(Z)-L-Ala-D-Nal 2-L-Cys-L-Trp-NH$_2$ | 1 | 42 | −10 |
| PL-1305 | ReO[V] | Ac-L-Nle-L-Arg-L-Ala-D-Nal 2-L-Cys-L-Trp-NH$_2$ | 1 | 91 | 14 |
| PL-1306 | ReO[V] | Ac-L-Nle-L-Arg-L-Ala-D-Phe-L-Cys-L-Trp-NH$_2$ | 1 | 36 | 56 |
| PL-1309 | ReO[V] | Heptanoyl-L-Cys-L-Arg-L-Cys-L-Trp-NH$_2$ (SEQ ID NO: 26) | 1 | 10 | 9 |
| PL-1310 | ReO[V] | Des-aminoTyr-L-Lys-L-Ala-D-Nal 2-L-Cys-L-Trp-NH$_2$ | 10 | 78 | 100 |
| PL-1311 | ReO[V] | Heptanoyl-L-Lys-L-Ala-D-Nal 2-L-Cys-L-Trp-NH$_2$ | 10 | 61 | 40 |
| PL-1312 | ReO[V] | 3-Pyridine propionyl-L-Lys-L-Ala-D-Nal 2-L-Cys-L-Trp-NH$_2$ | 10 | 71 | 43 |
| PL-1313 | ReO[V] | Heptanoyl-L-Ala-L-Trp-D-Arg-L-Cys-L-Phe-NH$_2$ | 1 | 6 | 16 |
| PL-1314 | ReO[V] | C$_{11}$H$_{23}$-CO-L-Trp-D-Arg-L-Cys-L-Phe-NH$_2$ | 10 | 85 | 53 |
| PL-1315 | ReO[V] | Ac-L-Arg-L-Trp-L-Nle-L-Cys-L-Phe-NH$_2$ (SEQ ID NO: 27) | 10 | 70 | 69 |
| PL-1316 | ReO[V] | Ac-L-Arg-D-Trp-L-Nle-L-Cys-L-Phe-NH$_2$ | 10 | 82 | 91 |
| PL-1317 | ReO[V] | Ac-L-Trp-L-Nle-D-Phe-L-Cys-L-Arg-NH$_2$ | 10 | 79 | 92 |
| PL-1318 | ReO[V] | C$_6$H$_5$-(CH$_2$)$_2$-CO-L-Nle-D-Trp-L-Cys-L-Arg-NH$_2$ | 10 | 82 | 82 |
| PL-1319 | ReO[V] | Ac-L-Trp-D-Arg-L-Phe-L-Cys-L-Nle-NH$_2$ | 10 | 61 | 89 |
| PL-1320 | ReO[V] | C$_6$H$_5$-(CH$_2$)$_2$-CO-L-Arg-L-Trp-L-Cys-L-Nle-NH$_2$ (SEQ ID NO: 28) | 10 | 94 | 96 |
| PL-1321 | ReO[V] | Bz-L-Arg-L-Ala-D-Phe-L-Cys-L-Phe-NH$_2$ | 10 | 79 | 93 |
| PL-1322 | ReO[V] | Bz-L-Arg-L-Ala-D-Trp-L-Cys-L-Phe-NH$_2$ | 10 | 66 | 81 |
| PL-1323 | ReO[V] | Bz-L-Arg-L-Ala-D-Phe-L-Cys-L-Nle-NH$_2$ | 10 | 77 | 99 |
| PL-1324 | ReO[V] | Des-aminoPhe-L-Lys-L-Arg-D-Phe-L-Cys-L-Nle-NH$_2$ | 10 | 75 | 93 |
| PL-1325 | ReO[V] | Des-aminoPhe-L-Cys-D-Phe-L-Arg-L-Phe-NH$_2$ | 10 | 78 | 94 |
| PL-1326 | ReO[V] | Heptanoyl-D-Phe-L-Arg-D-Trp-L-Cys-NH$_2$ | 10 | 62 | 68 |
| PL-1327 | ReO[V] | Heptanoyl-L-Phe-L-Arg-D-Trp-L-Cys-NH$_2$ | 10 | 87 | 93 |
| PL-1328 | ReO[V] | Ac-D-Nal 2-L-Ala-L-Arg-L-Cys-L-Trp-NH$_2$ | 10 | 78 | 83 |
| PL-1329 | ReO[V] | Ac-L-Nle-L-Ala-D-Trp-D-Nal 2-L-Arg-D-Trp-L-Cys-NH$_2$ | 1 | 88 | 30 |
| PL-1330 | ReO[V] | Ac-L-Nle-L-Arg-L-Ala-D-Nal 2-L-Cys-D-Trp-NH$_2$ | 1 | 94 | 53 |
| PL-1331 | ReO[V] | Des-aminoPhe-L-Cys-D-Phe-L-Arg-L-Nle-NH$_2$ | 10 | 74 | 82 |
| PL-1332 | ReO[V] | Des-aminoPhe-L-Cys-D-Nal 2-L-Arg-Gly-L-Phe-NH$_2$ | 10 | 98 | 80 |
| PL-1333 | ReO[V] | Des-aminoPhe-L-Cys-D-Nal 2-L-Arg-Gly-L-Trp-NH$_2$ | 10 | 95 | 77 |
| PL-1334 | ReO[V] | C$_6$H$_5$-(CH$_2$)$_2$-CO-L-Nle-L-Trp-L-Cys-L-Arg-NH$_2$ (SEQ ID NO: 29) | 1 | 12 | 26 |
| PL-1335 | ReO[V] | Heptanoyl-L-HPhe-D-Nal 2-L-Arg-L-Trp-L-Cys-NH$_2$ | 1 | 98 | 36 |
| PL-1340 | ReO[V] | D-(N-Bzl)Nal 2-L-Arg-L-Trp-L-Cys-NH$_2$ | 1 | 99 | 34 |
| PL-1341 | ReO[V] | D-(N-PhEt)Nal 2-L-Arg-L-Trp-L-Cys-NH$_2$ | 1 | 100 | 46 |
| PL-1342 | ReO[V] | Ac-L-Nle-L-Arg-D-His-D-Phe-L-Cys-L-Trp-NH$_2$ | 1 | 37 | 89 |

TABLE 1-continued

Melanocortin Receptor Screening Results: Receptor Binding Assay

| Compound ID | Metal ion/ Linear peptide | Sequence Structure | Conc. Cut off (µM) | % Inhibition MC4-R | MC1-R (B-16) |
|---|---|---|---|---|---|
| PL-1343 | ReO[V] | Ac-L-Nle-L-Arg-L-His-D-Phe-L-Cys-L-Trp-NH₂ | 10 | 50 | 86 |
| PL-1344 | ReO[V] | Heptanoyl-L-Arg-L-Phe-L-His-L-Cys-L-Trp-NH₂ (SEQ ID NO: 30) | 10 | 81 | 89 |
| PL-1345 | ReO[V] | Heptanoyl-L-Arg-L-Phe-D-His-L-Cys-L-Trp-NH₂ | 10 | 80 | 95 |
| PL-1345 | ReO[V] | Heptanoyl-L-Arg-L-Phe-D-His-L-Cys-L-Trp-NH₂ | 1 | 52 | 38 |
| PL-1346 | ReO[V] | Ph(CH₂)₂-CO-L-His-L-Arg-L-Cys-L-Trp-NH₂ (SEQ ID NO: 31) | 10 | 77 | 86 |
| PL-1347 | ReO[V] | Ph(CH₂)₂-CO-D-His-L-Arg-L-Cys-L-Trp-NH₂ | 10 | 70 | 64 |
| PL-1348 | ReO[V] | Ac-L-Arg-L-His-L-Phe-L-Cys-L-Trp-NH₂ (SEQ ID NO: 32) | 10 | 51 | 57 |
| PL-1349 | ReO[V] | Ac-L-Arg-D-His-L-Phe-L-Cys-L-Trp-NH₂ | 10 | 46 | 60 |
| PL-1350 | ReO[V] | Ac-L-Arg-D-His-D-Phe-L-Cys-L-Trp-NH₂ | 10 | 42 | 70 |
| PL-1351 | ReO[V] | Ac-L-Arg-L-His-D-Phe-L-Cys-L-Trp-NH₂ | 1 | 6 | 68 |
| PL-1358 | ReO[V] | Ac-L-Nle-L-Arg-L-Trp-D-Phe-L-Cys-L-His-NH₂ | 10 | 66 | 98 |
| PL-1359 | ReO[V] | Ac-L-Nle-L-Arg-D-Trp-D-Phe-L-Cys-L-His-NH₂ | 10 | 62 | 90 |
| PL-1360 | ReO[V] | Ac-L-Arg-L-Trp-L-Phe-L-Cys-L-His-NH₂ (SEQ ID NO: 33) | 10 | 62 | 57 |
| PL-1362 | ReO[V] | Ac-L-Arg-L-Trp-D-Phe-L-Cys-L-His-NH₂ | 10 | 59 | 74 |
| PL-1363 | ReO[V] | Ac-L-Arg-D-Trp-D-Phe-L-Cys-L-His-NH₂ | 10 | 74 | 92 |
| PL-1364 | ReO[V] | Ac-L-Trp-L-Phe-L-His-L-Cys-L-Arg-NH₂ (SEQ ID NO: 34) | 10 | 72 | 74 |
| PL-1365 | ReO[V] | Ac-L-Trp-L-Phe-D-His-L-Cys-L-Arg-NH₂ | 10 | 64 | 71 |
| PL-1366 | ReO[V] | Ac-L-His-L-Phe-L-Trp-L-Cys-L-Arg-NH₂ (SEQ ID NO: 35) | 10 | 64 | 78 |
| PL-1367 | ReO[V] | Ac-L-His-L-Phe-D-Trp-L-Cys-L-Arg-NH₂ | 10 | 73 | 95 |
| PL-1370 | ReO[V] | Ac-L-Nle-L-Arg-L-Ala-D-Phe(CF₃)-L-Cys-L-Trp-NH₂ | 1 | 87 | 51 |
| PL-1371 | ReO[V] | Ac-L-Nle-L-Arg-L-Ala-D-Phe(3,4 di-OMe)-L-Cys-L-Trp-NH₂ | 1 | 44 | 35 |
| PL-1372 | ReO[V] | Ac-L-Nle-L-Arg-L-Ala-D-Phe(4-Me)-L-Cys-L-Trp-NH₂ | 1 | 87 | 82 |
| PL-1373 | ReO[V] | Ac-L-Nle-L-Arg-L-Ala-D-Phe(3,4 diCl)-L-Cys-L-Trp-NH₂ | 1 | 92 | 54 |
| PL-1374 | ReO[V] | Ac-L-Nle-L-Arg-L-Ala-D-Phe(4-Cl)-L-Cys-L-Trp-NH₂ | 1 | 89 | 83 |
| PL-1375 | ReO[V] | Ac-L-Nle-L-Arg-L-Ala-D-Phe(3,4 diF)-L-Cys-L-Trp-NH₂ | 1 | 54 | 78 |
| PL-1376 | ReO[V] | Ac-L-Nle-L-Arg-L-Ala-D-Val-L-Cys-L-Trp-NH₂ | 1 | 31 | 33 |
| PL-1385 | ReO[V] | Ac-L-Nle-L-Arg-L-Ala-D-Leu-L-Cys-L-Trp-NH₂ | 1 | 45 | 34 |
| PL-1386 | ReO[V] | HOOC-(CH₂)₅-CO-L-His-D-Phe-L-Arg-L-Cys-L-Trp-NH₂ | 0.1 | 1 | 71 |
| PL-1387 | Linear | HOOC-(CH₂)₅-CO-L-His-D-Phe-L-Arg-L-Cys-L-Trp-NH₂ | 0.1 | 1 | 76 |
| PL-1388 | ReO[V] | NH₂-(CH₂)₅-CO-L-His-D-Phe-L-Arg-L-Cys-L-Trp-NH₂ | 0.1 | −10 | 80 |
| PL-1389 | Linear | NH₂-(CH₂)₅-CO-L-His-D-Phe-L-Arg-L-Cys-L-Trp-NH₂ | 0.1 | 7 | 87 |
| PL-1390 | ReO[V] | L-Lys(Z)-D-His-D-Nal 2-L-Cys-L-Trp-NH₂ | 10 | 63 | 88 |
| PL-1391 | ReO[V] | Ac-L-Nle-L-Arg-D-His-D-Nal 2-L-Cys-L-Trp-NH₂ | 10 | 72 | 103 |
| PL-1391 | ReO[V] | Ac-L-Nle-L-Arg-D-His-D-Nal 2-L-Cys-L-Trp-NH₂ | 1 | 25 | 58 |
| PL-1392 | ReO[V] | B Ala-D-Nle-D-His-D-Nal 2-L-Cys-L-Trp-NH₂ | 10 | 80 | 84 |
| PL-1393 | ReO[V] | Bz-L-Arg-D-His-D-Nal 2-L-Cys-L-Trp-NH₂ | 10 | 65 | 86 |
| PL-1394 | ReO[V] | Ac-L-His-L-Arg-L-Trp-L-Cys-L-Phe-NH₂ (SEQ ID NO: 36) | 10 | 59 | 84 |
| PL-1394 | ReO[V] | Ac-L-His-L-Arg-L-Trp-L-Cys-L-Phe-NH₂ (SEQ ID NO: 36) | 1 | 0 | 27 |
| PL-1395 | ReO[V] | Ac-L-His-D-Arg-L-Trp-L-Cys-L-Phe-NH₂ | 1 | 5 | 10 |
| PL-1395 | ReO[V] | Ac-L-His-D-Arg-L-Trp-L-Cys-L-Phe-NH₂ | 10 | 78 | 74 |
| PL-1396 | ReO[V] | Ac-L-Nle-L-Ala-L-His-D-Nal 2-L-Arg-L-Cys-L-Trp-NH₂ | 1 | 70 | 96 |
| PL-1405 | ReO[V] | Heptanoyl-L-Phe-L-His-L-Cys-L-Trp-NH₂ (SEQ ID NO: 37) | 1 | 27 | 20 |
| PL-1406 | ReO[V] | Heptanoyl-L-Arg-L-Phe-L-His-L-Cys-L-Trp-NH₂ (SEQ ID NO: 30) | 1 | 42 | 32 |
| PL-1412 | ReO[V] | L-Phe-L-His-L-Cys-L-Trp-NH₂ (SEQ ID NO: 38) | 1 | 54 | 43 |
| PL-1413 | ReO[V] | Heptanoyl-D-Nal 2-L-Arg-L-Trp-L-Cys-NH₂ | 1 | 86 | 51 |
| PL-1414 | ReO[V] | Heptanoyl-Psi D-Nal 2-L-Arg-L-Trp-L-Cys-NH₂ | 1 | 53 | 26 |
| PL-1415 | ReO[V] | Heptanoyl-D-Nal 2-L-Psi-L-Arg-L-Trp-L-Cys-NH₂ | 1 | 0 | 25 |
| PL-1416 | ReO[V] | Ac-L-Nle-L-Ala-L-His-L-Phe-L-Arg-L-Cys-L-Trp-NH₂ (SEQ ID NO: 39) | 1 | 35 | 85 |
| PL-1417 | ReO[V] | Ac-L-Nle-L-Ala-L-His-L-Phe-D-Arg-L-Cys-L-Trp-NH₂ | 1 | 11 | 20 |
| PL-1418 | ReO[V] | Ac-L-Nle-L-Ala-L-His-D-Phe-D-Arg-L-Cys-L-Trp-NH₂ | 1 | 24 | 80 |
| PL-1419 | ReO[V] | Ac-L-Nle-L-Ala-L-His-D-Nal 2-L-Arg-L-Cys-L-Trp-NH₂ | 1 | 51 | 70 |
| PL-1420 | ReO[V] | Ac-L-Nle-L-Ala-L-His-L-Nal 2-D-Arg-L-Cys-L-Trp-NH₂ | 1 | 52 | 43 |
| PL-1421 | ReO[V] | Ac-L-Nle-L-Ala-L-His-D-Nal 2-D-Arg-L-Cys-L-Trp-NH₂ | 1 | 59 | 81 |
| PL-1422 | ReO[V] | Ac-L-Nle-L-Arg-L-Ala-D-Phe(4-Cl)-L-Cys-L-His-NH₂ | 1 | 63 | 69 |
| PL-1423 | ReO[V] | Ac-L-Nle-L-Arg-L-Ala-D-Phe(4-Cl)-L-Cys-L-Phe(4-NO₂)-NH₂ | 1 | 71 | 78 |
| PL-1424 | ReO[V] | Ac-L-Nle-L-Arg-L-Ala-D-Phe(4-Cl)-L-Cys-L-Phe-NH₂ | 1 | 66 | 85 |
| PL-1425 | ReO[V] | Ac-L-Nle-L-Arg-L-Ala-D-Phe(4-Cl)-L-Cys-L-Glu-NH₂ | 1 | 6 | 39 |
| PL-1426 | ReO[V] | Ac-L-Nle-L-Arg-L-Ala-D-Phe(4-Cl)-L-Cys-L-Gln-NH₂ | 1 | 16 | 71 |
| PL-1427 | ReO[V] | Ac-L-Nle-L-Arg-L-Ala-D-Phe(4-Cl)-L-Cys-L-Trp-NH₂ | 1 | 82 | 90 |
| PL-1428 | ReO[V] | Ac-L-Nle-L-Arg-L-Ala-D-His-L-Cys-L-Trp-NH₂ | 1 | 45 | 56 |
| PL-1429 | ReO[V] | Ac-L-Nle-L-Arg-L-Ala-D-Phe(4-Me)-L-Cys-L-Trp-NH₂ | 1 | 84 | 80 |
| PL-1430 | ReO[V] | Ac-L-Nle-L-Arg-L-Ala-D-HomoPhe-L-Cys-L-Trp-NH₂ | 1 | 40 | 26 |
| PL-1431 | ReO[V] | Ac-L-Nle-L-Arg-L-Ala-D-Phg-L-Cys-L-Trp-NH₂ | 1 | 41 | 20 |
| PL-1432 | ReO[V] | Ac-L-Nle-L-Arg-L-Ala-D-Trp-L-Cys-L-Trp-NH₂ | 1 | 47 | 38 |
| PL-1433 | ReO[V] | Ac-L-Nle-L-Arg-L-Ala-D-Cha-L-Cys-L-Trp-NH₂ | 1 | 38 | 14 |
| PL-1434 | ReO[V] | Ac-L-Nle-L-Arg-L-Ala-D-Chg-L-Cys-L-Trp-NH₂ | 1 | 53 | 33 |
| PL-1435 | ReO[V] | Ac-L-Nle-L-Arg-L-His-L-Ala-L-Cys-L-Phe(4-Cl)-NH₂ | 1 | 59 | 44 |
| PL-1436 | ReO[V] | Ac-L-Nle-L-His-L-Arg-L-Ala-D-Phe(4-Cl)-L-Cys-L-Trp-NH₂ | 1 | 58 | 51 |
| PL-1438 | ReO[V] | Ac-L-Nle-L-Arg-L-His-D-Phe(4-Cl)-L-Cys-L-Trp-NH₂ | 1 | 91 | 89 |
| PL-1439 | ReO[V] | Ac-L-Nle-L-Arg-D-His-D-Phe(4-Cl)-L-Cys-L-Trp-NH₂ | 1 | 43 | 92 |
| PL-1440 | ReO[V] | Ac-L-Nle-L-Arg-L-Lys-D-Phe(4-Cl)-L-Cys-L-Trp-NH₂ | 1 | 94 | 79 |
| PL-1441 | ReO[V] | Ac-L-Nle-L-Arg-D-Lys-D-Phe(4-Cl)-L-Cys-L-Trp-NH₂ | 1 | 51 | 71 |

TABLE 1-continued

Melanocortin Receptor Screening Results: Receptor Binding Assay

| Compound ID | Metal ion/ Linear peptide | Sequence Structure | Conc. Cut off (µM) | % Inhibition MC4-R | MC1-R (B-16) |
|---|---|---|---|---|---|
| PL-1442 | ReO[V] | Ac-L-Nle-L-Arg-L-Ala-D-Phe(4-F)-L-Cys-L-Trp-NH$_2$ | 1 | 85 | 93 |
| PL-1443 | ReO[V] | Ac-L-Nle-L-Arg-L-Ala-D-Phe(4-I)-L-Cys-L-Trp-NH$_2$ | 1 | 99 | 72 |
| PL-1444 | ReO[V] | Ac-L-Nle-L-Arg-L-Ala-D-Tyr-L-Cys-L-Trp-NH$_2$ | 1 | 52 | 68 |
| PL-1445 | ReO[V] | Ac-L-Nle-L-Arg-L-Ala-D-Phe(4-NO$_2$)-L-Cys-L-Trp-NH$_2$ | 1 | 83 | 63 |
| PL-1446 | ReO[V] | L-Ala-D-Nal 2-L-Cys-L-Trp-NH$_2$ | 1 | 50 | 14 |
| PL-1447 | ReO[V] | Heptanoyl-L-Ala-D-Nal 2-L-Cys-L-Trp-NH$_2$ | 1 | 44 | 12 |
| PL-1448 | ReO[V] | L-Arg-D-Nal 2-L-Cys-L-Trp-NH$_2$ | 1 | 62 | 26 |
| PL-1449 | ReO[V] | Heptanoyl-L-Arg-D-Nal 2-L-Cys-L-Trp-NH$_2$ | 1 | 80 | 45 |
| PL-1450 | ReO[V] | Ac-L-Nle-L-Ala-L-His-L-Phe-L-Arg-L-Cys-L-Trp-NH$_2$ (SEQ ID NO: 40) | 1 | 66 | 73 |
| PL-1451 | ReO[V] | Ac-L-Nle-L-Arg-L-Ala-D-Phe(4-Br)-L-Cys-L-Trp-NH$_2$ | 1 | 92 | 77 |
| PL-1452 | ReO[V] | Ac-L-Nle-L-Arg-L-Ala-D-Phe(4-Br)-L-Cys-L-Trp-NH$_2$ | 1 | 97 | 86 |
| PL-1457 | ReO[V] | Ac-L-Ala-L-His-L-Cys-D-Bip-L-Arg-L-Trp-NH$_2$ | 1 | 79 | 26 |
| PL-1458 | ReO[V] | Ac-L-Ala-L-His-L-Cys-D-Phe-L-Arg-L-Trp-NH$_2$ | 1 | 61 | 48 |
| PL-1459 | ReO[V] | Ac-L-Ala-L-His-L-Cys-D-Asp(3-Cl-anilino)-L-Arg-L-Trp-NH$_2$ | 1 | 31 | 68 |
| PL-1460 | ReO[V] | Ac-L-Ala-L-His-L-Cys-D-Asp(3,6-diCl-anilino)-L-Arg-L-Trp-NH$_2$ | 1 | 40 | 47 |
| PL-1461 | ReO[V] | Ac-L-Ala-L-His-L-Cys-D-Asp(anilino)-L-Arg-L-Trp-NH$_2$ | 1 | 60 | 43 |
| PL-1462 | ReO[V] | Heptanoyl-L-His-D-Phe-L-Arg-L-Cys-L-Nal 2-NH$_2$ | 1 | 39 | 99 |
| PL-1463 | ReO[V] | Heptanoyl-L-His-D-Phe-L-Arg-D-Cys-L-Nal 2-NH$_2$ | 1 | 57 | 93 |
| PL-1464 | ReO[V] | Heptanoyl-L-His-D-Phe-L-Arg-L-Cys-D-Nal 2-NH$_2$ | 1 | 80 | 94 |
| PL-1465 | ReO[V] | Heptanoyl-L-His-D-Phe-L-Phe-L-Arg-D-Cys-D-Nal 2-NH$_2$ | 1 | 48 | 84 |
| PL-1466 | ReO[V] | Heptanoyl-L-His-D-Phe-D-Arg-L-Cys-L-Trp-NH$_2$ | 1 | 37 | 67 |
| PL-1467 | ReO[V] | Heptanoyl-L-His-D-Phe-D-Arg-D-Cys-L-Trp-NH$_2$ | 1 | 47 | 69 |
| PL-1478 | ReO[V] | Ac-L-Arg-L-Phe-L-Phe-L-Cys-L-Ser-NH$_2$ (SEQ ID NO: 41) | 1 | 21 | 28 |
| PL-1480 | ReO[V] | Ac-L-Arg-D-Phe-L-Phe-L-Cys-L-Ser-NH$_2$ | 1 | 9 | 21 |
| PL-1481 | ReO[V] | Ac-L-Arg-D-Phg-L-Phe-L-Cys-L-Ser-NH$_2$ | 1 | 15 | 19 |
| PL-1483 | ReO[V] | Ac-L-Arg-L-Phe-L-Nal 2-L-Cys-L-Ser-NH$_2$ | 1 | 31 | 56 |
| PL-1484 | ReO[V] | Ac-L-Arg-D-Phe-L-Nal 2-L-Cys-L-Ser-NH$_2$ | 1 | 37 | 72 |
| PL-1485 | ReO[V] | Ac-L-Arg-D-Phg-L-Nal 2-L-Cys-L-Ser-NH$_2$ | 1 | 41 | 60 |
| PL-1486 | ReO[V] | Ac-D-Ala-L-His-L-Cys-D-Nal 2-L-Arg-L-Trp-NH$_2$ | 1 | 90 | 26 |
| PL-1488 | Linear | Ac-D-Ala-L-His-L-Cys-D-Nal 2-L-Arg-L-Trp-NH$_2$ | 1 | 85 | 35 |
| PL-1489 | ReO[V] | Heptanoyl-L-Ser(Bzl)-D-Nal 2-L-Arg-L-Trp-L-Cys-NH$_2$ | 1 | 99 | 30 |
| PL-1490 | Linear | Heptanoyl-L-Ser(Bzl)-D-Nal 2-L-Arg-L-Trp-L-Cys-NH$_2$ | 1 | 86 | 48 |
| PL-1491 | ReO[V] | Heptanoyl-L-Ser(Bzl)-D-Nal 2-L-Arg-L-Phe-L-Cys-NH$_2$ | 1 | 76 | 66 |
| PL-1492 | ReO[V] | Heptanoyl-L-Ser(Bzl)-D-Nal 2-L-Arg-D-Phe-L-Cys-NH$_2$ | 1 | 90 | 63 |
| PL-1493 | ReO[V] | Heptanoyl-L-Ser(Bzl)-D-Nal 2-L-Arg-D-Trp-L-Cys-NH$_2$ | 1 | 102 | 26 |
| PL-1494 | ReO[V] | Ac-L-Lys-L-Cys-D-Phe-L-Trp-L-Nle-NH$_2$ | 1 | 30 | 27 |
| PL-1496 | ReO[V] | Ac-L-Asp-L-Lys-L-Pro-L-Pro-L-Arg-L-Ala-D-Nal 2-L-Cys-L-Trp-NH$_2$ | 1 | 59 | 43 |
| PL-1497 | ReO[V] | L-Asp-L-Lys-L-Pro-L-Pro-L-Arg-L-Ala-D-Nal 2-L-Cys-L-Trp-NH$_2$ | 1 | 71 | 47 |
| PL-1498 | ReO[V] | Ac-L-Nle-L-Arg-L-Ala-D-Nal 2-L-Cys-L-Trp-Ahx-L-Lys-L-Asp-NH$_2$ | 1 | 86 | 59 |
| PL-1499 | ReO[V] | Heptanoyl-L-Lys-D-Phe-L-Trp-L-Cys-NH$_2$ | 1 | 20 | 23 |
| PL-1500 | ReO[V] | Heptanoyl-D-Phe-L-Trp-L-Cys-L-Lys-NH$_2$ | 1 | 33 | 25 |
| PL-1501 | ReO[V] | Heptanoyl-L-His-D-Trp-L-Cys-L-Trp-NH$_2$ | 1 | 44 | 78 |
| PL-1502 | ReO[V] | Heptanoyl-L-His-D-Trp-Gly-L-Cys-L-Lys-NH$_2$ | 1 | 41 | 29 |
| PL-1503 | ReO[V] | Heptanoyl-L-Phe-D-Phe-L-Arg-L-Cys-L-Trp-NH$_2$ | 1 | 41 | 52 |
| PL-1504 | ReO[V] | Ac-L-Arg-L-Phe-L-Nal 2-L-Asn-L-Cys-L-Phe-NH$_2$ (SEQ ID NO: 42) | 1 | 21 | 36 |
| PL-1505 | ReO[V] | Ac-L-Arg-L-Phe-L-Nal 2-L-Asn-L-Cys-L-Phe-NH$_2$ (SEQ ID NO: 42) | 1 | 29 | 45 |
| PL-1506 | ReO[V] | Ac-L-Arg-D-Phe-L-Nal 2-L-Asn-L-Cys-L-Phe-NH$_2$ | 1 | 22 | 30 |
| PL-1507 | ReO[V] | Ac-L-Arg-L-Phe-L-Phe-L-Asn-L-Cys-L-Phe-NH$_2$ (SEQ ID NO: 43) | 1 | 22 | 20 |
| PL-1508 | ReO[V] | Ac-L-Arg-D-Phe-L-Phe-L-Asn-L-Cys-L-Phe-NH$_2$ | 1 | 31 | 20 |
| PL-1509 | ReO[V] | Ac-L-Arg-L-Phe-L-Phe-L-Cys-L-Phe-L-Asn-L-Ala-L-Phe-NH$_2$ (SEQ ID NO: 44) | 1 | 30 | 19 |
| PL-1510 | ReO[V] | Ac-L-Arg-L-Phe-L-Phe-L-Cys-L-Asn-L-Ala-L-Phe-NH$_2$ (SEQ ID NO: 45) | 1 | 31 | 21 |
| PL-1511 | ReO[V] | Ac-L-Arg-L-Phe-L-Phe-L-Asn-L-Cys-L-Ala-L-Phe-NH$_2$ (SEQ ID NO: 46) | 1 | 26 | 21 |
| PL-1512 | ReO[V] | Ac-L-Arg-L-Phe-L-Phe-L-Asn-L-Ala-L-Cys-L-Phe-NH$_2$ (SEQ ID NO: 47) | 1 | 24 | 20 |
| PL-1513 | ReO[V] | Ac-L-Arg-L-Phe-L-Phe-L-Asn-L-Phe-L-Cys-NH$_2$ (SEQ ID NO: 48) | 1 | 18 | 23 |
| PL-1514 | ReO[V] | Ac-L-Arg-L-Phe-L-Phe-L-Asn-L-Phe-L-Cys-NH$_2$ (SEQ ID NO: 48) | 1 | 30 | 28 |
| PL-1515 | ReO[V] | Heptanoyl-L-His-D-Phe-L-Lys-L-Cys-L-Glu | 1 | 34 | 21 |
| PL-1518 | ReO[V] | Heptanoyl-L-Cys-D-Phe-L-Trp-L-Lys-NH$_2$ | 1 | 25 | 8 |
| PL-1519 | ReO[V] | Ac-L-Nle-L-Arg-L-Ala-D-Nal 2-L-Cys-L-Trp-L-Pro-L-Pro-L-Lys-L-Asp-NH$_2$ | 1 | 60 | 22 |
| PL-1522 | ReO[V] | Ac-L-Nle-L-Arg-L-Ala-L-His-D-Phe(4-Br)-L-Cys-L-Trp-NH$_2$ | 1 | 91 | 87 |
| PL-1523 | ReO[V] | Ac-L-Nle-L-Arg-L-Ala-L-His-D-Phe(4-Br)-L-Cys-L-Trp-NH$_2$ | 1 | 59 | 69 |
| PL-1524 | ReO[V] | Ac-L-Nle-L-Arg-L-His-L-Ala-D-Phe(4-Br)-L-Cys-L-Trp-NH$_2$ | 1 | 44 | 36 |
| PL-1525 | ReO[V] | Ac-L-Nle-L-Arg-L-Phe(4-Br)-L-Ala-L-His-L-Cys-L-Trp-NH$_2$ | 1 | 41 | 57 |
| PL-1526 | ReO[V] | Ac-L-Nle-L-Arg-L-Trp-L-Ala-D-Phe(4-Br)-L-Cys-L-His-NH$_2$ | 1 | 34 | 63 |
| PL-1581 | ReO[V] | Ac-L-Nle-L-Ala-L-His-D-Phe-L-Arg-L-Trp-L-Cys-NH$_2$ | 1 | 98 | 91 |
| PL-1582 | ReO[V] | Ac-L-Nle-L-Ala-L-His-D-Phe-L-Cys-L-Arg-L-Trp-NH$_2$ | 1 | 66 | 93 |
| PL-1583 | ReO[V] | Ac-L-Nle-L-Ala-L-His-L-Cys-D-Phe-L-Arg-L-Trp-NH$_2$ | 1 | 75 | 84 |
| PL-1584 | ReO[V] | Ac-L-Nle-L-Cys-L-His-D-Phe-L-Ala-L-Arg-L-Trp-NH$_2$ | 1 | 71 | 96 |
| PL-1585 | ReO[V] | Ac-L-Nle-L-Ala-L-His-L-Phe-L-Cys-L-Arg-L-Trp-NH$_2$ | 1 | 22 | 45 |
| PL-1587 | ReO[V] | Ac-L-Nle-L-Arg-L-Arg-D-Nal 2-L-Cys-L-Trp-NH$_2$ | 1 | 98 | 96 |
| PL-1592 | ReO[V] | Ac-L-Nle-L-Ala-L-Arg-L-His-D-Phe-L-Cys-L-Trp-NH$_2$ | 1 | 7 | 19 |
| PL-1593 | ReO[V] | Ac-L-Nle-L-Ala-D-Arg-L-His-D-Phe-L-Cys-L-Trp-NH$_2$ | 1 | 16 | 71 |
| PL-1594 | ReO[V] | Ac-L-Nle-L-Ala-L-His-D/L-Atc-L-Arg-L-Cys-L-Trp-NH$_2$ | 1 | 24 | 100 |

TABLE 1-continued

Melanocortin Receptor Screening Results: Receptor Binding Assay

| Compound ID | Metal ion/ Linear peptide | Sequence Structure | Conc. Cut off (µM) | % Inhibition MC4-R | MC1-R (B-16) |
|---|---|---|---|---|---|
| PL-1595 | ReO[V] | Ac-L-Nle-L-Ala-L-His-Aic-L-Arg-L-Cys-L-Trp-NH₂ (SEQ ID NO: 49) | 1 | 3 | 60 |
| PL-1597 | ReO[V] | Ac-L-Nle-L-Arg-L-Ala-D/L-Atc-L-Cys-L-Trp-NH₂ | 1 | 11 | 68 |
| PL-1598 | ReO[V] | Ac-L-Nle-L-Arg-L-Ala-D-Qal(2')-L-Cys-L-Trp-NH₂ | 1 | 9 | 22 |
| PL-1605 | ReO[V] | Ac-L-Nle-L-Arg-L-Arg-D-Nal 2-L-Cys-L-Trp-NH₂ | 1 | 100 | 100 |
| PL-1606 | ReO[V] | Ac-L-Nle-L-Arg-L-Ala-Aic-L-Cys-L-Trp-NH₂ (SEQ ID NO: 50) | 1 | 63 | 44 |
| PL-1607 | ReO[V] | Ac-L-Nle-L-Ala-L-His-D-Qal(2')-L-Arg-L-Cys-L-Trp-NH₂ | 1 | 52 | 100 |
| PL-1621 | ReO[V] | Ac-L-Nle-L-Ala-L-His-Achc-L-Arg-L-Cys-L-Trp-NH₂ (SEQ ID NO: 51) | 1 | 34 | 36 |
| PL-1623 | ReO[V] | Ac-L-Nle-L-Ala-L-His-D-Sal-L-Arg-L-Cys-L-Trp-NH₂ | 1 | 55 | 92 |
| PL-1624 | ReO[V] | Ac-L-Nle-L-Arg-L-Ala-D-Sal-L-Cys-L-Trp-NH₂ | 1 | 48 | 25 |
| PL-1626 | ReO[V] | Ac-L-Nle-L-Arg-L-Trp-D-Nal 2-L-Cys-L-Trp-NH₂ | 1 | 54 | 66 |
| PL-1633 | ReO[V] | Ac-L-Nle-D-Arg-L-Arg-D-Nal 2-L-Cys-L-Trp-NH₂ | 1 | 87 | 86 |
| PL-1633 | ReO[V] | Ac-L-Nle-D-Arg-L-Arg-D-Nal 2-L-Cys-L-Trp-NH₂ | 1 | 87 | 91 |
| PL-1634 | ReO[V] | Ac-L-Nle-L-Arg-D-Arg-D-Nal 2-L-Cys-L-Trp-NH₂ | 1 | 50 | 42 |
| PL-1635 | ReO[V] | Ac-L-Nle-L-Arg-L-Ala-Acpc-L-Cys-L-Trp-NH₂ (SEQ ID NO: 52) | 1 | 43 | 14 |
| PL-1636 | ReO[V] | Ac-L-Nle-L-Ala-L-His-Acpc-L-Arg-L-Cys-L-Trp-NH₂ (SEQ ID NO: 53) | 1 | 38 | 20 |
| PL-1638 | ReO[V] | Ac-L-Nle-L-Arg-L-Arg-D-Qal(2')-L-Cys-L-Trp-NH₂ | 1 | 48 | 67 |
| PL-1649 | ReO[V] | Ac-L-His-Gly-Gly-L-Cys-L-Trp-NH₂ (SEQ ID NO: 54) | 10 | 62 | 19 |
| PL-1650 | ReO[V] | Ac-L-His-D-Phe-L-Arg-L-Cys-L-Trp-NH₂ | 10 | 66 | 52 |
| PL-1651 | ReO[V] | Ac-L-His-D-Phe-D-Arg-L-Cys-L-Trp-NH₂ | 10 | 58 | 95 |
| PL-1652 | ReO[V] | Ac-L-His-L-Phe-D-Arg-L-Cys-L-Trp-NH₂ | 10 | 40 | 11 |
| PL-1655 | ReO[V] | Ac-L-His-L-Phe-L-Arg-L-Cys-L-Trp-NH₂ (SEQ ID NO: 8) | 10 | 51 | 45 |
| PL-1658 | ReO[V] | Ac-L-Nle-L-Arg-L-Arg-D-Phe(3,4-diCl)-L-Cys-L-Trp-NH₂ | 1 | 100 | 99 |
| PL-1658 | ReO[V] | Ac-L-Nle-L-Arg-L-Arg-D-Phe(3,4-diCl)-L-Cys-L-Trp-NH₂ | 1 | 97 | 93 |
| PL-1659 | ReO[V] | Ac-L-Nle-L-Lys-L-Lys-D-Nal 2-L-Cys-L-Trp-NH₂ | 1 | 91 | 58 |
| PL-1660 | ReO[V] | Ac-L-Nle-L-Arg-L-Arg-D-Phe-L-Cys-L-Trp-NH₂ | 1 | 67 | 100 |
| PL-1661 | ReO[V] | Ac-L-Nle-L-Cit-L-Cit-D-Nal 2-L-Cys-L-Trp-NH₂ | 1 | 58 | 27 |
| PL-1662 | ReO[V] | Ac-L-Nle-L-Ala-L-Arg-L-Arg-D-Nal 2-L-Cys-L-Trp-NH₂ | 1 | 93 | 69 |
| PL-1663 | ReO[V] | Ac-L-Nle-L-Arg-L-Arg-D-Trp-L-Cys-L-Trp-NH₂ | 1 | 85 | 81 |
| PL-1664 | ReO[V] | Ac-L-Nle-L-Arg-L-Arg-D-Nal 2-L-Cys-NH₂ | 1 | 100 | 96 |
| PL-1665 | ReO[V] | Ac-L-Arg-L-Arg-D-Nal 2-L-Cys-L-Trp-NH₂ | 1 | 93 | 94 |
| PL-1666 | ReO[V] | Ac-L-Nle-L-Arg-L-Arg-D-Phe(p-I)-L-Cys-L-Trp-NH₂ | 1 | 101 | 101 |
| PL-1667 | ReO[V] | Heptanoyl-L-Arg-L-Arg-D-Nal 2-L-Cys-L-Trp-NH₂ | 1 | 97 | 92 |
| PL-1684 | ReO[V] | Ac-L-Val-L-Pro-L-Arg-L-Ala-D-Nal 2-L-Cys-L-Trp-NH₂ | 1 | 36 | 26 |
| PL-1685 | ReO[V] | Ac-L-Nle-L-Arg-BAla-D-Nal 2-L-Cys-L-Trp-NH₂ | 1 | 83 | 54 |
| PL-1686 | ReO[V] | Ac-L-Nle-D-Arg-D-Arg-L-Nal-L-Cys-L-Trp-NH₂ | 1 | 24 | 23 |
| PL-1690 | ReO[V] | Ac-L-Nle-D-Arg-L-Arg-D-Nal 2-L-Cys-L-Trp-NH₂ | 1 | 94 | 71 |
| PL-1691 | Linear | Heptanoyl-L-His-D-Phe-L-Arg-L-Cys-L-Trp-L-Lys-NH₂ | 1 | 90 | 62 |
| PL-1692 | Linear | NH₂-(CH₂)₅-CO-L-His-D-Phe-L-Arg-L-Cys-L-Trp-L-Lys-NH₂ | 1 | 79 | 60 |
| PL-1694 | ReO[V] | Heptanoyl-L-His-D-Phe-L-Arg-L-Cys-L-Trp-L-Lys-NH₂ | 1 | 43 | 61 |
| PL-1695 | ReO[V] | NH₂-(CH₂)₅-CO-L-His-D-Phe-L-Arg-L-Cys-L-Trp-L-Lys-NH₂ | 1 | 44 | 87 |
| PL-1702 | ReO[V] | Ac-L-His-L-Arg-L-Arg-D-Nal 2-L-Cys-NH₂ | 1 | 83 | 62 |
| PL-1703 | ReO[V] | Ac-L-Trp-L-Arg-L-Arg-D-Nal 2-L-Cys-NH₂ | 1 | 95 | 73 |
| PL-1704 | ReO[V] | Ac-L-Phe-L-Arg-L-Arg-D-Nal 2-L-Cys-NH₂ | 1 | 98 | 75 |
| PL-1705 | ReO[V] | Ac-L-Lys-L-Arg-L-Arg-D-Nal 2-L-Cys-NH₂ | 1 | 90 | 53 |
| PL-1706 | ReO[V] | Ac-L-Ser-L-Arg-L-Arg-D-Nal 2-L-Cys-NH₂ | 1 | 89 | 60 |
| PL-1707 | ReO[V] | Ac-L-Glu-L-Arg-L-Arg-D-Nal 2-L-Cys-NH₂ | 1 | 46 | 36 |
| PL-1708 | ReO[V] | Ac-L-Arg-L-His-L-Cys-D-Nal 2-L-Arg-L-Trp-NH₂ | 1 | 99 | 34 |
| PL-1709 | ReO[V] | Ac-D-Ala-L-His-L-Cys-L-Arg-D-Nal 2-L-Arg-L-Trp-NH₂ | 1 | 100 | 98 |
| PL-1710 | ReO[V] | Ac-D-Ala-L-Arg-L-Cys-D-Nal 2-L-Arg-L-Trp-NH₂ | 1 | 99 | 25 |
| PL-1718 | ReO[V] | Ac-L-Nle-L-Arg-L-Ala-D-Phe(3-Cl)-L-Cys-L-Trp-NH₂ | 1 | 59 | 35 |
| PL-1722 | ReO[V] | Ac-L-Trp-L-Arg-L-Arg-D-Phe-L-Cys-NH₂ | 1 | 29 | 38 |
| PL-1723 | ReO[V] | Ac-L-Nle-L-Arg-L-Arg-D-Nal 2-L-Cys-OH | 1 | 85 | 66 |
| PL-1726 | ReO[V] | Ac-L-Nle-L-Arg-L-Hphe-D-Phe(4-Cl)-L-Cys-NH₂ | 1 | 70 | 42 |
| PL-1727 | ReO[V] | Ac-L-Nle-L-Arg-L-Pal 2'-D-Phe(4-Cl)-L-Cys-NH₂ | 1 | 84 | 62 |
| PL-1728 | ReO[V] | Ac-L-Nle-L-Arg-L-Phe-D-Phe(4-Cl)-L-Cys-NH₂ | 1 | 73 | 53 |
| PL-1730 | ReO[V] | Ac-L-Nle-L-Arg-L-Nal 1-D-Phe(4-Cl)-L-Cys-NH₂ | 1 | 35 | 39 |
| PL-1731 | ReO[V] | Ac-L-Nle-L-Arg-L-Nal 2-D-Phe(4-Cl)-L-Cys-NH₂ | 1 | 63 | 38 |
| PL-1732 | ReO[V] | Ac-L-Nle-L-Arg-L-Trp-D-Phe(4-Cl)-L-Cys-NH₂ | 1 | 74 | 53 |
| PL-1733 | ReO[V] | L-Tic-D-Phe(4-Cl)-L-Cys-NH₂ | 1 | 8 | 14 |
| PL-1734 | ReO[V] | L-Tic-D-Phe(4-Cl)-L-Trp-L-Cys-NH₂ | 1 | 7 | 6 |
| PL-1735 | ReO[V] | L-Tic-D-Phe(4-Cl)-L-Cys-L-Trp-NH₂ | 1 | 13 | 12 |
| PL-1736 | ReO[V] | Ac-D-Ala-L-His-L-Cys-D-(N-Bzl)Phe-L-Arg-L-Trp-NH₂ | 1 | 3 | 6 |
| PL-1737 | ReO[V] | Ac-D-Ala-L-His-L-Cys-L-(N-Bzl)Phe-L-Arg-L-Trp-NH₂ | 1 | 3 | 48 |
| PL-1738 | ReO[V] | Ac-D-Ala-L-His-L-Cys-D-(N-Bzl)Nal 2-L-Arg-L-Trp-NH₂ | 1 | 23 | 13 |
| PL-1751 | ReO[V] | Ac-L-His-L-(N-2'naphthalene)Phe-L-Arg-L-Trp-L-Cys-NH₂ (SEQ ID NO: 55) | 1 | 70 | 78 |
| PL-1752 | ReO[V] | Ac-D-Ala-L-His-L-Cys-L-(N-2'naphthalene)Phe-L-Arg-L-Trp-NH₂ | 1 | 5 | 29 |
| PL-1753 | ReO[V] | Ac-D-Ala-L-His-L-Cys-D-(N-2'naphthalene)Phe-L-Arg-L-Trp-NH₂ | 1 | 22 | 50 |
| PL-1754 | ReO[V] | D-Tic-D-Phe(4-Cl)-L-Trp-L-Cys-NH₂ | 1 | 7 | 4 |
| PL-1755 | ReO[V] | Ac-L-Arg-L-Lys-L-Phe-D-Phe(4-Cl)-L-Cys-L-Trp-NH₂ | 1 | 40 | 48 |
| PL-1756 | ReO[V] | Ac-L-Nle-L-Lys-L-Phe-D-Phe(4-Cl)-L-Cys-L-Trp-NH₂ | 1 | 63 | 64 |
| PL-1757 | ReO[V] | Ac-L-Arg-L-Lys-L-Leu-D-Phe(4-Cl)-L-Cys-L-Trp-NH₂ | 1 | 45 | 38 |
| PL-1758 | ReO[V] | Ac-L-Nle-L-Lys-L-Leu-D-Phe(4-Cl)-L-Cys-L-Trp-NH₂ | 1 | 94 | 78 |

TABLE 1-continued

Melanocortin Receptor Screening Results: Receptor Binding Assay

| Compound ID | Metal ion/ Linear peptide | Sequence Structure | Conc. Cut off (μM) | % Inhibition MC4-R | MC1-R (B-16) |
|---|---|---|---|---|---|
| PL-1759 | ReO[V] | Ac-L-Arg-L-Phe-L-Lys-D-Phe(4-Cl)-L-Cys-L-Trp-NH$_2$ | 1 | 62 | 61 |
| PL-1760 | ReO[V] | Ac-L-Nle-L-Phe-L-Lys-D-Phe(4-Cl)-L-Cys-L-Trp-NH$_2$ | 1 | 72 | 84 |
| PL-1761 | ReO[V] | Ac-L-Arg-L-Leu-L-Lys-D-Phe(4-Cl)-L-Cys-L-Trp-NH$_2$ | 1 | 16 | 51 |
| PL-1762 | ReO[V] | Ac-L-Nle-L-Leu-L-Lys-D-Phe(4-Cl)-L-Cys-L-Trp-NH$_2$ | 1 | 69 | 82 |
| PL-1774 | ReO[V] | Ac-L-Nle-L-Lys-L-Val-D-Phe(4-Cl)-L-Cys-L-Trp-NH$_2$ | 1 | 83 | 79 |
| PL-1775 | ReO[V] | Ac-L-Nle-L-Lys-L-Ile-D-Phe(4-Cl)-L-Cys-L-Trp-NH$_2$ | 1 | 78 | 57 |
| PL-1776 | ReO[V] | Ac-L-Nle-L-Lys-L-Nle-D-Phe(4-Cl)-L-Cys-L-Trp-NH$_2$ | 1 | 76 | 33 |
| PL-1777 | ReO[V] | Ac-L-Nle-L-Lys-L-Thr-D-Phe(4-Cl)-L-Cys-L-Trp-NH$_2$ | 1 | 79 | 86 |
| PL-1778 | ReO[V] | Ac-L-Nle-L-Lys-L-Tle-D-Phe(4-Cl)-L-Cys-L-Trp-NH$_2$ | 1 | 89 | 60 |
| PL-1779 | ReO[V] | Ac-L-Nle-L-Lys-L-Chg-D-Phe(4-Cl)-L-Cys-L-Trp-NH$_2$ | 1 | 85 | 71 |
| PL-1780 | ReO[V] | Ac-L-Nle-L-Lys-L-Cha-D-Phe(4-Cl)-L-Cys-L-Trp-NH$_2$ | 1 | 77 | 34 |
| PL-1781 | ReO[V] | Ac-L-Nle-L-Lys-L-Trp-D-Phe(4-Cl)-L-Cys-L-Trp-NH$_2$ | 1 | 69 | 66 |
| PL-1782 | ReO[V] | Ac-L-Nle-L-Lys-L-Hphe-D-Phe(4-Cl)-L-Cys-L-Trp-NH$_2$ | 1 | 67 | 14 |
| PL-1783 | ReO[V] | Ac-L-Nle-L-Lys-L-Lys(Z)-D-Phe(4-Cl)-L-Cys-L-Trp-NH$_2$ | 1 | 72 | 87 |
| PL-1785 | ReO[V] | Ac-D-Ala-L-His-L-Cys-D-Tic-L-Arg-L-Trp-NH$_2$ | 1 | 16 | 51 |
| PL-1787 | ReO[V] | Ac-D-Ala-L-His-L-Cys-D-3,3-Dip-L-Arg-L-Trp-NH$_2$ | 1 | 31 | 49 |
| PL-1788 | ReO[V] | Ac-L-Ala-L-His-D-Phe-L-Arg-L-Trp-L-Cys-NH$_2$ | 1 | 78 | 62 |
| PL-1789 | ReO[V] | Ac-L-Pro-L-Ala-L-His-D-Phe-L-Arg-L-Trp-L-Cys-NH$_2$ | 1 | 87 | 63 |
| PL-1790 | ReO[V] | Ac-L-Nle-L-Ala-L-His-D-Phe-L-Arg-L-Trp-L-Cys-L-Trp-NH$_2$ | 1 | 99 | 93 |
| PL-1791 | ReO[V] | Ac-L-Nle-L-Ala-L-His-D-Phe-L-Arg-L-Trp-L-Cys-L-Leu-NH$_2$ | 1 | 98 | 87 |
| PL-1792 | ReO[V] | Ac-L-Nle-L-Ala-L-His-D-Phe-L-Arg-L-Trp-L-Cys-L-Lys-NH$_2$ | 1 | 100 | 96 |
| PL-1793 | ReO[V] | Ac-L-Pro-L-His-D-Phe-L-Arg-D-Trp-L-Cys-NH$_2$ | 1 | 39 | 41 |
| PL-1794 | ReO[V] | Ac-L-Pro-L-His-D-Phe-L-Arg-D-Trp-L-Cys-D-Trp-NH$_2$ | 1 | 20 | -7 |
| PL-1795 | ReO[V] | Ac-D-Tic-D-Phe-L-Arg-D-Trp-L-Cys-NH$_2$ | 1 | 85 | 51 |
| PL-1796 | ReO[V] | Ac-D(3,3)Bpa-D-Phe-L-Arg-D-Trp-L-Cys-NH$_2$ | 1 | 14 | -7 |
| PL-1797 | ReO[V] | Ac-L-Lys-L-Leu-D-Phe(4-Cl)-L-Cys-L-Trp-NH$_2$ | 1 | 42 | 49 |
| PL-1798 | ReO[V] | Heptanoyl-L-Lys-L-Leu-D-Phe(4-Cl)-L-Cys-L-Trp-NH$_2$ | 1 | 56 | 68 |
| PL-1799 | ReO[V] | Ac-L-Nle-L-Lys-L-Leu-D-Phe(4-Cl)-L-Cys-NH$_2$ | 1 | 69 | 70 |
| PL-1800 | ReO[V] | Ac-L-Nle-L-Lys-L-Leu-D-Phe(4-Cl)-D-Cys-L-Trp-NH$_2$ | 1 | 35 | 54 |
| PL-1801 | ReO[V] | Ac-L-Nle-L-Lys-L-Leu-D-Phe(4-Cl)-L-Cys-L-Tic-NH$_2$ | 1 | 64 | 89 |
| PL-1802 | ReO[V] | Ac-L-Nle-L-Lys-L-Leu-D-Phe(4-Cl)-L-Cys-L-Tyr-NH$_2$ | 1 | 16 | 72 |
| PL-1803 | ReO[V] | Ac-L-Nle-L-Lys-L-Leu-D-Phe(4-Cl)-L-Cys-L-Leu-NH$_2$ | 1 | 23 | 55 |
| PL-1804 | ReO[V] | Ac-L-Nle-L-Lys-L-Leu-D-Phe(4-Cl)-L-Cys-L-Tyr(Bzl)-NH$_2$ | 1 | 47 | 70 |
| PL-1805 | ReO[V] | Ac-L-Nle-L-Lys-L-Leu-D-Phe(4-Cl)-L-Cys-L-Phe(3-Cl)-NH2 | 1 | 67 | 74 |
| PL-1806 | ReO[V] | Ac-L-Nle-L-Ala-L-His-L-Phe-L-Arg-L-Cys-L-Trp-NH$_2$ | 1 | 13.0 | 66.0 |
| PL-1807 | ReO[V] | Ac-L-Nle-L-Glu-L-His-D-Phe-L-Arg-L-Cys-L-Trp-NH$_2$ | 1 | 38.0 | 96.0 |
| PL-1808 | ReO[V] | Ac-L-His-D-Phe-L-Arg-L-Trp-L-Cys-L-Lys-L-Pro-L-Val-NH$_2$ | 1 | 75.0 | 94.0 |
| PL-1809 | ReO[V] | L-Tyr-L-Val-L-Nle-Gly-L-His-L-Phe-L-Arg-L-Trp-L-Asp-L-Arg-L-Cys-L-Phe-NH$_2$ (SEQ ID NO: 56) | 1 | 77.0 | 88.0 |
| PL-1810 | ReO[V] | L-Tyr-L-Val-L-Nle-Gly-L-His-L-Phe-L-Arg-L-Trp-L-Asp-L-Cys-L-Arg-L-Phe-NH$_2$ (SEQ ID NO: 57) | 1 | 88.0 | 91.0 |
| PL-1811 | ReO[V] | L-Tyr-L-Val-L-Nle-Gly-L-His-L-Phe-L-Arg-L-Trp-L-Cys-L-Asp-L-Arg-L-Phe-NH$_2$ (SEQ ID NO: 58) | 1 | 92.0 | 95.0 |
| PL-1812 | ReO[V] | L-Tyr-L-Val-L-Nle-Gly-L-His-L-Phe-L-Cys-L-Trp-L-Asp-L-Arg-L-Phe-NH$_2$ (SEQ ID NO: 59) | 1 | 98.0 | 98.0 |
| PL-1813 | ReO[V] | L-Tyr-L-Val-L-Nle-Gly-L-His-L-Phe-L-Cys-L-Arg-L-Trp-L-Asp-L-Arg-L-Phe-NH$_2$ (SEQ ID NO: 60) | 1 | 36.0 | 67.0 |
| PL-1814 | ReO[V] | L-Tyr-L-Val-L-Nle-Gly-L-His-L-Cys-L-Phe-L-Arg-L-Trp-L-Asp-L-Arg-L-Phe-NH$_2$ (SEQ ID NO: 61) | 1 | 26.0 | 62.0 |
| PL-1815 | ReO[V] | L-Tyr-L-Val-L-Nle-Gly-L-Cys-L-His-Phe-L-Arg-L-Trp-L-Asp-L-Arg-L-Phe-NH$_2$ (SEQ ID NO: 62) | 1 | 36.0 | 60.0 |
| PL-1816 | ReO[V] | Heptanoyl-L-Ser(Bzl)-D-Phe(2-Cl)-L-Arg-D-Trp-L-Cys-NH$_2$ | 1 | 83.0 | 46.0 |
| PL-1817 | ReO[V] | Bz-L-His-Gly-D-Phe(2-Cl)-L-Arg-D-Trp-L-Cys-NH$_2$ | 1 | 68.0 | 45.0 |
| PL-1818 | ReO[V] | Ac-L-Nle-L-Ala-D-Trp-D-Phe(2-Cl)-L-Arg-D-Trp-L-Cys-NH$_2$ | 1 | 36.0 | 15.0 |
| PL-1819 | ReO[V] | Ac-L-Ala-L-His-D-Phe(2-Cl)-L-Arg-D-Trp-L-Cys-NH$_2$ | 1 | 67.0 | 76.0 |
| PL-1820 | ReO[V] | Bz-D-Phe(2-Cl)-L-Arg-D-Trp-L-Cys-NH$_2$ | 1 | 54.0 | 17.0 |
| PL-1821 | ReO[V] | Lys(Z)-L-Ala-D-Phe-L-Cys-L-Trp-NH$_2$ | 1 | 18 | 43 |
| PL-1822 | ReO[V] | Lys(Z)-L-Ala-D-Phe(2-Cl)-L-Cys-L-Trp-NH$_2$ | 1 | 15 | 24 |
| PL-1823 | ReO[V] | Lys(Z)-L-Ala-D-Phe(3-Cl)-L-Cys-L-Trp-NH$_2$ | 1 | 35 | 11 |
| PL-1824 | ReO[V] | Lys(Z)-L-Ala-D-Phe(4-Cl)-L-Cys-L-Trp-NH$_2$ | 1 | 69 | 34 |
| PL-1825 | ReO[V] | Lys(Z)-L-Ala-D-Phe-(3,4-diCl)-L-Cys-L-Trp-NH$_2$ | 1 | 58 | 15 |
| PL-1828 | ReO[V] | Heptanoyl-L-Tyr-D-Phe(2-Cl)-L-Arg-D-Trp-L-Cys-NH$_2$ | 1 | 29 | 29 |
| PL-1829 | ReO[V] | Heptanoyl-L-Trp-D-Phe(2-Cl)-L-Arg-D-Trp-L-Cys-NH$_2$ | 1 | 18 | 10 |
| PL-1830 | ReO[V] | Heptanoyl-L-Nal 2-D-Phe(2-Cl)-L-Arg-D-Trp-L-Cys-NH$_2$ | 1 | 5 | 11 |
| PL-1831 | ReO[V] | Heptanoyl-L-Bip-D-Phe(2-Cl)-L-Arg-D-Trp-L-Cys-NH$_2$ | 1 | -2 | 13 |
| PL-1832 | ReO[V] | Heptanoyl-L-Phe(3,4-diCl)-D-Phe(2-Cl)-L-Arg-D-Trp-L-Cys-NH$_2$ | 1 | 25 | 12 |
| PL-1833 | ReO[V] | Heptanoyl-L-Tle-D-Phe(2-Cl)-L-Arg-D-Trp-L-Cys-NH$_2$ | 1 | 59 | 49 |
| PL-1834 | ReO[V] | Heptanoyl-L-Cha-D-Phe(2-Cl)-L-Arg-D-Trp-L-Cys-NH$_2$ | 1 | 16 | 46 |
| PL-1835 | ReO[V] | Heptanoyl-L-Phe(p-NO$_2$)-D-Phe-(2-Cl)-L-Arg-D-Trp-L-Cys-NH$_2$ | 1 | 20 | 15 |
| PL-1836 | ReO[V] | Heptanoyl-L-HPhe-D-Phe(2-Cl)-L-Arg-D-Trp-L-Cys-NH$_2$ | 1 | 82 | 50 |
| PL-1837 | ReO[V] | Heptanoyl-L-Tic-D-Phe(2-Cl)-L-Arg-D-Trp-L-Cys-NH$_2$ | 1 | 42 | 24 |
| PL-1838 | ReO[V] | D-Tic-L-Arg-L-Trp-L-Cys-NH$_2$ | 1 | 54 | 74 |

TABLE 1-continued

Melanocortin Receptor Screening Results: Receptor Binding Assay

| Compound ID | Metal ion/ Linear peptide | Sequence Structure | Conc. Cut off (μM) | % Inhibition MC4-R | MC1-R (B-16) |
|---|---|---|---|---|---|
| PL-1839 | ReO[V] | Ac-D-Tic-D-Phe-L-Arg-L-Trp-L-Cys-NH$_2$ | 1 | 11 | 35 |
| PL-1840 | ReO[V] | Ac-L-Tic-D-Phe-L-Arg-L-Trp-L-Cys-NH$_2$ | 1 | 34 | 24 |
| PL-1841 | ReO[V] | Ac-L-Pro-L-His-D-Phe-L-Arg-L-Trp-L-Cys-NH$_2$ | 1 | 34 | 61 |
| PL-1842 | ReO[V] | Ac-L-Nle-L-Ala-L-His-L-Arg-L-Phe-L-Trp-L-Cys-NH$_2$ (SEQ ID NO: 63) | 1 | 2 | 27 |
| PL-1843 | ReO[V] | Ac-L-Nle-L-Ala-L-His-D-Arg-L-Phe-L-Trp-L-Cys-NH$_2$ | 1 | −8 | 16 |
| PL-1844 | ReO[V] | Ac-L-Nle-L-Ala-L-His-D-Phe-L-Arg-L-Trp-D-Cys-L-Trp-NH$_2$ | 1 | 83 | 98 |
| PL-1845 | ReO[V] | Ac-L-Nle-L-Ala-L-His-D-Phe-L-Arg-L-Trp-L-Cys-D-Trp-NH$_2$ | 1 | 96 | 99 |
| PL-1846 | ReO[V] | Ac-L-Nle-L-Ala-L-His-D-Phe-L-Arg-L-Cys-L-Trp-NH$_2$ | 0.1 | 4 | 85 |
| PL-1849 | ReO[V] | C$_6$H$_5$-CO-L-Lys-D-Phe-L-Cys-L-Trp-NH$_2$ | 1 | 12 | 39 |
| PL-1850 | ReO[V] | C$_6$H$_5$-CH~CH-CO-L-Lys-D-Phe-L-Cys-L-Trp-NH$_2$ | 1 | −2 | 24 |
| PL-1851 | ReO[V] | Pyridine-3-CO-L-Lys-D-Phe-L-Cys-L-Trp-NH$_2$ | 1 | −5 | 26 |
| PL-1852 | ReO[V] | Tetralin-2-CO-L-Lys-D-Phe-L-Cys-L-Trp-NH$_2$ | 1 | 0 | 15 |
| PL-1853 | ReO[V] | Naphthalene-1-CO-L-Lys-D-Phe-L-Cys-L-Trp-NH$_2$ | 1 | 9 | 27 |
| PL-1854 | ReO[V] | Naphthalene-2-CO-L-Lys-D-Phe-L-Cys-L-Trp-NH$_2$ | 1 | −6 | 24 |
| PL-1855 | ReO[V] | Lys(Z)-Gly-D-Phe(4-Cl)-L-Cys-L-Trp-NH$_2$ | 1 | 0 | 32 |
| PL-1856 | ReO[V] | Lys(Z)-L-Val-D-Phe(4-Cl)-L-Cys-L-Trp-NH$_2$ | 1 | 31 | 53 |
| PL-1857 | ReO[V] | Lys(Z)-L-Nle-D-Phe(4-Cl)-L-Cys-L-Trp-NH$_2$ | 1 | 32 | 40 |
| PL-1858 | ReO[V] | Lys(Z)-L-Leu-D-Phe(4-Cl)-L-Cys-L-Trp-NH$_2$ | 1 | 31 | 36 |
| PL-1859 | ReO[V] | Ac-L-Phe-L-Phe-L-Cys-L-Tic-L-Lys-NH$_2$ (SEQ ID NO: 64) | 1 | −8 | 9 |
| PL-1860 | ReO[V] | Ac-L-Phe-L-Phe-L-Cys-L-Inp-L-Lys-NH$_2$ (SEQ ID NO: 65) | 1 | 0 | 6 |
| PL-1861 | ReO[V] | Ac-L-Phe-L-Phe-L-Cys-4-Abz-L-Lys-NH$_2$ (SEQ ID NO: 66) | 1 | −14 | 0 |
| PL-1862 | ReO[V] | Ac-L-Phe-L-Phe-L-Cys-3-Abz-L-Lys-NH$_2$ (SEQ ID NO: 67) | 1 | −7 | 17 |
| PL-1863 | ReO[V] | Ac-L-Phe-L-Phe-L-Cys-2-Abz-L-Lys-NH$_2$ (SEQ ID NO: 68) | 1 | 6 | 19 |
| PL-1864 | ReO[V] | Ac-L-Phe-D-Trp-L-Cys-2-Abz-L-Lys-NH$_2$ | 1 | −7 | 17 |
| PL-1865 | ReO[V] | Ac-L-Ser(Bzl)-D-Phe(2-Cl)-L-Arg-D-Trp-L-Cys-NH$_2$ | 1 | 40 | 13 |
| PL-1866 | ReO[V] | Bz-L-Ser(Bzl)-D-Phe(2-Cl)-L-Arg-D-Trp-L-Cys-NH$_2$ | 1 | 30 | 16 |
| PL-1867 | ReO[V] | Heptanoyl-L-Asn-D-Phe(2-Cl)-L-Arg-D-Trp-L-Cys-NH$_2$ | 1 | 60 | 52 |
| PL-1868 | ReO[V] | Heptanoyl-L-Asp-D-Phe(2-Cl)-L-Arg-D-Trp-L-Cys-NH$_2$ | 1 | −3 | 5 |
| PL-1869 | ReO[V] | Heptanoyl-L-Lys(NH-Bz)-D-Phe(2-Cl)-L-Arg-D-Trp-L-Cys-NH$_2$ | 1 | 42 | 25 |
| PL-1870 | ReO[V] | Heptanoyl-D-B-Hphe(4-F)-L-Arg-D-Trp-L-Cys-NH$_2$ | 1 | 11 | 12 |
| PL-1871 | ReO[V] | Heptanoyl-D-B-Hphe(2-Cl)-L-Arg-D-Trp-L-Cys-NH$_2$ | 1 | 3 | 10 |
| PL-1872 | ReO[V] | Ac-D-Ala-L-His-L-Cys-D-Phe(2-Cl)-L-Arg-L-Trp-NH$_2$ | 1 | 79 | 27 |
| PL-1873 | ReO[V] | Ac-L-Nle-L-Ala-L-His-D-Phe-L-Arg-D-Cys-Trp-NH$_2$ | 1 | 31 | 92.6 |
| PL-1874 | ReO[V] | Ac-L-Nle-L-Ala-L-His-D-Phe-L-Arg-L-Trp-D-Cys-D-Trp-NH$_2$ | 1 | 90 | 98 |
| PL-1875 | ReO[V] | 1-Naphthalene-acetyl-L-Lys-L-Ala-D-Phe(4-Cl)-L-Cys-Trp-NH$_2$ | 1 | 77 | 34 |
| PL-1876 | ReO[V] | 2-Naphthalene-acetyl-L-Lys-L-Ala-D-Phe(4-Cl)-L-Cys-Trp-NH$_2$ | 1 | 52 | 8 |
| PL-1877 | ReO[V] | 3-Bromophenyl acetyl-L-Lys-L-Ala-D-Phe(4-I)-L-Cys-Trp-NH$_2$ | 1 | 92 | 31 |
| PL-1878 | ReO[V] | 4-Bromophenyl acetyl-L-Lys-L-Ala-D-Phe(p-I)-L-Cys-Trp-NH$_2$ | 1 | 75 | 53 |
| PL-1879 | ReO[V] | Heptanoyl-L-Ser(Bzl)-D-Phe(3-Cl)-L-Arg-D-Trp-L-Cys-NH$_2$ | 1 | 86 | 28 |
| PL-1880 | ReO[V] | Heptanoyl-L-Ser(Bzl)-D-Phe(3,4-Cl$_2$)-L-Arg-D-Trp-L-Cys-NH$_2$ | 1 | 96 | 18 |
| PL-1881 | ReO[V] | Heptanoyl-L-Ser(Bzl)-D-HPhe-L-Arg-D-Trp-L-Cys-NH$_2$ | 1 | −6 | 16 |
| PL-1882 | ReO[V] | Heptanoyl-L-Ser(Bzl)-D-Tic-L-Arg-D-Trp-L-Cys-NH$_2$ | 1 | −14 | 11 |
| PL-1883 | ReO[V] | Heptanoyl-L-Ser(Bzl)-D-Phe(4-Cl)-L-Arg-D-Trp-L-Cys-NH$_2$ | 1 | 97 | 49 |
| PL-1884 | ReO[V] | Ac-D-Phe-L-His-L-Cys-D-Phe(2-Cl)-L-Arg-L-Trp-NH$_2$ | 1 | 64 | 32 |
| PL-1885 | ReO[V] | Ac-D-Nle-L-His-L-Cys-D-Phe(2-Cl)-L-Arg-L-Trp-NH$_2$ | 1 | 84 | 68 |
| PL-1886 | ReO[V] | Ac-D-HPhe-L-His-L-Cys-D-Phe(2-Cl)-L-Arg-L-Trp-NH$_2$ | 1 | 73 | 62 |
| PL-1887 | ReO[V] | Ac-D-Phe-L-Phe-L-Cys-D-Phe(2-Cl)-L-Arg-L-Trp-NH$_2$ | 1 | 50 | 24 |
| PL-1888 | ReO[V] | Ac-D-Ala-L-Nle-L-Cys-D-Phe(2-Cl)-L-Arg-L-Trp-NH$_2$ | 1 | 90 | 40 |
| PL-1889 | ReO[V] | Ac-L-Nle-L-His-L-Cys-D-Phe(2-Cl)-L-Arg-L-Trp-NH$_2$ | 1 | 49 | 58 |
| PL-1890 | ReO[V] | Heptanoyl-D-Ala-L-His-L-Cys-D-Phe(2-Cl)-L-Arg-L-Trp-NH$_2$ | 1 | 24 | 31 |
| PL-1891 | ReO[V] | Heptanoyl-L-Ser(Bzl)-D-BHphe(2-Cl)-L-Arg-D-Trp-L-Cys-NH$_2$ | 1 | −7 | 10 |
| PL-1892 | ReO[V] | Heptanoyl-L-Ser(Bzl)-D-BHphe(2-F)-L-Arg-D-Trp-L-Cys-NH$_2$ | 1 | 6 | 10 |
| PL-1893 | ReO[V] | Ac-D-Phg-L-His-L-Cys-D-Phe(2-Cl)-L-Arg-L-Trp-NH$_2$ | 1 | 78 | 52 |
| PL-1894 | ReO[V] | Ac-D-Ala-L-Phg-L-Cys-D-Phe(2-Cl)-L-Arg-L-Trp-NH$_2$ | 1 | 81 | 37 |
| PL-1895 | ReO[V] | Ac-D-Ala-L-Phe-L-Cys-D-Phe(2-Cl)-L-Arg-L-Trp-NH$_2$ | 1 | 63 | 19 |
| PL-1896 | ReO[V] | Ac-L-Nle-L-His-L-Cys-D-(NMe)Phe-L-Arg-L-Trp-NH$_2$ | 1 | −1 | 56 |
| PL-1897 | ReO[V] | Heptanoyl-L-Ser(Bzl)-D-Tiq-L-Arg-D-Trp-L-Cys-NH$_2$ | 1 | −24 | 12 |
| PL-1899 | ReO[V] | C$_6$H$_5$(CH$_2$)$_3$-CO-L-Ser(Bzl)-D-(NMe)-Phe-L-Arg-D-Trp-L-Cys-NH$_2$ | 1 | 0 | 19 |
| PL-1900 | ReO[V] | 3-Bromophenyl acetyl-L-Lys-L-Ala-D-Phe-L-Cys-L-Trp-NH$_2$ | 1 | 47 | 10 |
| PL-1901 | ReO[V] | 3-Bromophenyl acetyl-L-Lys-L-Ala-D-Phe-L-Cys-L-Trp-NH$_2$ | 1 | 51 | 26 |
| PL-1902 | ReO[V] | 3-Bromophenyl acetyl-L-Lys-L-Ala-D-Phe(4-Me)-L-Cys-L-Trp-NH$_2$ | 1 | 93 | 17 |
| PL-1903 | ReO[V] | 3-Bromophenyl acetyl-L-Lys-L-Ala-D-Phe(3-Cl)-L-Cys-L-Trp-NH$_2$ | 1 | 71 | 5 |
| PL-1904 | ReO[V] | 3-Bromophenyl acetyl-L-Lys-L-Ala-D-HPhe-L-Cys-L-Trp-NH$_2$ | 1 | 11 | 2 |
| PL-1905 | ReO[V] | 2-Chlorophenyl acetyl-L-Lys-L-Ala-D-Phe(4-Cl)-L-Cys-L-Trp-NH$_2$ | 1 | 86 | 31 |
| PL-1906 | ReO[V] | 4-Chlorophenyl acetyl-L-Lys-L-Ala-D-Phe(4-Cl)-L-Cys-L-Trp-NH$_2$ | 1 | 91 | 68 |
| PL-1907 | ReO[V] | 4-Methylphenyl acetyl-L-Lys-L-Ala-D-Phe(4-Cl)-L-Cys-L-Trp-NH$_2$ | 1 | 69 | 44 |
| PL-1908 | ReO[V] | Indonyl acetyl-L-Lys-L-Ala-D-Phe(4-Cl)-L-Cys-L-Trp-NH$_2$ | 1 | 33 | 8 |
| PL-1909 | ReO[V] | 3-Bromophenyl acetyl-L-Arg-L-Ala-D-Phe(4-Cl)-L-Cys-L-Trp-NH$_2$ | 1 | 95 | 32 |
| PL-1910 | ReO[V] | Heptanoyl-L-Dpr(Bz)-D-Phe(2-Cl)-L-Arg-D-Trp-L-Cys-NH$_2$ | 1 | 23 | 42 |
| PL-1911 | ReO[V] | Heptanoyl-L-Dpr(2'-Naphthalene acetyl)-D-Phe(2-Cl)-L-Arg-D-Trp-L-Cys-NH$_2$ | 1 | −6 | 11 |
| PL-1912 | ReO[V] | Heptanoyl-L-Dpr(1'-Adamantane carbonyl)-D-Phe(2-Cl)-L-Arg-D-Trp-L-Cys-NH$_2$ | 1 | −3 | 2 |
| PL-1913 | ReO[V] | Heptanoyl-L-Dpr(4'-MePhenyl acetyl)-D-Phe(2-Cl)-L-Arg-D-Trp-L-Cys-NH$_2$ | 1 | 22 | 35 |

TABLE 1-continued

Melanocortin Receptor Screening Results: Receptor Binding Assay

| Compound ID | Metal ion/ Linear peptide | Sequence Structure | Conc. Cut off (μM) | % Inhibition MC4-R | % Inhibition MC1-R (B-16) |
|---|---|---|---|---|---|
| PL-1914 | ReO[V] | Heptanoyl-L-Dpr(3'-BrPhenyl acetyl)-D-Phe(2-Cl)-L-Arg-D-Trp-L-Cys-NH$_2$ | 1 | 20 | 53 |
| PL-1915 | ReO[V] | Heptanoyl-L-Ser(Bzl)-D-Phe(2-Cl)-L-Arg-L-Trp-L-Cys-NH$_2$ | 1 | 94 | 72 |
| PL-1916 | ReO[V] | Heptanoyl-L-Ser(Bzl)-D-Phe(2-Cl)-L-Arg-L-His-L-Cys-NH$_2$ | 1 | 9 | 44 |
| PL-1917 | ReO[V] | Heptanoyl-L-Ser(Bzl)-D-Phe(2-Cl)-L-Arg-L-Nal 2'-L-Cys-NH$_2$ | 1 | 94 | 48 |
| PL-1918 | ReO[V] | Heptanoyl-L-Ser(Bzl)-D-Phe(2-Cl)-L-Arg-L-Bip-L-Cys-NH$_2$ | 1 | 10 | 21 |
| PL-1919 | ReO[V] | Heptanoyl-L-Ser(Bzl)-D-Phe(2-Cl)-L-Arg-L-Pal 3'-L-Cys-NH$_2$ | 1 | 17 | 47 |
| PL-1920 | ReO[V] | D-Phe-L-Arg-L-Trp-L-Cys-NH$_2$ | 1 | 52 | 65 |
| PL-1921 | ReO[V] | Ac-D-Phe-L-Arg-L-Trp-L-Cys-NH$_2$ | 1 | 20 | 25 |
| PL-1922 | ReO[V] | Ac-L-Nle-D-Phe-L-Arg-L-Trp-L-Cys-NH$_2$ | 1 | 25 | 28 |
| PL-1923 | ReO[V] | Ac-L-Nle-L-Ala-D-Phe-L-Arg-L-Trp-L-Cys-NH$_2$ | 1 | 68 | 70 |
| PL-1924 | ReO[V] | Ac-L-Pro-D-Phe-L-Arg-L-Trp-L-Cys-NH$_2$ | 1 | 44 | 33 |
| PL-1925 | ReO[V] | Heptanoyl-D-Phe-L-Arg-L-Trp-L-Cys-NH$_2$ | 1 | 6 | 18 |
| PL-1926 | ReO[V] | Bz-L-Arg-L-Trp-L-Cys-NH$_2$ (SEQ ID NO: 69) | 1 | 7 | 25 |
| PL-1927 | ReO[V] | Phenyl acetyl-L-Arg-L-Trp-L-Cys-NH$_2$ | 1 | 8 | 28 |
| PL-1928 | ReO[V] | 3-Phenyl-propanoyl-L-Arg-L-Trp-L-Cys-NH$_2$ | 1 | 8 | 32 |
| PL-1929 | ReO[V] | 4-Phenyl-butanoyl-L-Arg-L-Trp-L-Cys-NH$_2$ | 1 | 2 | 18 |
| PL-1930 | ReO[V] | t-Cinnamoyl-L-Arg-L-Trp-L-Cys-NH$_2$ | 1 | −20 | 9 |
| PL-1931 | ReO[V] | 1-Naphthyl-acetyl-L-Arg-L-Trp-L-Cys-NH$_2$ | 10 | 92 | 47 |
| PL-1932 | ReO[V] | 2-Naphthyl-acetyl-L-Arg-L-Trp-L-Cys-NH$_2$ | 1 | 1 | 16 |
| PL-1933 | ReO[V] | 1-Naphthoyl-L-Arg-L-Trp-L-Cys-NH$_2$ | 1 | 0 | 14 |
| PL-1934 | ReO[V] | 2-Naphthoyl-L-Arg-L-Trp-L-Cys-NH$_2$ | 1 | 6 | 34 |
| PL-1935 | ReO[V] | Heptanoyl-L-Arg-L-Trp-L-Cys-NH$_2$ | 1 | 8 | 39 |
| PL-1936 | ReO[V] | Heptanoyl-L-Ser(Bzl)-D-Phe(4-F)-L-Arg-L-Trp-L-Cys-NH$_2$ | 1 | 81 | 71 |
| PL-1937 | ReO[V] | Heptanoyl-L-Ser(Bzl)-D-Phe(penta-F)-L-Arg-L-Trp-L-Cys-NH$_2$ | 1 | 91 | 65 |
| PL-1938 | ReO[V] | Heptanoyl-L-Ser(Bzl)-D-Pal(2)-L-Arg-L-Trp-L-Cys-NH$_2$ | 1 | 16 | 16 |
| PL-1939 | ReO[V] | Heptanoyl-L-Ser(Bzl)-D-Phe(2-Br)-L-Arg-L-Trp-L-Cys-NH$_2$ | 1 | 91 | 73 |
| PL-1940 | ReO[V] | Ac-D-Ala-L-Nle-L-Cys-D-Phe(2-Cl)-L-Arg-L-Trp-NH$_2$ | 1 | 89 | 26 |
| PL-1941 | ReO[V] | Heptanoyl-L-Ser(Bzl)-D-Phe(2-Cl)-L-Lys-L-Nal 2-L-Cys-NH$_2$ | 1 | 90 | 25 |
| PL-1942 | ReO[V] | Heptanoyl-L-Ser(Bzl)-D-Phe(2-Cl)-L-Arg-L-Nal 1-L-Cys-NH$_2$ | 1 | 53 | 16 |
| PL-1943 | ReO[V] | Heptanoyl-L-Ser(Bzl)-D-Phe(penta-F)-L-Arg-L-Nal 2-L-Cys-NH$_2$ | 1 | 93 | 64 |
| PL-1944 | ReO[V] | Heptanoyl-L-Ser(Bzl)-D-Phe(penta-F)-L-Lys-L-Nal 2-L-Cys-NH$_2$ | 1 | 80 | 40 |
| PL-1945 | ReO[V] | Heptanoyl-L-Hyp(Bzl)-D-Phe(2-Cl)-L-Arg-L-Nal 2-L-Cys-NH$_2$ | 1 | 94 | 30 |
| PL-1946 | ReO[V] | Heptanoyl-[(2S,3R),5-phenyl pyrrolidinyl-2-carbonyl]-D-Phe(2-Cl)-L-Arg-L-Nal 2-L-Cys-NH$_2$ | 1 | 81 | 24 |
| PL-1947 | ReO[V] | Heptanoyl-L-Ser(Bzl)-D-Phe(CF$_3$)-L-Arg-L-Trp-L-Cys-NH$_2$ | 1 | 98 | 23 |
| PL-1948 | ReO[V] | Heptanoyl-L-Ser(Bzl)-D-Phe(CH$_3$)-L-Arg-L-Trp-L-Cys-NH$_2$ | 1 | 98 | 50 |
| PL-1949 | ReO[V] | Heptanoyl-L-Ser(Bzl)-D-Phe(4-Cl)-L-Arg-L-Trp-L-Cys-NH$_2$ | 1 | 99 | 77 |
| PL-1950 | ReO[V] | Heptanoyl-L-Ser(Bzl)-D-Phe(3-Cl)-L-Arg-L-Trp-L-Cys-NH$_2$ | 1 | 92 | 37 |
| PL-1951 | ReO[V] | Ac-D-Val-L-His-L-Cys-D-Phe(2-Cl)-L-Arg-L-Trp-NH$_2$ | 1 | 60 | 32 |
| PL-1952 | ReO[V] | Ac-D-Ala-L-Chg-L-Cys-D-Phe(2-Cl)-L-Arg-L-Trp-NH$_2$ | 1 | 88 | 46 |
| PL-1953 | ReO[V] | Ac-D-Ala-L-Val-L-Cys-D-Phe(2-Cl)-L-Arg-L-Trp-NH$_2$ | 1 | 69 | 19 |
| PL-1955 | ReO[V] | Ac-D-Chg-L-His-L-Cys-D-Phe(2-Cl)-L-Arg-L-Trp-NH$_2$ | 1 | 76 | 68 |
| PL-1956 | ReO[V] | Ac-D-Cha-L-His-L-Cys-D-Phe(2-Cl)-L-Arg-L-Trp-NH$_2$ | 1 | 58 | 64 |
| PL-1957 | ReO[V] | Ac-D-Leu-L-His-L-Cys-D-Phe(2-Cl)-L-Arg-L-Trp-NH$_2$ | 1 | 66 | 53 |
| PL-1958 | ReO[V] | Ac-D-Val-L-Phg-L-Cys-D-Phe(2-Cl)-L-Arg-L-Trp-NH$_2$ | 1 | 60 | 31 |
| PL-1959 | ReO[V] | Ac-D-Chg-L-Phg-L-Cys-D-Phe(2-Cl)-L-Arg-L-Trp-NH$_2$ | 1 | 55 | 27 |
| PL-1960 | ReO[V] | Ac-D-Cha-L-Phg-L-Cys-D-Phe(2-Cl)-L-Arg-L-Trp-NH$_2$ | 1 | 38 | 16 |
| PL-1961 | ReO[V] | Ac-D-Leu-L-Phg-L-Cys-D-Phe(2-Cl)-L-Arg-L-Trp-NH$_2$ | 1 | 77 | 38 |
| PL-1962 | ReO[V] | Ac-D-Val-L-Phe-L-Cys-D-Phe(2-Cl)-L-Arg-L-Trp-NH$_2$ | 1 | 47 | 23 |
| PL-1963 | ReO[V] | Ac-D-Chg-L-Phe-L-Cys-D-Phe(2-Cl)-L-Arg-L-Trp-NH$_2$ | 1 | 31 | 27 |
| PL-1964 | ReO[V] | Ac-D-Cha-L-Phe-L-Cys-D-Phe(2-Cl)-L-Arg-L-Trp-NH$_2$ | 1 | 28 | 38 |
| PL-1965 | ReO[V] | Ac-D-Leu-L-Phe-L-Cys-D-Phe(2-Cl)-L-Arg-L-Trp-NH$_2$ | 1 | 62 | 46 |
| PL-1970 | ReO[V] | Phenylacetyl-L-Arg-L-Ala-D-Phe(4-Cl)-L-Cys-D-Trp-NH$_2$ | 1 | 92 | 51 |
| PL-1971 | ReO[V] | 3'-bromophenylacetyl-L-Arg-D-Ala-Dphe(4-Cl)-L-Cys-L-Trp-NH$_2$ | 1 | 33 | 67 |
| PL-1972 | ReO[V] | Phenylacetyl-D-Arg-L-Ala-D-Phe(4-Cl)-L-Cys-L-Trp-NH$_2$ | 1 | 17 | 27 |

For selected peptides of this invention, a cAMP assay was also performed. Human MC4-R or B-16 cells were grown to confluence in 96 well plates (plating approximately 250,000 cells per well). Identical sets of cells in triplicate were treated with 0.2 mM isobutylmethylxanthine (IBMX) and the chosen concentration of the rhenium metal ion-complexed peptide and the rhenium metal ion-complexed peptide in the presence of 20 nM alpha-MSH. Cells similarly treated but with only 20 nM alpha-MSH served as positive control. A buffer blank, as a negative control, was also included. Incubation was for one hour at 37° C. after which the medium was aspirated and the cells extarted with 150 microliters of HCl. Total cAMP accumulated in 100 microliters of this solution was quantitated using a commercially available low pH cAMP assay kit (R&D Systems) by the procedure specified by the kit supplier. The table shows the amount of cAMP accumulated in the cells upon exposure to the test compound alone and the presence of 20 nM alpha-MSH. The rhenium metal ion-complexed peptide showing cAMP accumulation in the same range as or higher than the positive control (buffer blank in the presence of alpha-MSH) are considered to be agonist ligands. The rhenium metal ion-complexed peptide showing accumulation in the same range as the negative control (buffer blank in the absence of alpha-MSH) are ineffective at the test concentration if the result is similar to the positive control where alpha-MSH is also present in the assay. The rhenium metal ion-complexed peptide showing accumulation in the same range as the negative control are considered to be antagonists if there is inhibition in cAMP when alpha-MSH is present in the assay. Values above the positive control are due to potent agonism, experimental variance or synergistic agonistic effects of rhenium metal ion-complexed peptide and alpha-MSH.

TABLE 2

Evaluation of MC-specific metallopeptides of the primary structure of Table 1 in cAMP stimulation assay in presence and absence of natural stimulator α-MSH

| ID | METAL ION | µM Concentration | cAMP Accumulation (pMol/ml) | |
|---|---|---|---|---|
| | | | Absence of α-MSH | Presence of α-MSH |
| Buffer blank | | | 1 | 99 |
| PL-815 | ReO[V] | 10 | 55 | 178 |
| PL-836 | ReO[V] | 10 | 0.31 | 68 |
| PL-837 | ReO[V] | 10 | 9 | 63 |
| PL-838 | ReO[V] | 10 | 2 | 53 |
| PL-1102 | ReO[V] | 10 | 2 | 113 |
| PL-1113 | ReO[V] | 10 | 123 | 67 |
| PL-1145 | ReO[V] | 10 | 221 | 277 |
| PL-1160 | ReO[V] | 10 | 18. | 34 |
| PL-1165 | ReO[V] | 10 | 15 | 71 |
| PL-1179 | ReO[V] | 10 | 7 | 50 |
| PL-1183 | ReO[V] | 1 | 42 | 39 |
| PL-1185 | ReO[V] | 1 | 30 | 22 |
| PL-1189 | ReO[V] | 1 | 52 | 34 |
| PL-1190 | ReO[V] | 1 | 63 | 148 |
| PL-1191 | ReO[V] | 1 | 8 | 94 |
| PL-1207 | ReO[V] | 1 | 4 | 3 |
| PL-1208 | ReO[V] | 10 | 2 | 2 |
| PL-1209 | ReO[V] | 1 | 5 | 13 |
| PL-1210 | ReO[V] | 1 | 8 | 5 |
| PL-1211 | ReO[V] | 1 | 10 | 8 |
| PL-1222 | ReO[V] | 50 | 177 | 346 |
| PL-1223 | ReO[V] | 10 | 63 | 85 |
| PL-1233 | ReO[V] | 10 | 19 | 21 |
| PL-1235 | ReO[V] | 10 | 29 | 28 |
| PL-1236 | ReO[V] | 10 | 11 | 30 |
| PL-1237 | ReO[V] | 10 | 96 | 116 |
| PL-1238 | ReO[V] | 10 | 26 | 140 |
| PL-1239 | ReO[V] | 10 | 108 | 131 |
| PL-1249 | ReO[V] | 10 | 4 | 139 |
| PL-1250 | ReO[V] | 10 | 2 | 15 |
| PL-1251 | ReO[V] | 10 | 7 | 21 |
| PL-1255 | ReO[V] | 10 | 2 | 2 |
| PL-1256 | ReO[V] | 1 | 17 | 71 |
| PL-1258 | ReO[V] | 10 | 9 | 63 |
| PL-1259 | ReO[V] | 1 | 131 | 131 |
| PL-1260 | ReO[V] | 1 | 5 | 6 |
| PL-1261 | ReO[V] | 1 | 189 | 214 |
| PL-1264 | ReO[V] | 1 | 1 | 11 |
| PL-1265 | ReO[V] | 1 | 3 | 127 |
| PL-1266 | ReO[V] | 1 | 2 | 131 |
| PL-1268 | ReO[V] | 1 | 18 | 16 |
| PL-1269 | ReO[V] | 1 | 4 | 2 |
| PL-1270 | None | 1 | 139 | 123 |
| PL-1272 | None | 1 | 80 | 75 |
| PL-1276 | ReO[V] | 1 | 3 | 12 |
| PL-1281 | ReO[V] | 1 | 158 | 25 |
| PL-1285 | ReO[V] | 1 | 148 | 158 |
| PL-1292 | ReO[V] | 1 | 3 | 13 |
| PL-1293 | ReO[V] | 1 | 3 | 6 |
| PL-1294 | ReO[V] | 1 | 43 | 91 |
| PL-1295 | R O[V] | 1 | 136 | 122 |
| PL-1298 | ReO[V] | 1 | 1 | 32 |
| PL-1297 | ReO[V] | 1 | 3 | 7 |
| PL-1301 | ReO[V] | 1 | 1 | 23 |
| PL-1302 | ReO[V] | 1 | 12 | 43 |
| PL-1303 | ReO[V] | 1 | 2 | 59 |
| PL-1305 | ReO[V] | 1 | 2 | 3 |
| PL-1306 | ReO[V] | 1 | 189 | 158 |
| PL-1329 | ReO[V] | 1 | 1 | 63 |
| PL-1332 | ReO[V] | 1 | 0 | 103 |

TABLE 2-continued

Evaluation of MC-specific metallopeptides of the primary structure of Table 1 in cAMP stimulation assay in presence and absence of natural stimulator α-MSH

| ID | METAL ION | µM Concentration | cAMP Accumulation (pMol/ml) | |
|---|---|---|---|---|
| | | | Absence of α-MSH | Presence of α-MSH |
| PL-1335 | ReO[V] | 1 | 0 | 3 |
| PL-1340 | ReO[V] | 1 | 3 | 7 |
| PL-1342 | ReO[V] | 10 | 43 | 59 |
| PL-1346 | ReO[V] | 10 | 3 | 76 |
| PL-1347 | ReO[V] | 10 | 2 | 81 |
| PL-1351 | ReO[V] | 10 | 68 | .30 |
| PL-1370 | ReO[V] | 1 | 2 | 16 |
| PL-1372 | ReO[V] | 1 | 13 | 149 |
| PL-1373 | ReO[V] | 1 | 1 | 8 |
| PL-1374 | ReO[V] | 1 | 37 | 73 |
| PL-1387 | None | 1 | 52 | 94 |
| PL-1396 | ReO[V] | 1 | 36 | 120 |
| PL-1438 | ReO[V] | 1 | 113 | 126 |
| PL-1440 | ReO[V] | 1 | 59 | 55 |
| PL-1443 | ReO[V] | 1 | 4 | 34 |
| PL-1451 | ReO[V] | 1 | 9 | 90 |
| PL-1493 | ReO[V] | 1 | 4 | 15 |
| PL-1581 | ReO[V] | 1 | 111 | 132 |
| PL-1658 | ReO[V] | 1 | 10 | 67 |
| PL-1659 | ReO[V] | 1 | 7 | 78 |
| PL-1662 | ReO[V] | 1 | 6 | 96 |
| PL-1663 | ReO[V] | 1 | 55 | 122 |
| PL-1664 | ReO[V] | 1 | 7 | 44 |
| PL-1665 | ReO[V] | 1 | 10 | 70 |
| PL-1666 | ReO[V] | 1 | 15 | 28 |
| PL-1667 | ReO[V] | 1 | 23 | 63 |
| PL-1684 | ReO[V] | 1 | 5 | 110 |
| PL-1685 | ReO[V] | 1 | 7 | 102 |
| PL-1686 | ReO[V] | 1 | 4 | 106 |
| PL-1690 | ReO[V] | 1 | 13 | 76 |
| PL-1691 | None | 1 | 30 | 102 |
| PL-1692 | None | 1 | 18 | 106 |
| PL-1694 | ReO[V] | 1 | 25 | 92 |
| PL-1695 | ReO[V] | 1 | 30 | 101 |
| PL-1702 | ReO[V] | 1 | 4 | 134 |
| PL-1703 | ReO[V] | 1 | 2 | 73 |
| PL-1704 | ReO[V] | 1 | 3 | 73 |
| PL-1705 | ReO[V] | 1 | 2 | 74 |
| PL-1706 | ReO[V] | 1 | 2 | 71 |
| PL-1707 | ReO[V] | 1 | 15 | 156 |
| PL-1708 | ReO[V] | 1 | 13 | 54 |
| PL-1709 | R O[V] | 1 | 33 | 46 |
| PL-1710 | R O[V] | 1 | 3 | 7 |
| PL-1718 | ReO[V] | 1 | 23 | 105 |
| PL-1722 | R O[V] | 1 | 28 | 180 |
| PL-1723 | R O[V] | 1 | 30 | 169 |
| PL-1726 | ReO[V] | 1 | 21 | 171 |
| PL-1727 | ReO[V] | 1 | 27 | 151 |
| PL-1728 | ReO[V] | 1 | 15 | 164 |
| PL-1730 | ReO[V] | 1 | 22 | 111 |
| PL-1731 | ReO[V] | 1 | 19 | 117 |
| PL-1732 | ReO[V] | 1 | 14 | 105 |
| PL-1733 | ReO[V] | 1 | 16 | 114 |
| PL-1734 | ReO[V] | 1 | 13 | 122 |
| PL-1735 | ReO[V] | 1 | 20 | 115 |
| PL-1736 | ReO[V] | 1 | 17 | 152 |
| PL-1737 | ReO[V] | 1 | 53 | 162 |
| PL-1738 | ReO[V] | 1 | 7 | 173 |
| PL-1751 | ReO[V] | 1 | 71 | 96 |
| PL-1752 | ReO[V] | 1 | 4 | 101 |
| PL-1753 | ReO[V] | 1 | 39 | 104 |
| PL-1754 | ReO[V] | 1 | 3 | 100 |
| PL-1755 | ReO[V] | 1 | 21 | 110 |
| PL-1756 | ReO[V] | 1 | 43 | 102 |
| PL-1757 | ReO[V] | 1 | 11 | 96 |
| PL-1758 | ReO[V] | 1 | 34 | 61 |
| PL-1759 | ReO[V] | 1 | 24 | 79 |
| PL-1760 | ReO[V] | 1 | 66 | 80 |
| PL-1761 | ReO[V] | 1 | 11 | 87 |
| PL-1762 | ReO[V] | 1 | 49 | 88 |

TABLE 2-continued

Evaluation of MC-specific metallopeptides of the primary structure of Table 1 in cAMP stimulation assay in presence and absence of natural stimulator α-MSH

| ID | METAL ION | μM Concentration | cAMP Accumulation (pMol/ml) Absence of α-MSH | cAMP Accumulation (pMol/ml) Presence of α-MSH |
|---|---|---|---|---|
| PL-1774 | ReO[V] | 1 | 48 | 163 |
| PL-1775 | ReO[V] | 1 | 53 | 170 |
| PL-1776 | ReO[V] | 1 | 26 | 138 |
| PL-1778 | ReO[V] | 1 | 50 | 141 |
| PL-1779 | ReO[V] | 1 | 47 | 155 |
| PL-1780 | ReO[V] | 1 | 8 | 126 |
| PL-1782 | ReO[V] | 1 | 7 | 108 |
| PL-1788 | ReO[V] | 1 | 189 | 109 |
| PL-1789 | ReO[V] | 1 | 96 | 90 |
| PL-1790 | ReO[V] | 1 | 164 | 149 |
| PL-1791 | ReO[V] | 1 | 163 | 137 |
| PL-1792 | ReO[V] | 1 | 187 | 109 |
| PL-1793 | ReO[V] | 1 | 119 | 98 |
| PL-1794 | ReO[V] | 1 | 4 | 133 |
| PL-1795 | ReO[V] | 1 | 71 | 124 |
| PL-1796 | ReO[V] | 1 | 4 | 133 |
| PL-1799 | ReO[V] | 1 | 9 | 117 |
| PL-1801 | ReO[V] | 1 | 42 | 107 |
| PL-1805 | ReO[V] | 1 | 15 | 78 |
| PL-1806 | ReO[V] | 1 | 10 | 110 |
| PL-1807 | ReO[V] | 1 | 103 | 115 |
| PL-1808 | R O[V] | 1 | 109 | 137 |
| PL-1809 | ReO[V] | 1 | 113 | 130 |
| PL-1810 | ReO[V] | 1 | 101 | 125 |
| PL-1811 | ReO[V] | 1 | 117 | 66 |
| PL-1812 | ReO[V] | 1 | 132 | 93 |
| PL-1813 | ReO[V] | 1 | 36 | 91 |
| PL-1814 | ReO[V] | 1 | 8 | 80 |
| PL-1815 | ReO[V] | 1 | 34 | 119 |
| PL-1816 | ReO[V] | 1 | 69 | 89 |
| PL-1817 | ReO[V] | 1 | 24 | 110 |
| PL-1818 | ReO[V] | 1 | 6 | 96 |
| PL-1819 | ReO[V] | 1 | 93 | 96 |
| PL-1820 | ReO[V] | 1 | 8 | 102 |
| PL-1821 | ReO[V] | 1 | 37 | 88 |
| PL-1822 | ReO[V] | 1 | 13 | 101 |
| PL-1823 | ReO[V] | 1 | 14 | 114 |
| PL-1824 | ReO[V] | 1 | 71 | 124 |
| PL-1825 | ReO[V] | 1 | 4 | 133 |
| PL-1825 | ReO[V] | 1 | 7 | 106 |
| PL-1838 | ReO[V] | 1 | 16 | 65 |
| PL-1839 | ReO[V] | 1 | 63 | 77 |
| PL-1840 | ReO[V] | 1 | 76 | 77 |
| PL-1841 | ReO[V] | 1 | 91 | 81 |
| PL-1842 | ReO[V] | 1 | 25 | 76 |
| PL-1843 | ReO[V] | 1 | 18 | 81 |
| PL-1844 | ReO[V] | 1 | 110 | 81 |
| PL-1845 | ReO[V] | 1 | 82 | 38 |
| PL-1877 | ReO[V] | 1 | 72 | 125 |
| PL-1879 | ReO[V] | 1 | 75 | 108 |
| PL-1880 | ReO[V] | 1 | 16 | 92 |
| PL-1883 | ReO[V] | 1 | 125 | 115 |
| PL-1884 | ReO[V] | 1 | 108 | 158 |
| PL-1885 | ReO[V] | 1 | 135 | 148 |
| PL-1886 | ReO[V] | 1 | 151 | 161 |
| PL-1900 | ReO[V] | 1 | 19 | 87 |
| PL-1902 | ReO[V] | 1 | 56 | 143 |
| PL-1903 | ReO[V] | 1 | 62 | 108 |
| PL-1905 | ReO[V] | 1 | 59 | 96 |
| PL-1906 | ReO[V] | 1 | 68 | 87 |
| PL-1907 | ReO[V] | 1 | 62 | 98 |
| PL-1909 | ReO[V] | 1 | 70 | 81 |
| PL-1915 | ReO[V] | 1 | 123 | 128 |
| PL-1917 | ReO[V] | 1 | 109 | 116 |
| PL-1931 | ReO[V] | 10 | 15 | 79 |
| PL-1144 | ReO[V] | 10 | 215 | 280 |
| PL-1489 | ReO[V] | 1 | 9 | 16 |
| PL-1605 | ReO[V] | 1 | 16 | 15 |

Based on the foregoing studies, potential lead molecules have been identified, including the following:

| | | |
|---|---|---|
| PL-1145 | MC1-R agonist | (Template 2) |
| PL-1144 | MC1-R agonist | (Template 2) |
| PL-1493 | MC4-R antagonist | (Template 1) |
| PL-1883 | MC4-R agonist | (Template 1) |
| PL-1489 | MC4-R antagonist | (Template 5) |
| PL-1950 | MC4-R specific | (Template 5) |
| PL-1947 | MC4-R specific | (Template 5) |
| PL-1581 | Non-specific agonist | (Template 5) |
| PL-1790 | Non-specific agonist | (Template 5) |
| PL-1791 | Non-specific agonist | (Template 5) |
| PL-1792 | Non-specific agonist | (Template 5) |
| PL-1605 | Non-specific antagonist | (Template 6) |
| PL-1758 | Non-specific | (Template 4) |
| PL-1877 | MC4-R specific | (Template 4) |
| PL-1902 | MC4-R specific | (Template 4) |
| PL-1909 | MC4-R specific agonist | (Template 4) |
| PL-1888 | MC4-R specific | (Template 7) |
| PL-1269 | MC4-R specific antagonist | (Template 3) |
| PL-1297 | MC4-R specific antagonist | (Template 3) |

Radiopharmaceutical Applications. In one embodiment, metallopeptides of this invention that are MC 1-R specific can be used, when complexed to $^{99m}$Tc as a radiodiagnostic agent, for imaging melanoma tumor metastases, and when complexed to rhenium-188 ($^{188}$Re), rhenium-186 ($^{186}$Re) or other therapeutic radionuclides as a radiotherapeutic agent for treatment of melanoma tumors and metastatic tumors.

Human melanoma has a complex antigenic profile. It is generally believed that malignant melanoma is derived by UV activity from DOPA positive melanocytes, the melanin (skin pigment) producing units. Primary diagnosis involves electron microscopic examination to reveal the presence or absence of pre-melanosomes. Melanotic melanoma is classified as dendritic, spindle, bizarre, large epitheloid, small nevus and so on. Amelanotic melanoma, on the other hand, is frequently misdiagnosed because the histology of these cells resembles that of malignant lymphoma, carcinoma or sarcoma. Therefore, morphological evaluation may not prove reliable for clinical diagnosis. Thus, there is a need for a receptor-specific diagnostic test, particularly to identify and locate metastatic melanoma tumors.

Several studies have documented the presence of melanotropin receptors on primary human melanoma cells. Melanotropin receptors have been reported as markers for melanotic and amelanotic human melanoma tumors. In particular, the presence of MC1-R has been demonstrated in human melanoma cells by an antibody to MC1-R.

The melanotropin bioactive sequence, or message segment, is a tetrapeptide, His-Phe-Arg-Trp (SEQ ID NO:1), that exist as a reverse turn. Within the reverse turn, the His, Phe, and Trp residues have been postulated to form a hydrophobic receptor binding surface. The His residue has recently been identified as a signal residue that helps discriminate between MC1-R and MC4-R. Thus, it is possible to design metallopeptides of this invention which are specific for MC1-R, and bind MC1-R with high affinity, but which are not specific for MC4-R, or which bind MC4-R with low affinity. One result is a $^{99m}$Tc-labeled radioimaging agent with high specific affinity and selectivity for the MC1-R. In addition, both agonists and antagonists metallopeptides of this invention are contemplated for comparative evaluation in imaging melanoma tumors.

The product can be formulated as a single-vial, lyophilized radiolabeling kit containing the peptide in an uncomplexed state, buffer, and a reducing agent for pertechnetate. To induce radiolabeling, resulting in a metallopeptide, the vial is incubated after the addition of sodium pertechnetate.

In one method of labeling with $^{99m}$Tc, a 5–10 μg sample of the peptide taken in 0.001 N aq. HCl is mixed with 1–30 mCi of generator-eluted Na$^{99m}$TcO$_4$ in a 5 ml serum vial. The volume of the resulting mixture is adjusted to 600 μl using injectable saline. A 400 μl volume of freshly prepared and nitrogen-purged phthalate-tartrate-Sn(II) buffer (40:10:1 mM) is added to the vial under a nitrogen head space. The vial is immediately sealed and placed in a shielded boiling water bath. After 15 minutes the vial is removed from the water bath and allowed to come to room temperature. The radiochemical purity, as calculated from HPLC profiles, ranges from 90–99%.

The peptides of this invention may alternatively be labeled with $^{99m}$Tc by other means, including use of stannous-tartrate-succinate buffer, stannous-EDTA-succinate buffer, stannous stabilized in glucoheptonate, or a stannous-borate-tartrate buffer, as well as other means of labeling with $^{99m}$Tc known in the art.

For radiopharmaceutical and other medical applications, the metallopeptides of this invention may be delivered to a subject by any means known in the art. This includes intravenous injection, subcutaneous injection, administration through mucous membranes, oral administration, dermal administration, regional administration to an organ, cavity or region, and the like.

Imaging may be any means known in the art, including gamma camera and SPECT imaging. Imaging may commence immediately after administration, and may include time course radiographic studies, and imaging may continue so long as images may be obtain d.

The MC1-R specific metallopeptides of this invention may be used as melanoma specific tumor imaging and staging agent. These uses include arly detection and localization of primary and disseminated lesions, identification of lymph nodes containing lesions, radioimmunoguided surgery applications and the like. Tumor imaging using a $^{99m}$Tc-labeled metallopeptide of this invention selective for the MC1-R will further help in formulating the optimal clinical treatment modality, whether surgical, radiation or chemotherapeutic.

Chemoprevention Applications. In another embodiment, metallopeptides of this invention that are MC1-R specific can be used as chemoprevention agents against sun-induced, such as by UV radiation, neoplastic activity in human skin. MC1-R agonist metallopeptides of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation.

In general, darker skinned individuals have lower incidences of skin cancer than lighter skinned people. The dark pigment eumelanin, a brown/black pigment incorporating dopa-based structural units, is the main photoprotective agent in skin. Lighter colored people have higher levels of pheomelanin, a red/yellow pigment having predominantly cysteine and related sulfur-based structural units, which is an inefficient UV absorber. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is also proposed to result from the same pathway by local production of melanotropic peptide from a POMC gene in the epidermis. Thus stimulation of eumelanin production and conversion of pheomelanin to eumelanin may be a desirable chemoprevention modality in blocking sun, or UV, induced neoplastic activity in skin.

A potent, high-affinity and highly selective MC1-R agonist metallopeptide of this invention can accordingly be used as a therapeutic chemoprevention agent for combating harmful sun, or UV, exposure that induces neoplastic activity in skin melanocytes.

Particularly for individuals previously diagnosed with melanoma or diagnosed as highly susceptible to melanoma, avoidance of any significant UV exposure is medically necessary. Currently, both physical screens, such as hats, long sleeves and so on, and various sun- or UV-protecting creams and formulations are utilized. However, the efficacy, both absolute and as a function of time, of even the best chemical sun block is limited, and physical screens are inappropriate for many activities. This results in individuals either receiving unacceptably high UV doses or foregoing normal activities, such as swimming, hiking, skiing, attending sporting events, employment in outdoor settings and so on.

Eumelanin production through activation of the MC1-R on epidermal melanocytes provides a natural shield against sun (UV) induced mutations and DNA damage than does any chemical sun block. Eumelanin is a better UV absorber over a wide range than any commercially available sun-protecting cream or formulation.

The metallopeptides for this application may be made with non-radioactive isotopes of rhenium, or other metals as specified herein, with metal ion complexation by any means specified herein or known in the art. The metallopeptides may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The metallopeptides may be administered by any systemic or partially systemic means known in the art, including but not limited to intravenous injection, subcutaneous injection, administration through mucous membranes, oral administration, dermal administration, skin patches, aerosols and the like.

Therapeutic Applications. In another embodiment, metallopeptides of this invention that are MC4-R agonists can be used as a therapeutic agent to modify energy metabolism and feeding behavior, including treatment of pathological obesity and related conditions. Metallopeptides of this invention that are MC4-R antagonists can also be used as a therapeutic agent in eating disorders, such as treatment of anorexia.

Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with the maturity-onset obesity syndrome that is associated with hyperphagia, hyperinsulinemia and hyperglycemia.

In yet another embodiment, metallopeptides of this invention may used as therapeutic agents for treatment of sexual dysfunction, including treatment of both male erectile dysfunction and female sexual dysfunction. In yet another embodiment, metallopeptides of this invention may be used as therapeutic agents for treatment of inflammation, including specifically MC1-R and MC3-R agonist metallopeptides.

The metallopeptides for this application may be made with non-radioactive isotopes of rhenium, or other metals as specified herein, with metal ion complexation by any means specified herein or known in the art. The metallopeptides may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The metallopeptides may be administered by any systemic or partially systemic means known in the art, including but not limited to intravenous injection, subcutaneous injection, administration through mucous membranes, oral administration, dermal administration, skin patches, aerosols and the like.

The invention is further illustrated by the following non-limiting examples.

EXAMPLE 1

Development of a Prototype Metallopeptide Library for the Melanocortin Receptor The library design was based on the tetrapeptide message sequence, His-Phe-Arg-Trp (6–9 sequence) (SEQ ID NO:1), of α-MSH. This sequence exists as a reverse turn, making it suitable for conversion into a metallopeptide format of this invention. In this approach metallopeptides were designed around a tripeptide $N_3S_1$ MBD designed for a rhenium metal ion. The MBD was derivatized to yield the pentapeptide Ac-His-Phe-Arg-Cys-Trp-$NH_2$ (SEQ ID NO:8) as a putative candidate for melanocortin ("MC") receptors. Further refinements in the structure were made in response to other considerations, including the chirality of amino acid side chains, yielding a template structure Ac-His-D-Phe-Arg-Cys-Trp-$NH_2$. The structure of this peptide after binding to rhenium is:

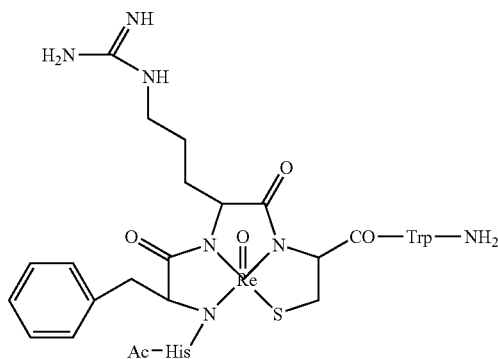

The template structure was used to define a small combinatorial library utilizing split synthesis methodologies. The final template selected for the combinatorial library was Ac-D-His-Xaa-D-Cys-Trp-$NH_2$, where Xaa was D-(2') Naphthylalanine, D-Trp, D-HomoPhe, or D-Phenylglycine. For this library, the peptide resin, Cys($S^tBu$)-Trp(Boc)-Resin was split in four equal parts. Each part was reacted with one of the four Xaa types. After coupling, the resin pools were mixed and synthesis continued in a single pool to couple the His residue. The final result was four separate peptides in a single pool, each peptide varying by one amino acid, in the Xaa position.

An $S^tBu$ OSPG group was used to protect the SH group during synthesis. After solid-phase assembly of the peptide chain using Fmoc chemistry with acid labile side chain protecting groups, the $S^tBu$ group was split using tributylphosphine. The resulting free SH-containing peptide-resin was treated with the rhenium transfer agent $Re(O)Cl_3$ $(PPh_3)_2$ in the presence of 1,8-Diazabicyclo[5,4,0] undec-7-ene as base. The resulting metallopeptide resin was then treated with TFA to cleave it from the resin and de-protect all the side chain protecting groups. The products were analyzed by mass spectrometry. HPLC analysis was performed and individual peaks collected and subjected to mass analysis. The resulting peptides were analyzed by electron spray mass spectrometry, yielding the predicted mass, including the rhenium complexed to the peptide.

EXAMPLE 2

Design and Synthesis of Melanocortin Receptor-Specific Metallopeptide Library The library was rationally designed based upon data relating to melanocortin receptors and peptide sequences specific to the melanocortin receptors, including melanotropin side-chain pharmacophores, D-Phe[7] and Trp[9], that interact with a hydrophobic network of receptor aromatic residues in transmembrane regions 4, 5, 6, and 7. Based on this design criterions, a pharmacophore for the melanocortin receptor was preliminarily defined, and a combinatorial library designed for identification of potent and receptor-selective agonists.

Based on the design criteria, the putative structure R-Aaa-Baa-L-Cys-Caa-$NH_2$ was selected, in which each of Aaa, Baa and Caa are selected from L- or D-isomers of 2-Nal (1), Phe (2), Trp (3), Tyr (4) and Ala (5), so that any one of the foregoing can be substituted for any one of Aaa, Baa or Caa. In the nomenclature adopted for the library design, the five amino acids were designated 1 through 5, with the isomerism conventionally notated, so that, for example, $Baa_2L$ refers to L-Phe in the Baa position.

The terminal R group was selected from Ac, $C_6H_5OOH$, $CH_3(CH_2)_5$—COOH, $C_6H_5CH~CH$—COOH (trans) and Pyridine-3-carboxylate. The terminal R group represents a truncated amino acid, and offers additional structural diversity.

A pool and split library synthesis scheme was employed such that 5,000 separate compounds were synthesized, resulting in 200 final pools each containing 25 different compounds, with the compounds differing solely by the amino acids in the Aaa and Baa position. Using this methodology, binding characteristics relating to the Caa amino acid or R terminal group can be identified through inter-group comparison, thereby simplifying the deconvolution strategy.

Figure 8:
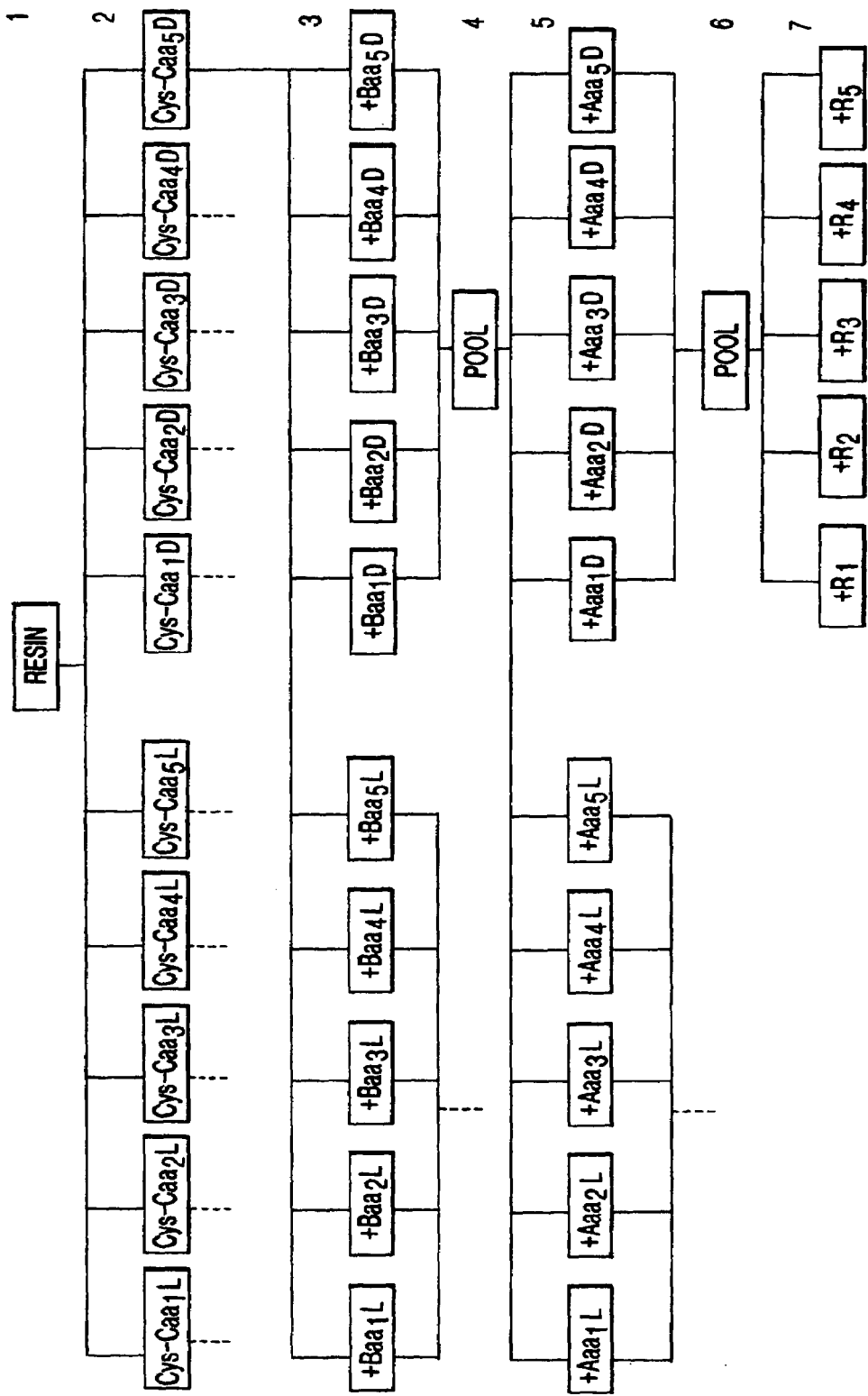
FIG. 8 is a flow chart of a split pool and combination synthesis method according to Example 2.

The library synthesis steps are set forth in FIG. 8. The resin of step 1 was divided into 10 groups. At step 2 each of $Caa_1L$ through $Caa_5D$ were coupled to an individual resin group, and L-Cys was coupled to each resin group, resulting in 10 groups and 20 couplings. Each of the resin groups of step 2 was then divided into 10 sub-groups as shown at step 3 (with only one subgroup illustrated at step 3, and for each subgroup of step 3, each of $Baa_1L$ through $Baa_5D$ were coupled to one group within the subgroup, resulting in 100 groups in 10 subgroups and 100 couplings. For each subgroup of step 3, the five $Baa_xL$ members and the five $Baa_xD$ members were separately pooled in step 4, resulting in 20 subgroups, with each subgroup containing five different sequences differing by the $Baa_x$ member. Each of the 20 subgroups of step 4 were then in step 5 divided into 10 groups (with only one shown for illustration purposes in FIG. 8), and for each subgroup, each of $Aaa_1L$ through $Aaa_5D$ were coupled to one group within the subgroup, resulting in 200 groups in 20 subgroups and 200 couplings. For each subgroup of step 5, the five $Aaa_xL$ members and the five $Aaa_xD$ members were separately pooled in step 6, resulting in 40 subgroups, with each subgroup containing twenty-five different sequences differing by the $Baa_x$ and $Aaa_x$ member. In step 7, each of the 40 subgroups of step 6 was were divided into five groups, and each of $R_1$ through $R_5$ were coupled to one group within the subgroup, resulting in 200 groups in 40 subgroups, with each group containing 25 different sequences differing by the $Baa_x$ and $Aaa_x$ member.

Peptides were synthesized using Fmoc chemistry, with side chain functionalities protected using acid labile groups. The SH group of the Cys residue was protected by a $S^tBu$ OSPG cleavable in presence of both base and acid labile groups using tributylphosphine as the reducing agent. The peptide chain was assembled on the solid phase using 1-(1H-benzotriazole-1-yl)-1,1,3,3,-tetramethyluronium tetrafluoroborate (TBTU) as a coupling agent. The SH group was then selectively unprotected and rhenium metal ion complexed using the rhenium transfer agent $Re(O)Cl_3(PPh_3)_2$ in the presence of 1,8-Diazabicyclo[5,4,0]undec-7-ene (DBU) as base. In this manner, the metal-peptide complex was formed with the peptide chain still tethered to the solid support. The metallopeptide was then liberated from the solid support by treatment with TFA. This solid phase approach to metal ion complexation is fully compatible with split synthesis methodologies employed in combinatorial libraries.

The synthesis process was performed using commercial automated synthesizers. Multiple manual synthesizers (such as those commercially available from SynPep Corporation, Dublin, Calif.) allow parallel synthesis of ten peptides simultaneously.

Figure 9:
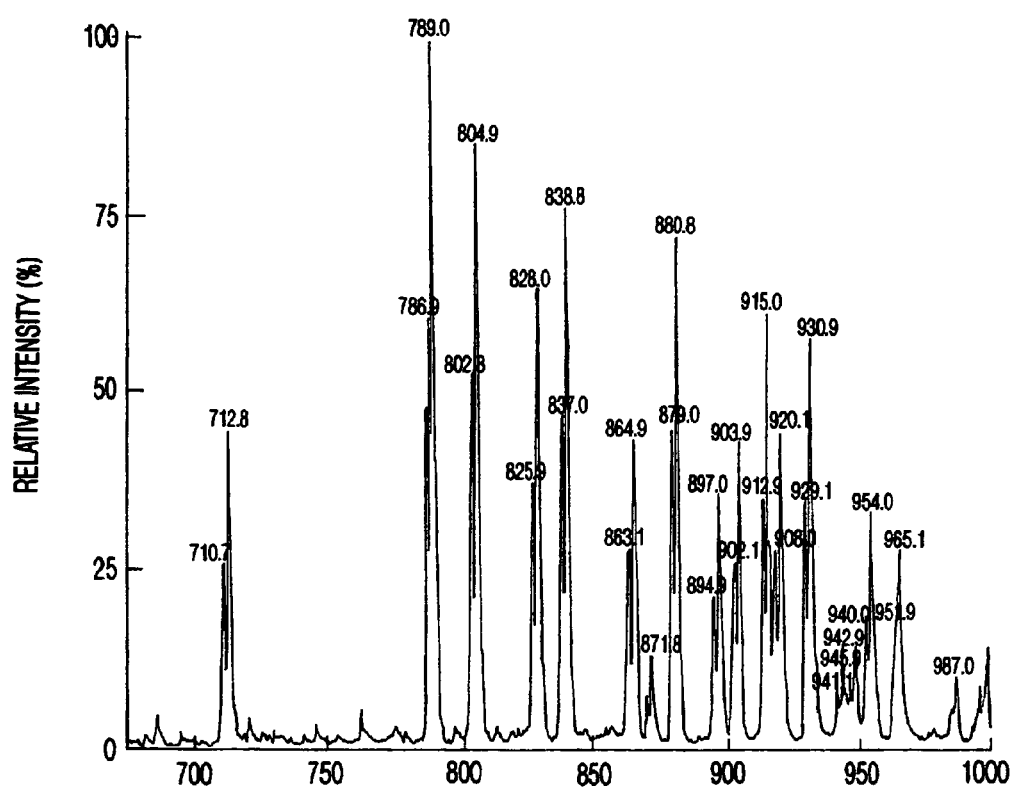
FIG. 9 is a mass spectrum of a library pool of 25 metallopeptides synthesized according to Example 2.

Quality control protocols were employed as required, and include HPLC, mass spectral analysis, and amino acid analysis on each individual pool of 25 compounds. The presence of each of pool constituent is established by molecular ion mass spectral analysis. Negative ion mode electron spray (ES) and matrix-assisted laser desorption (MALDI) techniques were employed. Using mass spectral analysis, three different measures were made: (a) the presence of up to 25 individual compounds by molecular ion peak measurement (assuming different masses for each compound), (b) confirmation that the molecular ion peaks show complexation to a rhenium metal ion, and (c) absence of peaks with molecular masses corresponding to peptides uncomplexed with metal ion. Rhenium is a mixture of two isotopes that differ in mass by 2 units (186 and 188) with a relative abundance of these isotopes of 1:2. The molecular ion profile of a metallopeptide appears as two peaks that differ by 2 mass units with integrated area ratios of 1:2. Rhenium thus acts as an internal mass spectral reference for these metallopeptides. A spectral analysis of one such pool of 25 compounds synthesized by the methods of this claim is shown at FIG. 9. Five sets of two metallopeptides in this pool have similar masses due to the presence of the same amino acids assembled in different sequences. The relative intensities of the peaks is due to differential ionization of individual compounds in the mixture. Each pair of peaks with mass unit differences of 2 and relative ratios of 1:2 are due to the relative abundance of two stable isotopes of rhenium (Re-185 and Re-187). The spectral analysis did not reveal any free uncomplexed linear peptides, which would be approximately 197 to 199 mass units less than the corresponding metallopeptide, due to the absence of the rhenium-oxo core.

Amino acid analysis of each pool of 25 metallopeptides was also employed, and was used to determine the relative equimolar ratio of each of 25 compounds in a pool. The synthetic protocols of split synthesis were designed to assure equimolar amounts of pool constituents.

EXAMPLE 3

Screening of Melanocortin Receptor-Specific Library

Metallopeptide library pools are screened for MC4-R receptor and MC1-R receptor binding activity in high throughput screening assays. The MC receptor-binding assay uses membrane preparations from B16-F1 or B16-F10 melanoma cells as the source of MC receptor. Cell membranes prepared from MC4-R-expressing 293 cells and negative control, untransfected 293 cells, ar substituted for B16-F1 or B16-F10 melanoma cell membranes in MC4-R specific binding assays. The MC receptor-binding assays use the Millipore Multi-Screen System and ar performed in 96-well Millipore filter plates (Durapore, 0.45 mm porosity) pre-blocked with 0.5% bovine serum albumin in phosphate buffered saline. Cell membrane preparations (12.5 μg/well) are incubated with 0.4 nM $^{125}$I-NDP-MSH in HEPES Buffer containing 0.2% bovine serum albumin. Non-specific binding is determined by addition of $10^{-6}$ M α-MSH or $10^{-7}$ M NDP-MSH. Metallopeptides to be tested are added to reaction wells at a final concentration of 1 mM. After incubation for 90 minutes at room temperature, the binding reaction is rapidly terminated by filtration to capture the membranes. Filters are washed 3 times with ice-cold PBS and air-dried. Individual filters are then punched from the plates and distributed into gamma counter tubes. Radioactivity associated with the membranes is determined in a Packard Cobra gamma counter. Specific binding is determined as the radioactivity in wells containing $^{125}$I-NDP-MSH alone minus the radioactivity in wells containing $10^{-6}$M α-MSH. Test compounds are screened in duplicate wells and are considered to be active where 1 μM concentrations inhibit >50% of the specific binding. Standard curves of unlabeled NDP-MSH will be included on each plate as an internal assay control.

A commercially available cAMP kit (R&D Systems, DE0350, low pH) is employed to evaluate agonist potential of metallopeptides that bind to MC4-R. 293 cells stably transfected with hMC-4 receptor, or B16-F1 melanoma cells, are grown to confluence in 96-well dishes. Cells are washed and fresh RPMI containing 0.2 mM isobutylmethylxanthine (cAMP phosphodiesterase) and varying concentrations of metallopeptides, or α-MSH as a positive control, are added, and the cells are incubated for 1 hour at 37° C. Medium is aspirated, and cell layers extracted with 150 μl of 0.1 M HCl. Total cAMP accumulation in 100 μl of cell extract is quantitated in 96-well plates by competitive immunoassay with the cAMP kit, using an acetylation modification. $EC_{50}$ values for test compounds will be calculated based on CAMP accumulation in cells treated with $10^{-6}$M α-MSH. The capabilities of both of these cell types to accumulate CAMP in the presence of α-MSH and MSH analog peptides ar documented in the scientific literature; see, for example, Ollman M M et al: *Science* 278:135–138, 1997.

EXAMPLE 4

Deconvolution of Melanocortin Receptor-Specific Library

Deconvolution of a positive pool is done by iterative re-synthesis and screening deconvolution approaches. The individual 25 constituents are synthesized separately, or alternatively in 5 smaller pools of 5 compounds each, with each pool screened in receptor binding assays. The latter approach is preferred where there is a high hit frequency in the preliminary screen. The compounds in pools with the best results (closest to receptor affinity in the nanomolar range and MC4-R to MC1-R selectivity of at least 100) are individually synthesized and screened.

EXAMPLE 5

Alternative Method of Deconvolution of Melanocortin Receptor-Specific Library In this example, an alternative method of mass spectral deconvolution of metallopeptide libraries is employed. The method is based on the internal signature of rhenium-complexed peptides (two isotopic peaks in 1:2 ratios differing by 2 mass units), which generally permits metallopeptide identification even in mixed solutions. A positive pool is incubated with receptor-bearing cells, the excess unbound compounds washed away under controlled conditions, and the cells treated with a solvent to disrupt metallopeptide binding and extract the metallopeptide in the solvent. Mass spectral analysis of the solvent reveals the metallopeptide or metallopeptides which are bound to the receptor-bearing cells, and through comparison to the quality control data it is possible to ascertain the specific metallopeptide or metallopeptides which are bound. This process provides high throughput of metallopeptide library screening.

EXAMPLE 6

Single Pot Synthesis of a Library of Four Metallopeptides of the General Structure Ac-His-Xaa-Cys-Trp-NH$_2$ A synthesis procedure similar to that described in Example 1 was used in making this library. A NovaSyn TGR resin for making peptide amides (substitution 0.2 mM/gm) was used. Fmoc synthetic strategy was employed using the following protected amino acids: Fmoc-Trp(Boc), Fmoc-Cys(S$^t$Bu), Fmoc-Xxx, and Fmoc-His(Trityl). The Xaa amino acids were Trp, HomoPhe, 2'-Naphthylalanine, and Phenylglycine. The peptide resin Cys(S$^t$Bu)-Trp-NH$_2$ was split into four equal pools and one of the Xaa amino acids was coupled to one individual pool. After completion of the coupling reaction, the four resin pools were mixed again. The synthesis proceeded with the coupling of His followed by acetylation of the N-terminus. After the complete assembly of the peptide chain Ac-His(Trt)-Xaa-Cys(S$^t$Bu)-Trp(Boc)-NH$_2$, the S$^t$Bu group was removed by treatment with DMF/tributylphosphine and rhenium-oxo metal ion was complexed as generally described above. The fully protected metallopeptide was deblocked and liberated from the solid support by treatment with a cleavage cocktail (95:5 mixture of trifluoroacetic acid—triisopropylsilane) for three hours. The metallopeptide library was recovered by precipitation using cold ether. The resulting pellet was washed twice and 0.5 ml of 95% acetic acid was added. After one-half hour 5 ml of water was added and the solution was freeze-dried yielding the desired library in solid form. Mass spectrometric analysis of the library pool confirmed the correct masses for all four members of the library:

TABLE 3

| Compound | Structure | Calculated Mass | Mass (M + 1) found |
| --- | --- | --- | --- |
| 1 | Ac-His-Phg-Cys-Trp-NH$_2$ (SEQ ID NO:6) | 815.7 and 817.6 | 815.2 and 816.7 |
| 2 | Ac-His-Trp-Cys-Trp-NH$_2$ (SEQ ID NO:3) | 868.8 and 870.7 | 868.0 and 870.1 |
| 3 | Ac-His-HPhe-Cys-Trp-NH$_2$ (SEQ ID NO:4) | 843.8 and 845.7 | 842.8 and 845.2 |
| 4 | Ac-His-2'Nal-Cys-Trp-NH$_2$ (SEQ ID NO:5) | 880.0 and 881.9 | 879.1 and 880.9 |

Figure 10:
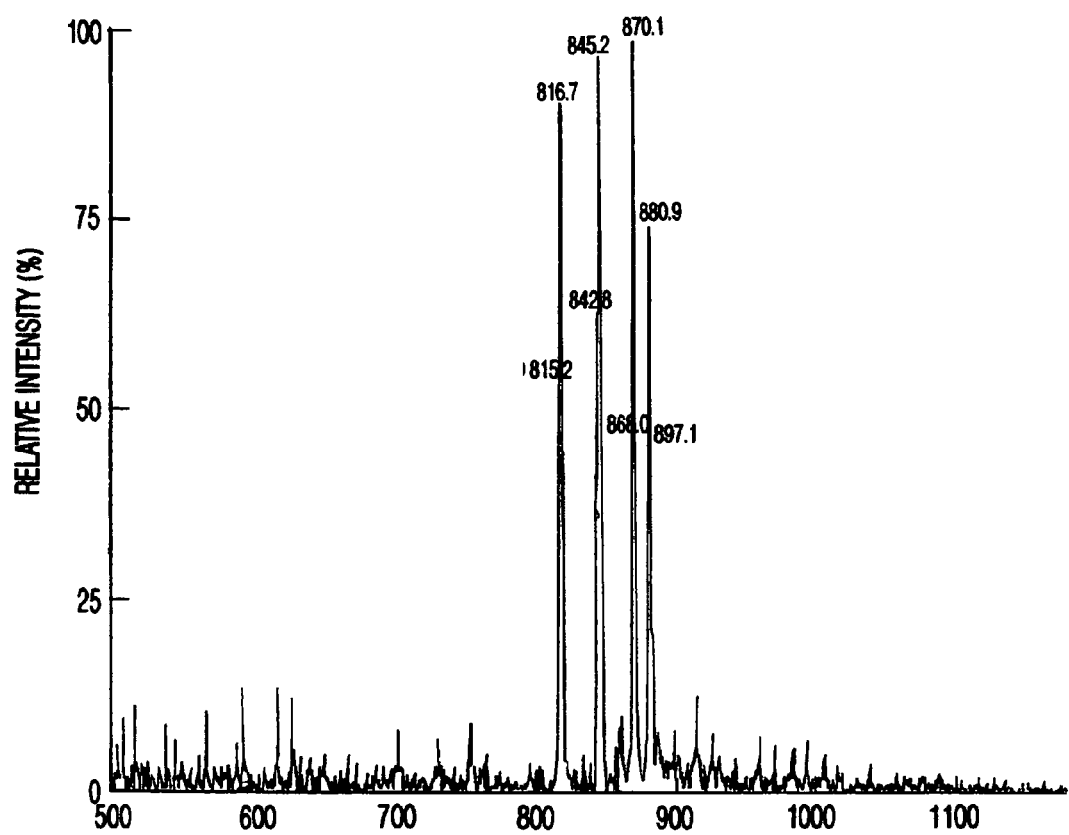
FIG. 10 is a mass spectrum of a library pool of 4 metallopeptides synthesized according to Example 6.

As noted in TABLE 3, two molecular ion peaks differing in mass units of 2 were calculated and observed for each structure; this difference is presumptively due to the presence of two natural isotopes of rhenium, Re-185 and Re-187, in the complexation step. In addition, the area under the observed peaks in the spectrometric analysis showed that for each structure the area was in a 1:2 ratio, which is identical to and presumptively related to the relative abundance of Re-185 and Re-187 isotopes. These results confirmed the complexation of rhenium to the peptides. The spectral analysis is shown at FIG. 10.

These results were also confirmed by HPLC analysis of this library of four compounds, which results were compared to HPLC analysis of each of the four individual members performed under identical HPLC conditions. As is evident from FIG. 11, each of the four member components are present in the library mixture. In the HPLC profile each of the metallopeptide has resolved into two isomers due to alternate orientations (syn and anti) of the rhenium oxo core. The HPLC analysis also revealed the lack of uncomplexed linear peptides in the preparation. All four compounds used for this comparison were individually prepared using methods identical to that described above for synthesis of the library. The HPLC profiles are shown as FIGS. 11A to 11E.

EXAMPLE 7

Synthesis of MC1-R Specific Metallopeptides for Use as Chemoprevention Agent High potency metallopeptides are also provided with N-terminal modifications. Systematic N-terminal modifications are made based upon the limited data available in the literature related to receptor-binding affinities of peptide analogs for various MC receptor types. In general, these studies indicate that the His6 residue may be a critical factor in determining receptor selectivity for MC1-R (peripheral) versus MC4-R (brain). Three-dimensional molecular models of the human melanocortin receptor have been developed based upon the electron cryo-microscopic structure of bacteriorhodopsin and the electron density footprint of bovine rhodopsin. By modeling known potent agonists into the proposed binding sites, specific ligand-receptor interactions have been identified. By this means, researchers have tentatively identified melanotropin side-chain pharmacophores, D-Ph$^7$ and Trp$^9$, and have proposed that these interact with a hydrophobic network of receptor aromatic residues in transmembrane regions 4, 5, 6, and 7. The findings of these results are utilized in selecting N-terminal modifications for the metallopeptide core. Groups with hydrophobic and/or hydrogen bonding potential are investigated in a systematic and stereospecific manner, with contemporaneous assaying of potency and MC1-R specificity of the resulting metallopeptides. The influence of the His residue on bioactivity is also investigated. Two series of metallopeptides are synthesized:

Rheniumoxo-[R-His-D-Phe-Arg-Cys-Trp-$NH_2$] and
Rheniumoxo-[R-D-Phe-Arg-Cys-Trp-$NH_2$]

Where R is a pair consisting of a hydrophobic side chain and hydrophilc side chain with hydrogen bonding potential which is selected from the following groups:

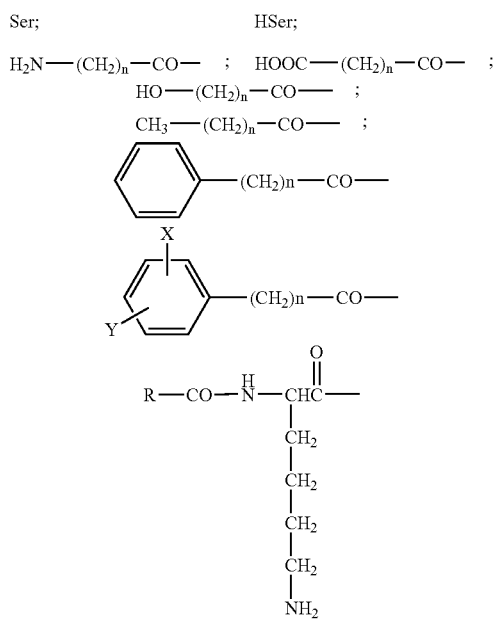

And where n is from 2 to 9 and X and/or Y ar selected from H, OH, Cl, Br, I, $NH_2$, $OCH_3$, $NO_2$ and similar groups.

EXAMPLE 8

Skin Darkening in *Anolis Carolinensis*

PT-1145 complexed with rhenium (0.65 mg taken in a 50 mL vehicle) was injected intraperitoneally in a lizard (*Anolis carolinensis*) that was pre-conditioned for a skin darkening experiment. The pre-conditioning involved leaving the lizards in a well-lit white background for 24 hours. Within 10–15 minutes after injection, the skin coat color turned from bright green to dark brown to black. The skin coat color remained dark during the five-hour observation period. Lizards injected with the vehicle alone (PBS buffer containing 1% each of DMF and beta-cyclodextran) did not show any change in their skin color during the 5 hour observation period.

Each of the foregoing is merely illustrative, and other equivalent embodiments are possible and contemplated.

Although this invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above are hereby incorporated by reference.

The preceding examples can be repeated with similar success by substituting the generically or specifically described reactants and/or operating conditions of this invention for those used in the preceding examples.

---

What is claimed is:

1. A manufactured peptide and pharmaceutically acceptable salts thereof comprising a metal ion-binding domain comprising two or more contiguous amino acids and a biological-function domain specific for one or more melanocortin receptors and a metal ion selected from the group consisting of rhenium and technetium complexed to the metal ion-binding domain, wherein at least a portion of said biological-function domain is co-extensive with at least a portion of the metal ion-binding domain, and wherein said biological-function domain is conformationally constrained upon complexing the metal ion-binding domain with a metal ion, and wherein the peptide or salt thereof is substantially more specific for one or more melanocortin receptors when the metal ion-binding domain is complexed with a metal ion than is the peptide or salt thereof when the metal ion-binding domain is not complexed with a metal ion, wherein the peptide is of the formulas:

$R_1$-Lll-Aaa-Bbb-Ccc-$R_2$, $R_1$-Bbb-Aaa-Ccc-$R_2$, $R_1$-Ddd-Bbb-Aaa-$R_3$, $R_4$-Eee-Bbb-Ccc-$R_2$, $R_1$-Hhh-Aaa-Bbb-Ccc-$R_5$, or $R_1$-Iii-Iii-Ccc-Jjj-Kkk-$R_2$, wherein $R_1$ comprises a functionality that potentiates the intrinsic activity of the remainder of the peptide, including but not limited to providing an auxiliary or secondary receptor contact;

Aaa is an L- or D-configuration cationic amino acid with a positively charged side chain;

Bbb is an L- or D-configuration amino acid with an aromatic side chain;

Ccc is an amino acid that provides both a nitrogen atom (N), from the alpha amino group, and a sulfur atom (S), from a side chain group, for metal ion complexation;

Lll is a D-configuration amino acid with an aromatic side chain;

$R_2$ is optionally present, and if present, comprises an amino acid with an aromatic side chain;

Ddd is an amino acid that provides an S, from a side chain group, for metal ion complexation;

$R_3$ is an amino acid with an aromatic side chain that provides an N for metal ion complexation;

$R_4$ is a functionality that provides a cationic center;

Eee is an uncharged L- or D-configuration amino acid that provides an N for metal ion complexation:

$R_5$ is an amide, substituted amide, ester or carboxylate group, or comprises an L- or D-configuration amino acid;

Hhh is an L- or D-configuration cationic amino acid with a positively charged side chain;

Iii is an L- or D-configuration amino acid that provides an N for metal ion complexation;

Jjj is an L- or D-configuration amino acid with an aromatic side chain; and

Kkk is an L- or D-configuration cationic amino acid with a positively charged side chain.

2. A manufactured peptide and pharmaceutically acceptable salts thereof comprising a metal ion-binding domain comprising two or more contiguous amino acids and a biological-function domain specific for one or more melanocortin receptors and a metal ion selected from the group consisting of rhenium and technetium complexed to the metal ion-binding domain, wherein at least a portion of said biological-function domain is co-extensive with at least a portion of the metal ion-binding domain, and wherein said biological-function domain is conformationally constrained upon complexing the metal ion-binding domain with a metal ion, and wherein the peptide or salt thereof is substantially more specific for one or more melanocortin receptors when the metal ion-binding domain is complexed with a metal ion than is the peptide or salt thereof when the metal ion-binding domain is not complexed with a metal ion, wherein the peptide is of the formula:

$R_1$-Fff-Aaa-Ggg-Ccc-$R_5$, wherein $R_1$ comprises a functionality that potentiates the intrinsic activity of the remainder of the peptide, including but not limited to providing an auxiliary or secondary receptor contact;

Aaa is an L- or D-configuration cationic amino acid with a positively charged side chain;

Ccc is an amino acid that provides both a nitrogen atom (N), from the alpha amino group, and a sulfur atom (S), from a side chain group, for metal ion complexation;

Fff is an L- or D-configuration aromatic amino acid wherein the aromatic ring of the aromatic side chain of Fff is substituted with halogen, alkyl or aryl groups or is a D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), Tyr(BzlCl$_2$), Tic, Tiq or Tca, or derivative, analog or homolog thereof;

Ggg is an L- or D-configuration aromatic amino acid; and $R_5$ is an amide, substituted amide, ester or carboxylate group, or comprises an L- or D-configuration amino acid.

3. The peptide of claim 1 wherein $R_1$ comprises an amino acid chain of from one to about four neutral or charged L- or D-configuration amino acid residues.

4. The peptide of claim 1 wherein $R_1$ comprises a linear or branched alkyl, aryl, alkene, alkenyl, or aralkyl chain.

5. The peptide of claim 1 wherein Aaa is an L-configuration Lys, Arg, Orn, Dpr or Dbu, or derivative, analog or homolog thereof.

6. The peptide of claim 1 wherein Aaa provides an N for metal ion complexation.

7. The peptide of claim 1 wherein Bbb is a D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser (Bzl), Lys(Z), Lys(Z-2'Br), Lys(Bz), Thr(Bzl), Cys(Bzl), or Tyr(BzlCl$_2$), or derivative, analog or homolog thereof.

8. The peptide of claim 1 wherein the aromatic ring of the aromatic side chain of Bbb is substituted with one or more halogen, alkyl or aryl groups.

9. The peptide of claim 1 wherein Bbb provides an N for metal ion complexation.

10. The peptide of claim 1 wherein Ccc is an L- or D-configuration Cys, Pen or Hcys.

11. The peptide of claim 1 wherein Lll is a D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser (Bzl), Lys(Z), Lys(Z-2'Br), Lys(Bz), Thr(Bzl), Cys(Bzl), or Tyr(BzlCl₂), or derivative, analog or homolog thereof.

12. The peptide of claim 1 wherein the aromatic ring of the aromatic side chain of Lll is substituted with one or more halogen, alkyl, or aryl groups.

13. The peptide of claim 1 wherein Lll does not provide an N for metal ion complexation.

14. The peptide of claim 1 wherein R₂ is an L- or D-configuration Phe, Trp, Phe(4'Cl), Phe(3',4' Di-Cl), Phe (4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr (Bzl), Cys(Bzl) or Tyr(BzlCl₂), or derivative, analog or homolog thereof.

15. The peptide of claim 1 wherein the C-terminus of R₂ is amidated.

16. The peptide of claim 1 wherein R₂ is a des-carboxyl amino acid corresponding to an L- or D-configuration Phe, Trp, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser (Bzl), Lys(Z), Lys(Z-2'Br), Lys(Bz), Thr(Bzl), Cys(Bzl) or Tyr(BzlCl₂).

17. The peptide of claim 1 wherein R₂ is absent.

18. The peptide of claim 1 wherein Ddd is an L- or D-configuration Cys, Pen or Hcys.

19. The peptide of claim 1 wherein R₃ is an L- or D-configuration Phe, Trp, Phe(4'Cl), Phe(3',4' Di-Cl), Phe (4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr (Bzl), Cys(Bzl) or Tyr(BzlCl₂), or derivative, analog or homolog thereof.

20. The peptide of claim 1 wherein the C-terminus of R₃ is amidated.

21. The peptide of claim 1 wherein R₃ is a des-carboxyl amino acid corresponding to an L- or D-configuration Phe, Trp, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser (Bzl), Lys(Z), Lys(Z-2'Br), Lys(Bz), Thr(Bzl), Cys(Bzl) or Tyr(BzlCl₂).

22. The peptide of claim 1 wherein R₄ is an L- or D-configuration Lys, Arg, Orn, Dpr or Dbu, or derivative, analog or homolog thereof.

23. The peptide of claim 1 wherein the N-terminus of R₄ is functionalized with a neutral amino acid or non-peptide group comprising a linear or branched alkyl, aryl, alkene, alkenyl or aralkyl chain.

24. The peptide of claim 1 wherein Eee is a Gly or an L-configuration Ala, Nle, Leu, Val, Phe or Trp, or derivative, analog or homolog thereof.

25. The peptide of claim 1 wherein Eee is an amino acid with an aliphatic side chain.

26. The peptide of claim 2 wherein Fff does not provide an N for metal ion complexation.

27. The peptide of claim 2 wherein Ggg is an L-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser (Bzl), Lys(Z), Lys(Z-2'Br), Lys(Bz), Thr(Bzl), Cys(Bzl) or Tyr(BzlCl₂), and derivatives, analogs or homologs thereof, including both natural and synthetic amino acids.

28. The peptide of claim 2 wherein the aromatic ring of the aromatic side chain of Ggg may be substituted with halogen, alkyl or aryl groups.

29. The peptide of claim 2 wherein Ggg provides an N for metal ion complexation.

30. The peptide of claim 1 wherein R₅ is an L- or D-configuration aromatic, aliphatic, neutral or charged amino acid, optionally further comprising an amide group.

31. The peptide of claim 1 wherein Hhh is an L-configuration Lys, Arg, Orn, Dpr or Dbu, and derivatives, analogs or homologs thereof, including both natural and synthetic amino acids.

32. The peptide of claim 1 wherein Hhh does not provide an N for metal ion complexation.

33. The peptide of claim 1 wherein Iii is an Ala, Gly, Nle, Val, Leu, Ile, His, Lys, or Arg, and derivatives, analogs or homologs thereof, including both natural and synthetic amino acids.

34. The peptide of claim 1 wherein Jjj is a D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser (Bzl), Lys(Z), Lys(Z-2'Br), Lys(Bz), Thr(Bzl), Cys(Bzl), or Tyr(BzlCl₂), and derivatives, analogs or homologs thereof.

35. The peptide of claim 1 wherein the aromatic ring of the aromatic side chain of Jjj is substituted with one or more halogen, alkyl or aryl groups.

36. The peptide of claim 1 wherein Jjj does not provide an N for metal ion complexation.

37. The peptide of claim 1 wherein Kkk is an L-configuration Lys, Arg, Orn, Dpr or Dbu, or derivative, analog or homolog thereof.

38. The peptide of claim 1 wherein Kkk does not provide an N for metal ion complexation.

39. The peptide of claim 2 wherein R₁ comprises an amino acid chain of from one to about four neutral or charged L- or D-configuration amino acid residues.

40. The peptide of claim 2 wherein R₁ comprises a linear or branched alkyl, aryl, alkene, alkenyl, or aralkyl chain.

41. The peptide of claim 2 wherein Aaa is an L-configuration Lys, Arg, Orn, Dpr or Dbu, or derivative, analog or homolog thereof.

42. The peptide of claim 2 wherein Aaa provides an N for metal ion complexation.

43. The peptide of claim 2 wherein Ccc is an L- or D-configuration Cys, Pen or Hcys.

44. A manufactured peptide and pharmaceutically acceptable salts thereof comprising a metal ion-binding domain comprising two or more contiguous amino acids and a biological-function domain specific for one or more melanocortin receptors and a metal ion selected from the group consisting of rhenium and technetium complexed to the metal ion-binding domain, wherein at least a portion of said biological-function domain is co-extensive with at least a portion of the metal ion-binding domain, and wherein said biological-function domain is conformationally constrained upon complexing the metal ion-binding domain with a metal ion, and wherein the peptide or salt thereof is substantially more specific for one or more melanocortin receptors when the metal ion-binding domain is complexed with a metal ion than is the peptide or salt thereof when the metal ion-binding domain is not complexed with a metal ion, wherein the peptide is of the formula:

R₁-Fff-Aaa-Ggg-Ccc-R₅, wherein

R₁ comprises a functionality that potentiates the intrinsic activity of the remainder of the peptide, including but not limited to providing an auxiliary or secondary receptor contact;

Aaa is an L- or D-configuration cationic amino acid with a positively charged side chain;

Ccc is an amino acid that provides both a nitrogen atom (N), from the alpha amino group, and a sulfur atom (S), from a side chain group, for metal ion complexation;

Fff is an L- or D-configuration aromatic amino acid;

Ggg is an L- or D-configuration aromatic amino acid wherein the aromatic ring of the aromatic side chain of Ggg is substituted with halogen, alkyl or aryl groups or is an L-configuration Phe, Phe(4'Cl), Phe(3',4' Di-Cl), Phe(4'-nitro), Phe(4'-methyl), Phe(4'-Phenyl), Hphe, Pgl, 1-Nal, 2-Nal, Ser(Bzl), Lys(Z), Lys(Z-2'Br), Lys(Bz), Thr(Bzl), Cys(Bzl) or Tyr(BzlCl$_2$), and derivatives, analogs or homologs thereof, including both natural and synthetic amino acids; and $R_5$ is an amide, substituted amide, ester or carboxylate group, or comprises an L- or D-configuration amino acid.

45. The peptide of claim 44 wherein Ggg provides an N for metal ion complexation.

46. The peptide of claim 44 wherein $R_1$ comprises an amino acid chain of from one to about four neutral or charged L- or D-configuration amino acid residues.

47. The peptide of claim 44 wherein $R_1$ comprises a linear or branched alkyl, aryl, alkene, alkenyl, or aralkyl chain.

48. The peptide of claim 44 wherein Aaa is an L-configuration Lys, Arg, Orn, Dpr or Dbu, or derivative, analog or homolog thereof.

49. The peptide of claim 44 wherein Aaa provides an N for metal ion complexation.

50. The peptide of claim 44 wherein Ccc is an L- or D-configuration Cys, Pen or Hcys.

51. The peptide of claim 44 wherein Fff is a D-configuration Phe, Phe(4'Cl), Phe(3',4' Di-Cl), Phe(4'-nitro), Phe(4'-methyl), Phe(4'-Phenyl), Hphe, Pgl, Trp, 1-Nal, 2-Nal, Ser(Bzl), Lys(Z), Lys(Z-2'Br), Lys(Bz), Thr(Bzl), Cys(Bzl), Tyr(BzlCl$_2$), Tic, Tiq or Tca, or derivative, analog or homolog thereof.

52. The peptide of claim 44 wherein the aromatic ring of the aromatic side chain of Fff is substituted with halogen, alkyl or aryl groups.

53. The peptide of claim 44 wherein Fff does not provide an N for metal ion complexation.

54. The peptide of claim 44 wherein $R_5$ is an L- or D-configuration aromatic, aliphatic, neutral or charged amino acid, optionally further comprising an amide group.

* * * * *